US009902971B2

(12) United States Patent
Frendewey et al.

(10) Patent No.: US 9,902,971 B2
(45) Date of Patent: *Feb. 27, 2018

(54) METHODS FOR PRODUCING A MOUSE XY EMBRYONIC (ES) CELL LINE CAPABLE OF PRODUCING A FERTILE XY FEMALE MOUSE IN AN F0 GENERATION

(71) Applicant: Regeneron Pharmaceuticals, Inc., Tarrytown, NY (US)

(72) Inventors: David Frendewey, New York, NY (US); Gustavo Droguett, New City, NY (US); Anthony Gagliardi, Hopewell Junction, NY (US); Junko Kuno, Holmes, NY (US); Wojtek Auerbach, Ridgewood, NJ (US); David M. Valenzuela, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/751,807

(22) Filed: Jun. 26, 2015

(65) Prior Publication Data

US 2015/0376651 A1 Dec. 31, 2015

Related U.S. Application Data

(60) Provisional application No. 62/017,582, filed on Jun. 26, 2014, provisional application No. 62/017,627, filed on Jun. 26, 2014.

(51) Int. Cl.
*C12N 15/90* (2006.01)
*C12N 5/0735* (2010.01)
*C12N 15/85* (2006.01)
*A01K 67/027* (2006.01)

(52) U.S. Cl.
CPC ...... *C12N 15/8509* (2013.01); *A01K 67/0275* (2013.01); *A01K 67/0276* (2013.01); *A01K 67/0278* (2013.01); *C12N 5/0606* (2013.01); *C12N 15/907* (2013.01); *A01K 2217/075* (2013.01); *A01K 2227/105* (2013.01); *A01K 2267/02* (2013.01); *A01K 2267/0393* (2013.01); *C12N 2500/60* (2013.01); *C12N 2517/00* (2013.01)

(58) Field of Classification Search
CPC .......... C12N 15/8509; C12N 5/0606; C12N 15/907; C12N 2500/60; C12N 2517/00; A01K 67/0275; A01K 67/0276; A01K 67/0278; A01K 2217/075; A01K 2227/105; A01K 2267/02; A01K 2267/0393
See application file for complete search history.

(56) References Cited

U.S. PATENT DOCUMENTS

| | | |
|---|---|---|
| 6,372,956 B1 | 4/2002 | Goldsmith et al. |
| 6,566,579 B1 | 5/2003 | Jaisser et al. |
| 7,294,754 B2 | 11/2007 | Poueymirou et al. |
| 7,771,967 B2 | 8/2010 | Huang et al. |
| 8,502,018 B2 | 8/2013 | Murphy et al. |
| 8,697,359 B1 | 4/2014 | Zhang |
| 9,149,026 B2 | 10/2015 | Auerbach et al. |
| 9,228,208 B2 | 1/2016 | Frendewey et al. |
| 9,398,762 B2 | 7/2016 | Auerbach et al. |
| 2003/0134318 A1 | 7/2003 | Case et al. |
| 2003/0175968 A1 | 9/2003 | Golic et al. |
| 2003/0204862 A1* | 10/2003 | Kuehn ............... C12N 15/8509 800/18 |
| 2004/0018626 A1 | 1/2004 | Murphy et al. |
| 2004/0197317 A1 | 10/2004 | Rao et al. |
| 2005/0144655 A1 | 6/2005 | Economides et al. |
| 2007/0155013 A1 | 7/2007 | Akaike et al. |
| 2008/0066197 A1 | 3/2008 | Ying et al. |
| 2008/0113437 A1 | 5/2008 | Joly et al. |
| 2008/0124801 A1 | 5/2008 | Mee et al. |
| 2008/0299580 A1 | 12/2008 | DeKelver et al. |
| 2009/0055943 A1 | 2/2009 | Economides et al. |
| 2010/0218264 A1 | 8/2010 | Cui et al. |
| 2011/0207221 A1 | 8/2011 | Cost et al. |
| 2011/0307968 A1 | 12/2011 | Auerbach et al. |

(Continued)

FOREIGN PATENT DOCUMENTS

| | | |
|---|---|---|
| EP | 1516924 A1 | 3/2005 |
| EP | 1360287 B1 | 9/2012 |

(Continued)

OTHER PUBLICATIONS

McClelland et al., Asian Journal of Andrology, 14: 164-171, 2012.*
Abramov et al., Proceedings of Measuring Behavior, 335-336, 2008.*
"C57BL/6NTac" from the Taconic website, http://www.taconic.com/mouse-model/black-6-b6ntac, accessed on Nov. 17, 2016.*
Kunieda, Genomics 13(1): 236-237, 1992.*
Festing et al., Mammalian Genome 10: 836, 1999.*
"Stem Cells: Scientific Progress and Future Research Directions," National Institute of Health, Department of Health and Human Services, (2001).
Affara, "The role of the Y chromosome in male infertility," Expert Rev. Mol. Med., vol. 2001, pp. 1-16, 2001.
Alton et al., "The behavior of the X- and Y-chromosomes in the oocyte during meiotic prophase in the B6.Y(Tir) sex-reversed mouse ovary," Reproduction, vol. 135(2), pp. 241-252, 2008.

(Continued)

*Primary Examiner* — Thaian N Ton
(74) *Attorney, Agent, or Firm* — Yongjin Choi; Alston & Bird LLP

(57) ABSTRACT

Methods and compositions are provided for generating targeted genetic modifications on the Y chromosome or a challenging target locus. Compositions include an in vitro culture comprising an XY pluripotent and/or totipotent animal cell (i.e., XY ES cells or XY iPS cells) having a modification that decreases the level and/or activity of an Sry protein; and, culturing these cells in a medium that promotes development of XY F0 fertile females. Such compositions find use in various methods for making a fertile female XY non-human mammal in an F0 generation.

41 Claims, 5 Drawing Sheets

(56) References Cited

U.S. PATENT DOCUMENTS

| | | |
|---|---|---|
| 2012/0272349 A1 | 10/2012 | Ochiya et al. |
| 2012/0315670 A1 | 12/2012 | Jacobson et al. |
| 2013/0309670 A1 | 11/2013 | Frendewey et al. |
| 2014/0068797 A1 | 3/2014 | Doudna et al. |
| 2014/0273226 A1 | 9/2014 | Wu |
| 2014/0273234 A1 | 9/2014 | Zhang et al. |
| 2014/0301990 A1 | 10/2014 | Gregory et al. |
| 2014/0309487 A1 | 10/2014 | Lee et al. |
| 2014/0310828 A1 | 10/2014 | Lee et al. |
| 2014/0342456 A1 | 11/2014 | Mali et al. |
| 2014/0359795 A1 | 12/2014 | Fahrenkrug et al. |
| 2015/0067901 A1 | 3/2015 | Auerbach et al. |
| 2015/0079680 A1 | 3/2015 | Bradley et al. |
| 2015/0140664 A1 | 5/2015 | Byrne et al. |
| 2015/0159174 A1 | 6/2015 | Frendewey et al. |
| 2015/0159175 A1 | 6/2015 | Frendewey et al. |
| 2015/0376650 A1 | 12/2015 | Auerbach et al. |
| 2016/0046960 A1 | 2/2016 | Frendewey et al. |
| 2016/0060657 A1 | 3/2016 | Frendewey et al. |
| 2016/0108369 A1 | 4/2016 | Kuno et al. |
| 2016/0145646 A1 | 5/2016 | Frendewey et al. |
| 2016/0177339 A1 | 6/2016 | Voronina et al. |

FOREIGN PATENT DOCUMENTS

| | | |
|---|---|---|
| EP | 3009511 A2 | 4/2016 |
| WO | WO 2002/066630 A1 | 8/2002 |
| WO | WO 2003/087341 A2 | 10/2003 |
| WO | WO 2006/044962 A1 | 4/2006 |
| WO | WO 2007/117410 A2 | 10/2007 |
| WO | WO 2008/151081 A1 | 12/2008 |
| WO | WO 2011/044684 A1 | 4/2011 |
| WO | WO 2011/051390 A1 | 5/2011 |
| WO | WO 2011/078665 A1 | 6/2011 |
| WO | WO 2011/154927 A2 | 12/2011 |
| WO | WO 2011/156723 A1 | 12/2011 |
| WO | WO 2012/012667 A2 | 1/2012 |
| WO | WO 2012/018726 A1 | 9/2012 |
| WO | WO 2012/129198 A1 | 9/2012 |
| WO | WO 2013/063361 A1 | 5/2013 |
| WO | WO 2013/163394 A1 | 10/2013 |
| WO | WO 2013/169802 A1 | 11/2013 |
| WO | WO 2013/176772 A1 | 11/2013 |
| WO | WO 2014/104878 A1 | 7/2014 |
| WO | WO 2014/172470 A2 | 10/2014 |
| WO | WO 2014/172489 A2 | 10/2014 |
| WO | WO 2015/040402 A1 | 3/2015 |
| WO | WO 2015/077290 A2 | 5/2015 |
| WO | WO 2015/088643 A1 | 6/2015 |
| WO | WO 2015/05928 A1 | 7/2015 |
| WO | WO 2015/163733 A1 | 10/2015 |
| WO | WO 2015/166272 A2 | 11/2015 |
| WO | WO 2015/188109 A1 | 12/2015 |
| WO | WO 2015/200805 A2 | 12/2015 |
| WO | WO 2016/061073 A1 | 4/2016 |
| WO | WO 2016/061374 A1 | 4/2016 |
| WO | WO 2016/081923 A2 | 5/2016 |
| WO | WO 2016/089866 A1 | 6/2016 |
| WO | WO 2016/100819 A1 | 6/2016 |
| WO | WO 2016/164977 A1 | 10/2016 |

OTHER PUBLICATIONS

Berdien, et al., "TALEN-mediated editing of endogenous T-cell receptors facilitates efficient reprogramming of T lymphocytes by lentiviral gene transfer," Gene Therapy, 21, 539-548 (2014).

Bernart, et al., "Frozen storage of Ham's F-10 medium for human in-vitro fertilization," Human Reproduction, 5:610-612 (1990).

Bronson et al., "High incidence of XXY and XYY males among the offspreing of female chimeras from embryonic cells," Proc. Natl. Acad. Sci. USA, Apr. 1995, vol. 92:3120-3123.

Byrne et al., "Multi-kilobase homozygous targeted gene replacement in human induced pluripotent stem cells," Nucleic Acids Research, Vo. 43(3), p. e21, 2014 (epub Nov. 20, 2014).

Certificate of Analysis for KNOCKOUT™ DMEM, Life Technologies, Catalog No. 10829, Lot No. 1677060, May 21, 2015.

Chen et al., "High-frequency genome editing using ssDNA oligonucleotides with zinc-finger nucleases," Nature Methods, vol. 8(9), pp. 753-755, 2011. (Jul. 17, 2011).

Cheng, et al., "Improved generation of C57BL/6J mouse embryonic stem cells in a defined serum-free media,"Genesis, Jun. 2004, vol. 39(2):100-104.

Chung, et al., "Human Embryonic Stem Cell Lines Generated without Embryo Destruction", Cell Stem Cell 2, pp. 113-117 (Feb. 2008).

Cobb and Zhao, "Direct cloning of large genomic sequences," Nature Biotechnology, 2012, vol. 30(5), pp. 405-406.

Colvin et al., "Male-to-Female Sex Reversal in Mice Lacking Fibroblast Growth Factor 9," Cell, Mar. 23, 2001, vol. 104:875-889.

Cong et al., "Multiplex Genome Engineering Using CRISPR/Cas Systems," Science, vol. 339(6121), pp. 819-823 plus Supplemental Materials, Jan. 3, 2013.

Cui, et al., "Targeted integration in rat and mouse embryos with zinc-fnger nucleases," Nature Biotechnology, vol. 29, No. 1, 64-68 (Jan. 2011).

Dechiara, T.M., et al., "VelociMouse: Fully ES Cell-Derived F0-Generation Mice Obtained from the Injection of ES Cells into Eight-Cell-Stage Embryos," Jan. 1, 2009, Methods in Molecular Biology, 530(16): 311-324.

Doudna et al., "The new frontier of genome engineering with CRISPR-Cas9," Science, vol. 346(6213), pp. 1258096-1-1258096-9, Nov. 28, 2014.

Fan et al., "107 Genetic Inactivation of the Sry Gene in Argali Wild and Romney Domestic Sheep with CRISPR/Cas Systems for Producing Sex-Reversed Female Animals," Reproduction Fertility and Development, vol. 26(1), p. 167, Dec. 5, 2013.

Flisikowska, et al., "Efficient Immunoglobulin Gene Disruption and Targeted Replacement in Rabbit Using Zinc Finger Nucleases," Plos one, vol. 6 Issue 6 (Jun. 2011).

Gennequin, et al., "CRISPR/Cas-induced double-strand breaks boost the frequency of gene replacements for humanizing the mouse Cnr2 gene," Biochem. Biophys. Res. Commun., (2013), http://dx.doi.org/10.1016/j.bbrc.2013.10.138.

Hoekstra et al., Multiple origins of XY female mice (genus *Akodon*): phylogenetic and chromosomal evidence,: Proc. R. Soc. Lond. B, Sep. 22, 2000, vol. 267(1455):1825-31.

International Search Report of International Application No. PCT/US2011/039997, dated Sep. 6, 2011.

Johnson, et al., "A rapid assay to quantify the cleavage efficiency of custom-designed nucleases in planta," Plant Mol Biol, 82:207-221 (2013).

Kallos, et al., "Inoculation and Growth Conditions for High-Cell-Density Expansion of mannalian Neural Stem Cells in Suspension Bioreactors," Bioengineering, 63:473-483 (1999).

Kashimada et al., "Sry: the master switch in mammalian sex determination," Development, vol. 137(23), pp. 3921-3930, Dec. 2, 2010.

Kato et al., "Production of Sry knockout mouse using TALEN via oocyte injection," Scientific Reports, vol. 3, p. 3136, 2013 (published Nov. 5, 2013).

Kuno et al., "Generation of fertile and fecund F0 XY female mice from XY ES cells," Transgenic Research, vol. 24(1), pp. 19-29, 2014 (epub Aug. 3, 2014).

Kuroiwa, et al., "Sequential targeting of the genes enclodiing immunoglobulin-μ and prion protein in cattle," Nature Genetics, vol. 36, No. 7, (Jul. 2004).

Li et al., "Germline Competent Embryonic Stem Cells Derived from Rat Blastocysts," Cell, vol. 135, pp. 1299-1310, 2008.

Li, et al., "Non-equivalence of cloned and clonal mice, Current Biology," R756-R757, vol. 15, No. 18 (Sep. 19, 2005).

Lin, S.-C., et al., "Strategies for gene disruption in *Drosophila*," Cell & Bioscience (2014), vol. 4(1), p. 63.

Lombardo, et al., "Gene editing in human stem cells using zinc finger nucleases and integrase-defective lentiviral vector delivery," Nature Biotechnology, 2007, vol. 25(11), pp. 1298-1306.

(56) References Cited

OTHER PUBLICATIONS

Lovell-Badge et al., "XY female mice resulting froma heritable mutation in the primary testis-determining Tdy," Development, Jul. 1, 1990, vol. 109:635-646.
MacDonald, et al., "Precise and in situ genetic humanization of 6 Mb of mouse immumnoglobulin genes," PNAS, vol. 111, No. 14: 5147-5152, (Apr. 8, 2014).
Mali et al., "RNA-Guided Human Genome Engineering via Cas9," Science, vol. 339(6121), pp. 823-826 plus Supplemental Materials, Jan. 3, 2013.
Mashimo et al., "Generation of knockout rats with X-linked severe combined immunodeficiency (X-SCID) using zinc finger nucleases," PLoS One, vol. 5(1), p. e8870, 2010.
Mazeyrat et al., "The mouse Y chromosome interval necessary for spermatogonial proliferation is gene dense with syntenic homology to the human AZFa region," Hum. Mol. Genet., vol. 7(11), pp. 1713-1724, 1998.
Narsinh, et al., "Gene Correction in Human Embryonic and Induced Pluripotent Stem Cells: Promise and Challenges Ahead", Molecular Therapy, vol. 18, No. 6, pp. 1061-1063, (Jun. 2010).
PCT International Preliminary Report on Patentability for application PCT/US2013/038165 dated Oct. 28, 2014.
PCT International Preliminary Report on Patentability for application PCT/US2014/034412 dated Oct. 30, 2015.
PCT International Search Report and Written Opinion of the International Searching Authority for application PCT/US2014/060788 dated Jan. 26, 2015.
PCT International Search Report for application PCT/US2015/034503 dated Sep. 8, 2015.
PCT Written Opinion of the International Searching Authority for application PCT/US2015/034503 dated Sep. 8, 2015.
PCT/US2011/039997 International Preliminary Report on Patentability and Written Opinion dated Dec. 14, 2012.
PCT/US2013/038165 International Search Report and Written Opinion dated Jul. 12, 2013.
PCT/US2014/034412 International Search Report and Written Opinion of the Searching Authority dated Oct. 9, 2014.
PCT/US2015/038001 Invitation of Pay Additional Fees mailed Nov. 13, 2015.
Peng, Y., et al., "Making designer mutants in model organisms," Development (2014), vol. 141, pp. 4042-4054.
Pirottin et al., "Transgenic engineering of male-specific muscular hypertrophy," Pros. Natl. Acad. Sci. U.S.A., vol. 102(18), pp. 6413-6418, 2005.
Porkka, et al., "Cloning and Characterization of a Novel Six-Transmembrane Protein STEAP2, Expressed in Normal and Malignant Prostate," Lab. Invest., 82:1573-1582 (2002).
Poueymirou et al., "F0 generation mice fully derived from gene-targeted embryonic stem cells allowing immediate analysis," Nature Biotechnology, Epub Dec. 24, 2006, vol. 25(1):91-99.
Rohozinski et al., "Successful targeting of mouse Y chromosome genes using a site-directed insertion vector," Genesis, vol. 32(1), pp. 1-7, 2002.
Sargent et al., "The critical region of overlap defining the AZFa male infertility interval of proximal Yq contains three transcribed sequences," J. Med. Genet., vol. 36(9), pp. 670-677, 1999.
Schwank, G., et al., "Functional Repair of CFTR by CRISPR/Cas9 in Intestinal Stem Cell Organoids of Cystic Fibrosis Patients," Cell Stem Cell (2013), vol. 13, pp. 653-658.
Stemgent Product Speciication Sheet, PD0325901, pp. 1-2 (2012).
Tang, et al., "A mouse knockout library for secreted and transmembrane proteins," Nature Biotechnology, 28:749-755 (2010).
Tong et al., "Generating gene knockout rats by homologous recombination in embryonic stem cells," Nature Protocols, vol. 6(6), pp. 827-844, 2011 (epub May 26, 2011).
Turner, "Meiotic sex chromosome inactivation," Development vol. 134(1), pp. 1823-1831, 2007.
U.S. Appl. No. 13/157,728 Advisory Action dated Apr. 30, 2013.
U.S. Appl. No. 13/157,728 Final Rejection dated Jan. 16, 2013.
U.S. Appl. No. 13/157,728 Non-Final Office Action dated Dec. 15, 2014.
U.S. Appl. No. 13/157,728 Non-Final Rejection dated Jul. 11, 2012.
U.S. Appl. No. 13/157,728, Notice of Allowance dated May 27, 2015.
U.S. Appl. No. 13/870,280 Final Rejection dated Oct. 15, 2015.
U.S. Appl. No. 13/870,280, Requirement for Restriction/Election dated Jul. 22, 2014.00000000.
U.S. Appl. No. 14/254,715 Final Office Action dated Nov. 30, 2015.
U.S. Appl. No. 14/254,715, Non-Final Office Action dated Aug. 12, 2015.
U.S. Appl. No. 14/314,866, Advisory Action dated Aug. 12, 2015.
U.S. Appl. No. 14/314,866, Non-Final Office Action dated Dec. 26, 2014.
U.S. Appl. No. 14/314,866, Non-Final Office Action dated Nov. 27, 2015.
U.S. Appl. No. 14/314,866, Requirement for Restriction/Election dated Sep. 22, 2014.
U.S. Appl. No. 14/314,866, Final Office Action dated Jun. 4, 2015.
U.S. Appl. No. 14/578,291, Non-Final Office Action dated Mar. 10, 2015.
U.S. Appl. No. 14/578,291, Notice of Allowance dated Aug. 26, 2015.
U.S. Appl. No. 13/870,280, Non-Final Office Action dated Mar. 13, 2015.
U.S. Appl. No. 14/254,715, Requirement for Restriction/Election dated Jun. 4, 2015.
U.S. Appl. No. 13/157,728 Restriction Requirement dated Apr. 25, 2012.
Vernet et al., "The expression of Y-linked Zfy2 in XY mouse oocytes leads to frequent meiosis 2 defects, a high incidence of subsequent early cleavage stage arrest and infertility," Development, vol. 141, pp. 855-866, 2014 (published Feb. 2014).
Wang et al., "One-Step Generation of Mice Carrying Mutations in Multiple Genes by CRISPR/Cas-Mediated Genome Engineering," Cell, vol. 153, pp. 910-918, 2013. (published May 2013).
Wang et al., "TALEN-mediated editing of the mouse Y chromosome," Nature Biotechnology, vol. 31(6), p. 530-532, 2013 (epub May 12, 2013).
Ward et al., "The 5T4 oncofoetal antigen is an early differentiation marker of mouse ES cells and its absence is a means to assess pluripotency," The Journal of Cell Science, vol. 116:4533-4542 (Nov. 15, 2003).
Wen et al., "Completely ES Cell-Derived Mice Produced by Tetraploid Complementation Using Inner Cell Mass (ICM) Deficient Blastocysts," PLoS One, vol. 9(4), e94730, Apr. 14, 2014.
Zhou, H., et al., "Large chromosomal deletions and heritable small genetic changes induced by CRISPR/Cas9 in rice," Nucleic Acids Research (2014), vol. 42(17), pp. 10903-10914.
Zhang et al., "The CRISPR/Cas9 system produces specific and homozygous targeted gene editing in rice in one generation," Plant Biotechnol. J., vol. 12(6), pp. 797-807, May 23, 2014.
Auerbach et al., "Establishment and chimera analysis of 129/SvEv- and C57BL/6-derived mouse embryonic stem cell lines," Biotechniques, vol. 29(5), pp. 1024-1028, 1030, 1032, Nov. 2000.
Bassing et al., "Increased ionizing radiation sensitivity and genomic instability in the absence of histone H2AX," Proc. Natl. Acad. Sci. U.S.A., vol. 99(12), pp. 8173-8178, 2002.
Benders et al., "Cloning whole bacterial genomes in yeast," Nucleic Acids Res., vol. 38(8), pp. 2558-2569, Mar. 7, 2010.
Bernardini et al., "Site-specific genetic engineering of the Anopheles gambiae Y chromosome," Proc. Natl. Acad. Sci. USA, vol. 111(21), pp. 7600-7605, May 12, 2014.
Choulika et al., "Induction of Homologous Recombination in Mammalian Chromosomes by Using the I-Scel System of Saccharomyces cerevisiae," Mol. Cell. Biol., vol. 15(4), pp. 1968-1973, 1995.
D'Aiuto et al., "Large-scale generation of human iPSC-derived neural stem cells/early neural progenitor cells and their neuronal differentiation," Organogenesis, vol. 10(4), pp. 365-377, Oct. 2, 2014.

(56) References Cited

OTHER PUBLICATIONS

Donoho et al., "Analysis of Gene Targeting and Intrachromosomal Homologous Recombination Stimulated by Genomic Double-Strand Breaks in Mouse Embryonic Stem Cells," Mol. Cell. Biol., vol. 18(7), pp. 4070-4078, 1998.

EP Application No. 14784879.0, Extended European Search Report dated Sep. 19, 2016.

Frendewey, "VelociGene: Large-scale Modification of Rodent Genomes," Wellcome Trust Advanced Course: Genetic Engineering of Mammalian Stem Cells, Mar. 13, 2014.

Frendewey, "VelociGene: Large-scale Modification of Rodent Genomes," Wellcome Trust Advanced Course: Genetic Engineering of Mammalian Stem Cells, Feb. 20, 2015.

Fujii et al., "Efficient generation of genome-modified mice via offset-nicking by CRISPR/Cas system," Biochemical and Biophysical Research Communications, vol. 445(4), pp. 791-794 plus Supplementary Information, Jan. 31, 2014.

Gratz et al., "Genome Engineering of Drosophila with the CRISPR/RNA-Guided Cas9 Nuclease," Genetics, vol. 194, pp. 1029-1035, 2013. (published May 2013).

Gratz et al., "Highly Specific and Efficient CRISPR/Cas9-Catalyzed Homology-Directed Repair in Drosophila," Genetics, vol. 196(4), pp. 961-971 plus Supporting Information, Jan. 29, 2014.

Hirano et al., "Human and Mouse Induced Pluripotent Stem Cells Are Differentially Reprogrammed in Response to Kinase Inhibitors," Stem Cells and Development, vol. 21(8), p. 1287-1298, May 20, 2012.

Jallepalli et al., "Securin is required for chromosomal stability in human cells," Cell, vol. 105(4), pp. 445-457, May 18, 2001.

Jao et al., "Efficient multiplex biallelic zebrafish genome editing using a CRISPR nuclease system," Proc. Natl. Acad. Sci. U.S.A., vol. 110(34), pp. 13904-13909 plus Supporting Information, Aug. 5, 2013.

Jasin, et al., "Repair of Strand Breaks by Homologous Recombination," Cold Spring Harb. Perspect. Biol., vol. 5(11), p. a012740, Nov. 1, 2013.

Konermann et al., "Genome-scale transcriptional activation by an engineered CRISPR-Cas9 complex," Nature, vol. 517(7536), pp. 583-588, published online Dec. 10, 2014.

Kuijpers et al., "One-step assembly and targeted integration of multigene constructs assisted by the I-SceI meganuclease in Saccharomyces cerevisiae," FEMS Yeast Res., vol. 13(8), pp. 769-781, Oct. 7, 2013.

Li et al., "Optimization of Genome Engineering Approaches with the CRISPR/Cas9 System," PLoS One, vol. 9(8), p. e105779, Aug. 28, 2014.

Liu et al., "A one-step cloning method for the construction of somatic cell gene targeting vectors: application to production of human knockout cell lines," BMC Biotechnol., vol. 12, p. 71, Oct. 9, 2012.

Mali et al., "CAS9 transcriptional activators for target specificity screening and paired nickases for cooperative genome engineering," Nature Biotechnology, vol. 31(9), pp. 833-838 plus Supplementary Information, Aug. 1, 2013.

Mali, et al., "Cas9 as a versatile tool for engineering biology," Nature Methods, vol. 10(10), pp. 957-963, 2013.

Mashiko et al., "Generation of mutant mice by pronuclear injection of circular plasmid expressing Cas9 and single guided RMA," Sci. Rep., vol. 3, p. 3355, Nov. 27, 2013.

Musser, "Rodent," Brittanica. Retrieved from the Internet May 31, 2016: http://www.brittanica.com/animal/rodent.

Novus Biologicals, LLC, "Novus Biologicals launches new v6.5 Mouse embryonic stem cells," Jun. 18, 2010 [Retrieved from the Internet Mar. 29, 2016: <http://www.novusbio.com/about/press-release/novus-biologicals-launches-new-v65-mouse-embryonic-stem-cells.

Parikh et al., "Detailed Phenotypic and Molecular Analyses of Genetically Modified Mice Generated by CRISPR-Cas9-Mediated Editing," PLoS One, vol. 10(1), p. e0116484, Jan. 14, 2015.

PCT International Preliminary Report on Patentability for application PCT/US2014/060788 dated Jun. 23, 2016.

PCT International Search Report and Written Opinion of the International Searching Authority for application PCT/US2015/038001 dated Feb. 25, 2016.

PCT International Search Report and Written Opinion of the International Searching Authority for application PCT/US2015/062023 dated May 13, 2016.

PCT International Search Report and Written Opinion of the International Searching Authority for application PCT/US2015/066681 dated Mar. 29, 2016.

PCT/US2015/062023 Invitation of Pay Additional Fees dated Feb. 8, 2016.

Port et al., "Optimized CRISPR/Cas tools for efficient germline and somatic genome engineering in Drosophila," Proc. Natl. Acad. Sci. U.S.A., vol. 111(29), pp. E2967-E2976 plus Supporting Information, Jul. 7, 2014.

Porteus, et al., "Gene targeting using zinc finger nucleases," Nature Biotechnology, vol. 23(8), pp. 967-973, 2005.

Quinn et al., "A Site-Specific, Single-Copy Transgenesis Strategy to Identify 5' Regulatory Sequences of the Mouse Testis-Determining Gene Sry," PLoS One, vol. 9(4), p. e94813, Apr. 2014.

Ran et al., "Double nicking by RNA-guided CRISPR Cas9 for enhanced genome editing specificity," Cell, vol. 154, pp. 1380-1389, 2013.

Ran et al., "Genome engineering using the CRISPR-Cas9 system," Nature Protocols, vol. 8(11), pp. 2281-2308, Oct. 24, 2013.

Ran et al., "In vivo genome editing using Staphylococcus aureus Cas9," Nature, vol. 520(7546), pp. 186-191, Apr. 1, 2015.

Rideout et al., "Generation of mice from wild-type and targeted ES cells by nuclear cloning," Nat. Genet., vol. 24(2), pp. 109-110, Feb. 2000.

Shan et al., "Targeted genome modification of crop plants using a CRISPR-Cas system," Nature Biotechnology, vol. 31(8), pp. 686-688, Aug. 1, 2013.

Turinetto et al., "High Basal γH2AX Levels Sustain Self-Renewal of Mouse Embryonic and Induced Pluripotent Stem Cells," Stem Cells, vol. 30(7), pp. 1414-1423, 2012.

U.S. Appl. No. 14/254,715, Final Office Action dated Sep. 19, 2016.

U.S. Appl. No. 14/254,715, Non-Final Office Action dated Apr. 21, 2016.

U.S. Appl. No. 14/314,866, Advisory Action dated Aug. 15, 2016.

U.S. Appl. No. 14/314,866, Final Office Action dated Apr. 26, 2016.

U.S. Appl. No. 14/314,866, Non-Final Office Action dated Sep. 19, 2016.

U.S. Appl. No. 14/515,503, Non-Final Office Action dated May 20, 2016.

U.S. Appl. No. 14/515,503, Notice of Allowance dated Sep. 23, 2016.

U.S. Appl. No. 14/515,503, Requirement for Restriction/Election dated Mar. 4, 2016.

U.S. Appl. No. 14/731,914, Requirement for Restriction/Election dated Dec. 31, 2015.

U.S. Appl. No. 14/731,914, Non-Final Office Action dated Jun. 17, 2016.

U.S. Appl. No. 14/926,773, Non-Final Office Action dated May 6, 2016.

U.S. Appl. No. 14/926,773, Requirement for Restriction/Election dated Feb. 16, 2016.

U.S. Appl. No. 14/928,180, Advisory Action dated Aug. 22, 2016.

U.S. Appl. No. 14/928,180, Final Office Action dated Jun. 6, 2016.

U.S. Appl. No. 15/189,767, Non-Final Office Action dated Aug. 26, 2016.

U.S. Appl. No. 13/870,280, Advisory Action dated Jan. 5, 2016.

U.S. Appl. No. 14/928,180, Non-Final Office Action dated Jan. 5, 2016.

Wang et al., "One-Step Generation of Mice Carrying Mutations in Multiple Genes by CRISPR/Cas-Mediated Genome Engineering," Cell, vol. 153, pp. 910-918 plus supplemental materials, 2013. (published May 2013).

Whitworth et al., "Use of the CRISPR/Cas9 System to Produce Genetically Engineered Pigs from In Vitro-Derived Oocytes and Embryos," Biology of Reproduction, vol. 91(3), p. 78, Aug. 6, 2014.

(56) References Cited

OTHER PUBLICATIONS

Yoshimi et al., "Allele-specific genome editing and correction of disease-associated phenotypes in rats using the CRISPR-Cas platform," Nature Communications, vol. 5, p. 4240 plus Supplementary Information, Jun. 26, 2014.
Yu et al., "Highly Efficient Genome Modifications Mediated by CRISPR/Cas9 in *Drosophila*," Genetics, vol. 195, pp. 289-291 plus supporting information, Sep. 2013.
Zhang et al., "Biallelic targeting of expressed genes in mouse embryonic stem cells using the Cas9 system," Methods, vol. 69(2), pp. 171-178, Jun. 12, 2014.
"129S6 Inbred," Taconic Biosciences, Inc. Web Site (2016). [Retrieved from the Internet Oct. 17, 2016: <URL: http://www.taconic.com/mouse-model/129s6>].
"Black 6 (B6NTac) Inbred," Taconic Biosciences, Inc. Web Site (2016). [Retrieved from the Internet Oct. 17, 2016: <URL: http://www.taconic.com/mouse-model/black-6-b6ntac>].
"Mouse Strain 129 Substrain Nomenclature", Mouse Genome Informatics Web Site (2016). [Retrieved from the Internet Oct. 17, 2016: <URL: http://www.informatics.jax.org/mgihome/nomen/strain_129.shtml>].
Abudayyeh et al., "C2c2 is a single-component programmable RNA-guided RNA-targeting CRISPR effector," Science, vol. 353(6299), Jun. 2, 2016.
Evers et al., "CRISPR knockout screening outperforms shRNA and CRISPRi in identifying essential genes," Nature Biotechnology, vol. 24(6), pp. 631-633, Apr. 25, 2016.
Gao et al., "DNA-guided genome editing using the Natronobacterium gregoryi Argonuate," Nature Biotechnology, vol. 34(7), pp. 768-773, May 2, 2016.
Komor et al, "Programmable editing of a target base in genomic DMA without double-stranded cleavage," Nature, vol. 533(7603), pp. 420-424, Apr. 20, 2016.
Morgens et al., "Systematic comparison of CRISPR/Cas9 and RNAi screens for essential genes," Nature Biotechnology, vol. 34(6), pp. 634-636, May 9, 2016.
PCT Written Opinion and International Preliminary Report on Patentability for application PCT/US2015/038001 dated Dec. 27, 2016.
Siao et al., "Single-step homozygous humanization induced by dual CRISPR/Cas9 cleavage," Oct. 28, 2015.
U.S. Appl. No. 14/926,773, Fnal Office Action dated Nov. 17, 2016.
Yamauchi et al., "Two genes substitute for the mouse Y chromosome for spermatogenesis and reproduction," Science, vol. 351(6272), pp. 514-516, Jan. 29, 2016.
Yoshimi et al., "ssODN-mediated knock-in with CRISPR-Cas for large genomic regions in zygotes," Nat. Commun., vol. 7, p. 10431, Jan. 20, 2016.
U.S. Appl. No. 14/926,773, Non-Final Office Action dated Jun. 2, 2017.

* cited by examiner

SEQUENCE LISTING

```
<160> NUMBER OF SEQ ID NOS: 73

<210> SEQ ID NO 1
<211> LENGTH: 23
<212> TYPE: DNA
<213> ORGANISM: Artificial Sequence
<220> FEATURE:
<223> OTHER INFORMATION: a target locus that is linked to a guide RNA
      (gRNA)
<220> FEATURE:
<221> NAME/KEY: misc_feature
<222> LOCATION: 2, 3, 4, 5, 6, 7, 8, 9, 10, 11, 12, 13, 14, 15, 16, 17,
      18, 19, 20, 21
<223> OTHER INFORMATION: n = A,T,C or G

<400> SEQUENCE: 1
gnnnnnnnnn nnnnnnnnnn ngg                                           23

<210> SEQ ID NO 2
<211> LENGTH: 80
<212> TYPE: RNA
<213> ORGANISM: Artificial Sequence
<220> FEATURE:
<223> OTHER INFORMATION: a guide RNA (gRNA)

<400> SEQUENCE: 2
guuuuagagc uagaaauagc aaguuaaaau aaggcuaguc cguuaucaac uugaaaaagu    60
ggcaccgagu cggugcuuuu                                               80

<210> SEQ ID NO 3
```

```
<211> LENGTH: 42
<212> TYPE: RNA
<213> ORGANISM: Artificial Sequence
<220> FEATURE:
<223> OTHER INFORMATION: a guide RNA (gRNA)

<400> SEQUENCE: 3
guuuuagagc uagaaauagc aaguuaaaau aaggcuaguc cg                           42

<210> SEQ ID NO 4
<211> LENGTH: 30
<212> TYPE: RNA
<213> ORGANISM: Artificial Sequence
<220> FEATURE:
<223> OTHER INFORMATION: a crRNA

<400> SEQUENCE: 4
guuuuagagc uagaaauagc aaguuaaaau                                        30

<210> SEQ ID NO 5
<211> LENGTH: 33
<212> TYPE: RNA
<213> ORGANISM: Artificial Sequence
<220> FEATURE:
<223> OTHER INFORMATION: a crRNA

<400> SEQUENCE: 5
guuuuagagc uagaaauagc aaguuaaaau aag                                    33

<210> SEQ ID NO 6
<211> LENGTH: 26
<212> TYPE: RNA
<213> ORGANISM: Artificial Sequence
<220> FEATURE:
<223> OTHER INFORMATION: a crRNA

<400> SEQUENCE: 6
gaguccgagc agaagaagaa guuuua                                            26

<210> SEQ ID NO 7
<211> LENGTH: 12
<212> TYPE: RNA
<213> ORGANISM: Artificial Sequence
<220> FEATURE:
<223> OTHER INFORMATION: a tracrRNA

<400> SEQUENCE: 7
aaggcuaguc cg                                                           12

<210> SEQ ID NO 8
<211> LENGTH: 50
<212> TYPE: RNA
<213> ORGANISM: Artificial Sequence
<220> FEATURE:
<223> OTHER INFORMATION: a tracrRNA

<400> SEQUENCE: 8
aaggcuaguc cguuaucaac uugaaaaagu ggcaccgagu cggugcuuuu                  50

<210> SEQ ID NO 9
<211> LENGTH: 23
<212> TYPE: DNA
<213> ORGANISM: Artificial Sequence
<220> FEATURE:
<223> OTHER INFORMATION: a target locus that is linked to a guide RNA
      (gRNA)
<220> FEATURE:
```

```
<221> NAME/KEY: misc_feature
<222> LOCATION: 2, 3, 4, 5, 6, 7, 8, 9, 10, 11, 12, 13, 14, 15, 16, 17,
      18, 19, 20, 21
<223> OTHER INFORMATION: n = A,T,C or G

<400> SEQUENCE: 9
gnnnnnnnnn nnnnnnnnnn ngg                                              23

<210> SEQ ID NO 10
<211> LENGTH: 23
<212> TYPE: DNA
<213> ORGANISM: Artificial Sequence
<220> FEATURE:
<223> OTHER INFORMATION: VG-1 gRNA target sequence

<400> SEQUENCE: 10
ccatgaatgc atttatggtg tgg                                              23

<210> SEQ ID NO 11
<211> LENGTH: 23
<212> TYPE: DNA
<213> ORGANISM: Artificial Sequence
<220> FEATURE:
<223> OTHER INFORMATION: VG-2 gRNA target sequence

<400> SEQUENCE: 11
ccgtggtgag aggcacaagt tgg                                              23

<210> SEQ ID NO 12
<211> LENGTH: 23
<212> TYPE: DNA
<213> ORGANISM: Artificial Sequence
<220> FEATURE:
<223> OTHER INFORMATION: VG-3 gRNA target sequence

<400> SEQUENCE: 12
gcaagcagct gggatgcagg tgg                                              23

<210> SEQ ID NO 13
<211> LENGTH: 20
<212> TYPE: DNA
<213> ORGANISM: Artificial Sequence
<220> FEATURE:
<223> OTHER INFORMATION: Synthetic sryTF1 primer

<400> SEQUENCE: 13
cgtggtgaga ggcacaagtt                                                  20

<210> SEQ ID NO 14
<211> LENGTH: 19
<212> TYPE: DNA
<213> ORGANISM: Artificial Sequence
<220> FEATURE:
<223> OTHER INFORMATION: Synthetic sryTR1 primer

<400> SEQUENCE: 14
gagatcagca agcagctgg                                                   19

<210> SEQ ID NO 15
<211> LENGTH: 22
<212> TYPE: DNA
<213> ORGANISM: Artificial Sequence
<220> FEATURE:
<223> OTHER INFORMATION: Synthetic sryTP1 probe

<400> SEQUENCE: 15
```
cccagcagaa tcccagcatg ca                                            22

<210> SEQ ID NO 16
<211> LENGTH: 18
<212> TYPE: DNA
<213> ORGANISM: Artificial Sequence
<220> FEATURE:
<223> OTHER INFORMATION: Synthetic sryTF2 primer

<400> SEQUENCE: 16
tggagggcca tgtcaagc                                                 18

<210> SEQ ID NO 17
<211> LENGTH: 18
<212> TYPE: DNA
<213> ORGANISM: Artificial Sequence
<220> FEATURE:
<223> OTHER INFORMATION: Synthetic sryTR2 primer

<400> SEQUENCE: 17
acaagttggc ccagcaga                                                 18

<210> SEQ ID NO 18
<211> LENGTH: 26
<212> TYPE: DNA
<213> ORGANISM: Artificial Sequence
<220> FEATURE:
<223> OTHER INFORMATION: Synthetic sryTP2 probe

<400> SEQUENCE: 18
tgaatgcatt tatggtgtgg tcccgt                                        26

<210> SEQ ID NO 19
<211> LENGTH: 20
<212> TYPE: DNA
<213> ORGANISM: Artificial Sequence
<220> FEATURE:
<223> OTHER INFORMATION: Synthetic sryTF3 primer

<400> SEQUENCE: 19
atgaatgcat ttatggtgtg                                               20

<210> SEQ ID NO 20
<211> LENGTH: 18
<212> TYPE: DNA
<213> ORGANISM: Artificial Sequence
<220> FEATURE:
<223> OTHER INFORMATION: Synthetic sryTR3 primer

<400> SEQUENCE: 20
aggtggaaaa gccttaca                                                 18

<210> SEQ ID NO 21
<211> LENGTH: 23
<212> TYPE: DNA
<213> ORGANISM: Artificial Sequence
<220> FEATURE:
<223> OTHER INFORMATION: Synthetic sryTP3 probe

<400> SEQUENCE: 21
ccgtggtgag aggcacaagt tgg                                           23

<210> SEQ ID NO 22
<211> LENGTH: 19
<212> TYPE: DNA
<213> ORGANISM: Artificial Sequence

```
<220> FEATURE:
<223> OTHER INFORMATION: Synthetic sryTF4 primer

<400> SEQUENCE: 22
gtgtggtccc gtggtgaga                                              19

<210> SEQ ID NO 23
<211> LENGTH: 20
<212> TYPE: DNA
<213> ORGANISM: Artificial Sequence
<220> FEATURE:
<223> OTHER INFORMATION: Synthetic sryTR4 primer

<400> SEQUENCE: 23
agatcagcaa gcagctggga                                             20

<210> SEQ ID NO 24
<211> LENGTH: 24
<212> TYPE: DNA
<213> ORGANISM: Artificial Sequence
<220> FEATURE:
<223> OTHER INFORMATION: Synthetic sryTP4 probe

<400> SEQUENCE: 24
aagttggccc agcagaatcc cagc                                        24

<210> SEQ ID NO 25
<211> LENGTH: 24
<212> TYPE: DNA
<213> ORGANISM: Artificial Sequence
<220> FEATURE:
<223> OTHER INFORMATION: Synthetic sryTF5 primer

<400> SEQUENCE: 25
catgcaaaat acagagatca gcaa                                        24

<210> SEQ ID NO 26
<211> LENGTH: 14
<212> TYPE: DNA
<213> ORGANISM: Artificial Sequence
<220> FEATURE:
<223> OTHER INFORMATION: Synthetic sryTR5 primer

<400> SEQUENCE: 26
ggaaaagcct taca                                                   14

<210> SEQ ID NO 27
<211> LENGTH: 15
<212> TYPE: DNA
<213> ORGANISM: Artificial Sequence
<220> FEATURE:
<223> OTHER INFORMATION: Synthetic sryTP5 probe

<400> SEQUENCE: 27
cagctgggat gcagg                                                  15

<210> SEQ ID NO 28
<211> LENGTH: 20
<212> TYPE: DNA
<213> ORGANISM: Artificial Sequence
<220> FEATURE:
<223> OTHER INFORMATION: Synthetic 648TUF primer

<400> SEQUENCE: 28
gatcagcaag cagctgggat                                             20
```

-continued

```
<210> SEQ ID NO 29
<211> LENGTH: 19
<212> TYPE: DNA
<213> ORGANISM: Artificial Sequence
<220> FEATURE:
<223> OTHER INFORMATION: Synthetic 648TUP probe

<400> SEQUENCE: 29
caggtggaaa agccttaca                                                    19

<210> SEQ ID NO 30
<211> LENGTH: 73
<212> TYPE: DNA
<213> ORGANISM: Artificial Sequence
<220> FEATURE:
<223> OTHER INFORMATION: Synthetic

<400> SEQUENCE: 30
aattaccaca tcttttgcct attgccaccg cttgaggagt tgttggagaa gtctcattgg       60
aagaatcaga tga                                                          73

<210> SEQ ID NO 31
<211> LENGTH: 65
<212> TYPE: DNA
<213> ORGANISM: Artificial Sequence
<220> FEATURE:
<223> OTHER INFORMATION: Synthetic

<400> SEQUENCE: 31
aattaccaca tcttttgcc tattgtccaa atactggaga agtctcattg caacgaatca        60
gatga                                                                   65

<210> SEQ ID NO 32
<211> LENGTH: 63
<212> TYPE: DNA
<213> ORGANISM: Artificial Sequence
<220> FEATURE:
<223> OTHER INFORMATION: Synthetic

<400> SEQUENCE: 32
aattaccaca tcttttgcct attgacaaaa tgttggagaa gtctcatggg aagaatcaaa       60
ttg                                                                     63

<210> SEQ ID NO 33
<211> LENGTH: 90
<212> TYPE: DNA
<213> ORGANISM: Artificial Sequence
<220> FEATURE:
<223> OTHER INFORMATION: Synthetic

<400> SEQUENCE: 33
ctatcagata ggatatttta gagttttcat attgtatgga ggagttgttg gagaagtctc       60
attggaagaa tcagatgatg agatcttaat                                        90

<210> SEQ ID NO 34
<211> LENGTH: 69
<212> TYPE: DNA
<213> ORGANISM: Artificial Sequence
<220> FEATURE:
<223> OTHER INFORMATION: Synthetic

<400> SEQUENCE: 34
ctatcagata ggatatttta gagttgttgg agaagtctca ttggaagaat cagatgatga      60
``` gatcttaat                                                                69

<210> SEQ ID NO 35
<211> LENGTH: 69
<212> TYPE: DNA
<213> ORGANISM: Artificial Sequence
<220> FEATURE:
<223> OTHER INFORMATION: Synthetic

<400> SEQUENCE: 35
ctatcagata ggatatttta gagttgttgg agaagtctca ttggaagaat cagatgatga      60
gatcttaat                                                             69

<210> SEQ ID NO 36
<211> LENGTH: 69
<212> TYPE: DNA
<213> ORGANISM: Artificial Sequence
<220> FEATURE:
<223> OTHER INFORMATION: Synthetic

<400> SEQUENCE: 36
ctatcacata ggatatttta gagttgttgg cgaagtctca ttggaagaat cagatgatga      60
gatcttaat                                                             69

<210> SEQ ID NO 37
<211> LENGTH: 69
<212> TYPE: DNA
<213> ORGANISM: Artificial Sequence
<220> FEATURE:
<223> OTHER INFORMATION: Synthetic

<400> SEQUENCE: 37
tcagatagga tattttagag ttttcatatt gtatggttat aggaggagtt gttggagaag      60
tctcattgg                                                             69

<210> SEQ ID NO 38
<211> LENGTH: 49
<212> TYPE: DNA
<213> ORGANISM: Artificial Sequence
<220> FEATURE:
<223> OTHER INFORMATION: Synthetic

<400> SEQUENCE: 38
tcagatagga tattttagag ttttcatatt gttggagaag tctcattgg                 49

<210> SEQ ID NO 39
<211> LENGTH: 49
<212> TYPE: DNA
<213> ORGANISM: Artificial Sequence
<220> FEATURE:
<223> OTHER INFORMATION: Synthetic

<400> SEQUENCE: 39
tcagataggg tattttagag ttttcatatt gttggagaag tctcatggg                 49

<210> SEQ ID NO 40
<211> LENGTH: 49
<212> TYPE: DNA
<213> ORGANISM: Artificial Sequence
<220> FEATURE:
<223> OTHER INFORMATION: Synthetic

<400> SEQUENCE: 40

```
tcccatagga tattttagag ttctcatatt gctgccgaag tctcattgc        49

<210> SEQ ID NO 41
<211> LENGTH: 39
<212> TYPE: DNA
<213> ORGANISM: Artificial Sequence
<220> FEATURE:
<223> OTHER INFORMATION: Synthetic

<400> SEQUENCE: 41
ttttagagtt tttcatattg ttgggagaag tctcattgg                   39

<210> SEQ ID NO 42
<211> LENGTH: 28
<212> TYPE: DNA
<213> ORGANISM: Artificial Sequence
<220> FEATURE:
<223> OTHER INFORMATION: Synthetic KDM5D ZFN1 target sequence

<400> SEQUENCE: 42
ttaggtaggt agacagggat gttttctg                               28

<210> SEQ ID NO 43
<211> LENGTH: 28
<212> TYPE: DNA
<213> ORGANISM: Artificial Sequence
<220> FEATURE:
<223> OTHER INFORMATION: Synthetic KDM5D ZFN2 target sequence

<400> SEQUENCE: 43
atccagtctc tgaaggaagc tctgacta                               28

<210> SEQ ID NO 44
<211> LENGTH: 28
<212> TYPE: DNA
<213> ORGANISM: Artificial Sequence
<220> FEATURE:
<223> OTHER INFORMATION: Synthetic KDM5D ZFN3 target sequence

<400> SEQUENCE: 44
caaaagcttc aggggactc ttacactc                                28

<210> SEQ ID NO 45
<211> LENGTH: 28
<212> TYPE: DNA
<213> ORGANISM: Artificial Sequence
<220> FEATURE:
<223> OTHER INFORMATION: Synthetic KDM5D ZFN4 target sequence

<400> SEQUENCE: 45
tttgagcagg ctacacagga gtatactt                               28

<210> SEQ ID NO 46
<211> LENGTH: 28
<212> TYPE: DNA
<213> ORGANISM: Artificial Sequence
<220> FEATURE:
<223> OTHER INFORMATION: Synthetic KDM5D ZFN5 target sequence

<400> SEQUENCE: 46
aagcggtggc aataggcaaa agatgtgg                               28

<210> SEQ ID NO 47
<211> LENGTH: 28
<212> TYPE: DNA
<213> ORGANISM: Artificial Sequence
```

```
<220> FEATURE:
<223> OTHER INFORMATION: Synthetic KDM5D ZFN6 target sequence

<400> SEQUENCE: 47
ctgaagtccc caagggagta tggagatg                                      28

<210> SEQ ID NO 48
<211> LENGTH: 28
<212> TYPE: DNA
<213> ORGANISM: Artificial Sequence
<220> FEATURE:
<223> OTHER INFORMATION: Synthetic KDM5D ZFN7 target sequence

<400> SEQUENCE: 48
agaaagcggt ggcaataggc aaaagatg                                      28

<210> SEQ ID NO 49
<211> LENGTH: 28
<212> TYPE: DNA
<213> ORGANISM: Artificial Sequence
<220> FEATURE:
<223> OTHER INFORMATION: Synthetic KDM5D ZFN8 target sequence

<400> SEQUENCE: 49
aagtccccaa gggagtatgg agatgccc                                      28

<210> SEQ ID NO 50
<211> LENGTH: 28
<212> TYPE: DNA
<213> ORGANISM: Artificial Sequence
<220> FEATURE:
<223> OTHER INFORMATION: Synthetic DDX3Y ZFN1 target sequence

<400> SEQUENCE: 50
actccaacga ctatgaccac tccgttca                                      28

<210> SEQ ID NO 51
<211> LENGTH: 28
<212> TYPE: DNA
<213> ORGANISM: Artificial Sequence
<220> FEATURE:
<223> OTHER INFORMATION: Synthetic DDX3Y ZFN2 target sequence

<400> SEQUENCE: 51
acagatcaga tgaagatgac tggtcaaa                                      28

<210> SEQ ID NO 52
<211> LENGTH: 28
<212> TYPE: DNA
<213> ORGANISM: Artificial Sequence
<220> FEATURE:
<223> OTHER INFORMATION: Synthetic DDX3Y ZFN3 target sequence

<400> SEQUENCE: 52
ctttcaagga aaaaagaac aaaaccca                                       28

<210> SEQ ID NO 53
<211> LENGTH: 28
<212> TYPE: DNA
<213> ORGANISM: Artificial Sequence
<220> FEATURE:
<223> OTHER INFORMATION: Synthetic DDX3Y ZFN4 target sequence

<400> SEQUENCE: 53
ggtctgtgat aaggacagtt caggatgg                                      28
```

```
<210> SEQ ID NO 54
<211> LENGTH: 28
<212> TYPE: DNA
<213> ORGANISM: Artificial Sequence
<220> FEATURE:
<223> OTHER INFORMATION: Synthetic DDX3Y ZFN5 target sequence

<400> SEQUENCE: 54
taaatctgac tgagaatggg tagtagaa                                          28

<210> SEQ ID NO 55
<211> LENGTH: 28
<212> TYPE: DNA
<213> ORGANISM: Artificial Sequence
<220> FEATURE:
<223> OTHER INFORMATION: Synthetic DDX3Y ZFN6 target sequence

<400> SEQUENCE: 55
cagatggtcc aggagaggct ttgaaggc                                          28

<210> SEQ ID NO 56
<211> LENGTH: 28
<212> TYPE: DNA
<213> ORGANISM: Artificial Sequence
<220> FEATURE:
<223> OTHER INFORMATION: Synthetic DDX3Y ZFN7 target sequence

<400> SEQUENCE: 56
attgggcttc cctctggaat cacgagat                                          28

<210> SEQ ID NO 57
<211> LENGTH: 28
<212> TYPE: DNA
<213> ORGANISM: Artificial Sequence
<220> FEATURE:
<223> OTHER INFORMATION: Synthetic DDX3Y ZFN8 target sequence

<400> SEQUENCE: 57
tttcagtgat cgtggaagtg gatccagg                                          28

<210> SEQ ID NO 58
<211> LENGTH: 28
<212> TYPE: DNA
<213> ORGANISM: Artificial Sequence
<220> FEATURE:
<223> OTHER INFORMATION: Synthetic USP9Y ZFN1 target sequence

<400> SEQUENCE: 58
ctggtttgga aatcgtactg taaaagac                                          28

<210> SEQ ID NO 59
<211> LENGTH: 28
<212> TYPE: DNA
<213> ORGANISM: Artificial Sequence
<220> FEATURE:
<223> OTHER INFORMATION: Synthetic USP9Y ZFN2 target sequence

<400> SEQUENCE: 59
gcaaagaggt tgaggatttg gacatatt                                          28

<210> SEQ ID NO 60
<211> LENGTH: 28
<212> TYPE: DNA
<213> ORGANISM: Artificial Sequence
<220> FEATURE:
<223> OTHER INFORMATION: Synthetic USP9Y ZFN3 target sequence
```

-continued

```
<400> SEQUENCE: 60
gaggagttgt tggagaagtc tcattgga                                        28

<210> SEQ ID NO 61
<211> LENGTH: 28
<212> TYPE: DNA
<213> ORGANISM: Artificial Sequence
<220> FEATURE:
<223> OTHER INFORMATION: Synthetic USP9Y ZFN4 target sequence

<400> SEQUENCE: 61
atatgaacaa ggccaaggtg atgctcca                                        28

<210> SEQ ID NO 62
<211> LENGTH: 28
<212> TYPE: DNA
<213> ORGANISM: Artificial Sequence
<220> FEATURE:
<223> OTHER INFORMATION: Synthetic USP9Y ZFN5 target sequence

<400> SEQUENCE: 62
actcagaaga aggattagga atgctttg                                        28

<210> SEQ ID NO 63
<211> LENGTH: 28
<212> TYPE: DNA
<213> ORGANISM: Artificial Sequence
<220> FEATURE:
<223> OTHER INFORMATION: Synthetic USP9Y ZFN6 target sequence

<400> SEQUENCE: 63
atgcttagaa atgtatcagt tcatcttg                                        28

<210> SEQ ID NO 64
<211> LENGTH: 28
<212> TYPE: DNA
<213> ORGANISM: Artificial Sequence
<220> FEATURE:
<223> OTHER INFORMATION: Synthetic USP9Y ZFN7 target sequence

<400> SEQUENCE: 64
tccataagga ttttggaaaa agacacag                                        28

<210> SEQ ID NO 65
<211> LENGTH: 28
<212> TYPE: DNA
<213> ORGANISM: Artificial Sequence
<220> FEATURE:
<223> OTHER INFORMATION: Synthetic USP9Y ZFN8 target sequence

<400> SEQUENCE: 65
aggctgtgag tggatggaag tttgaaat                                        28

<210> SEQ ID NO 66
<211> LENGTH: 20
<212> TYPE: RNA
<213> ORGANISM: Artificial Sequence
<220> FEATURE:
<223> OTHER INFORMATION: Synthetic Kdm5dgA gRNA 1

<400> SEQUENCE: 66
uuugccgaau augcucucgu                                                 20

<210> SEQ ID NO 67
```

```
<211> LENGTH: 20
<212> TYPE: RNA
<213> ORGANISM: Artificial Sequence
<220> FEATURE:
<223> OTHER INFORMATION: Synthetic Kdm5dgB gRNA 2

<400> SEQUENCE: 67
uugccgaaua ugcucucgug                                              20

<210> SEQ ID NO 68
<211> LENGTH: 20
<212> TYPE: RNA
<213> ORGANISM: Artificial Sequence
<220> FEATURE:
<223> OTHER INFORMATION: Synthetic Kdm5dgC gRNA 5

<400> SEQUENCE: 68
cgggcaucuc cauacucccu                                              20

<210> SEQ ID NO 69
<211> LENGTH: 20
<212> TYPE: RNA
<213> ORGANISM: Artificial Sequence
<220> FEATURE:
<223> OTHER INFORMATION: Synthetic Usp9ygA gRNA 1

<400> SEQUENCE: 69
uagcucguug uguagcaccu                                              20

<210> SEQ ID NO 70
<211> LENGTH: 20
<212> TYPE: RNA
<213> ORGANISM: Artificial Sequence
<220> FEATURE:
<223> OTHER INFORMATION: Synthetic Usp9ygB gRNA 1

<400> SEQUENCE: 70
uauaguuucu ucgggguaac                                              20

<210> SEQ ID NO 71
<211> LENGTH: 20
<212> TYPE: RNA
<213> ORGANISM: Artificial Sequence
<220> FEATURE:
<223> OTHER INFORMATION: Synthetic Usp9ygC gRNA 2

<400> SEQUENCE: 71 ggaucccuu cuauaggccc                                               20

<210> SEQ ID NO 72
<211> LENGTH: 18
<212> TYPE: DNA
<213> ORGANISM: Artificial Sequence
<220> FEATURE:
<223> OTHER INFORMATION: Synthetic HMG box DNA binding motif upstream
      recognition sequence

<400> SEQUENCE: 72
tcccgtggtg agaggcac                                                18

<210> SEQ ID NO 73
<211> LENGTH: 18
<212> TYPE: DNA
```

```
<213> ORGANISM: Artificial Sequence
<220> FEATURE:
<223> OTHER INFORMATION: Synthetic HMG box DNA binding motif downstream
      recognition sequence

<400> SEQUENCE: 73
tattttgcat gctgggat                                                    18
```

METHODS FOR PRODUCING A MOUSE XY EMBRYONIC (ES) CELL LINE CAPABLE OF PRODUCING A FERTILE XY FEMALE MOUSE IN AN F0 GENERATION

CROSS-REFERENCE TO RELATED APPLICATIONS

This application claims the benefit of U.S. Provisional Application No. 62/017,582, filed Jun. 26, 2014, and of U.S. Provisional Application No. 62/017,627, filed Jun. 26, 2014, each of which is hereby incorporated herein in its entirety by reference.

REFERENCE TO A SEQUENCE LISTING SUBMITTED AS A TEXT FILE VIA EFS WEB

This application includes an electronic sequence listing in a file named 463014_SEQLIST.TXT, created Oct. 29, 2015, and containing 15,080 bytes, which is hereby incorporated by reference in its entirety for all purposes.

FIELD

The invention relates to the methods and compositions for maintaining or culturing pluripotent and/or totipotent cells and methods and compositions for generating cell populations and transgenic animals.

BACKGROUND

Perhaps due to unique structural features of the Y chromosome, conventional gene targeting strategies in mouse embryonic stem cells to generate mutations on the Y-linked genes have had limited success. Therefore, often the understanding of the functions of murine P-linked genes is limited to insights gained from studies of mice that carry spontaneous deletions, random gene traps insertions or autosomal transgenes. Methods are needed to improve the ability to target a genomic locus on the Y chromosome.

The Sry protein (sex-determining region Y) is the key regulator of male sex determination in placental mammals. The Sry gene, also known as the Testis Determining Factor (TDF), resides on the Y chromosome. Sry is thought to be a transcription factor that binds DNA through its High Mobility Group (HMG) domain. Expression of the mouse Sry gene is restricted to the genital ridge in a narrow time window around day 11 of embryonic development; both Sry mRNA and protein are detected. Sufficient Sry must be made within this time window to convert the bipotential genital ridge toward the male testis forming program while inhibiting the female program of ovary development. In adult testes a circular Sry transcript is detected but not the Sry protein. Mutations in the Sry gene that cause the production of an inactive Sry protein or that alter the timing and strength of gene expression can cause male to female sex reversal, resulting in animals that have an X and a Y chromosome but are anatomically female. So-called XY females are often sterile or have a low fertility. Being able to control sex determination by regulation of the Sry would have great value in the production of genetically modified animals.

SUMMARY

A method for making an XY embryonic stem (ES) cell line capable of producing a fertile XY female non-human mammal in an F0 generation is provided. The method comprises: (a) modifying a non-human mammalian XY embryonic stem (ES) cell to have a modification that decreases the level and/or activity of an Sry protein; and, (b) culturing the modified ES cell line under conditions that allow for making an ES cell line capable of producing a fertile XY female non-human mammal in an F0 generation.

A method for making a fertile XY female non-human mammal in an F0 generation is also provided. The method comprises: (a) introducing the non-human mammalian XY ES cell made by the above method having a modification that decreases the level and/or activity of an Sry protein into a host embryo; (b) gestating the host embryo; and, (c) obtaining an F0 XY female non-human mammal, wherein upon attaining sexual maturity the F0 XY female non-human mammal is fertile. In one embodiment, the female XY F0 non-human mammal is fertile when crossed to a wild type mouse. In specific embodiments, the wild type mouse is C57BL/6.

In one embodiment, the non-human mammalian XY ES cell is from a rodent. In a specific embodiment, the rodent is a mouse. In one embodiment, the mouse XY ES cell is derived from a 129 strain. In one embodiment, the mouse XY ES cell is a VGF1 mouse ES cell. In one embodiment, the mouse XY ES cell comprises a Y chromosome derived from the 129 strain. In one embodiment, the mouse XY ES cell is from a C57BL/6 strain. In another embodiment the rodent is a rat or a hamster.

In some embodiments, the decreased level and/or activity of the Sry protein results from a genetic modification in the Sry gene. In some such methods, the genetic modification in the Sry gene comprises an insertion of one or more nucleotides, a deletion of one or more nucleotides, a substitution of one or more nucleotides, a knockout, a knockin, a replacement of an endogenous nucleic acid sequence with a homologous, heterologous, or orthologous nucleic acid sequence, or a combination thereof.

In the methods provided herein, the targeted genetic modification can comprises an insertion, a deletion, a knockout, a knockin, a point mutation, or a combination thereof. In another embodiment, the targeted genetic modification is on an autosome.

In some embodiments, the modification of the Sry gene comprises an insertion of a selectable marker and/or a reporter gene operably linked to a promoter active in the non-human mammalian ES cell. In some embodiments, the modification of the Sry gene comprises an insertion of a reporter gene operably linked to the endogenous Sry promoter. In a specific embodiment, the reporter gene encodes the reporter protein LacZ.

In one embodiment, the culturing step comprises culturing the non-human mammalian XY ES cell in a medium comprising a base medium and supplements suitable for maintaining the non-human mammalian ES cell in culture, wherein the medium is a low-osmolality medium. In one embodiment, the low-osmolality medium exhibits an osmolality from about 200 mOsm/kg to less than about 329 mOsm/kg. In other embodiments the low-osmolality medium exhibits one or more of the following characteristic: a conductivity of about 11 mS/cm to about 13 mS/cm; a salt of an alkaline metal and a halide in a concentration of about 50 mM to about 110 mM; a carbonic acid salt concentration of about 17 mM to about 30 mM; a total alkaline metal halide salt and carbonic acid salt concentration of about 85 mM to about 130 mM; and/or a combination of any two or more thereof.

In some embodiments, upon introduction of the non-human mammalian XY ES cells into a host embryo and following gestation of the host embryo, at least 80%, at least 85%, at least 90%, or at least 95% of the F0 non-human mammals are XY females which upon attaining sexual maturity the F0 XY female non-human mammal is fertile.

In one embodiment, the non-human mammalian XY ES cell comprises a target genomic locus on the Y chromosome comprising a recognition site for a nuclease agent, and wherein the nuclease agent induces a nick or double-strand break at the recognition site. Such a method can further comprise exposing the ES cell to the nuclease agent in the presence of a targeting vector comprising an insert polynucleotide, wherein following exposure to the nuclease agent and the targeting vector, the ES cell is modified to contain the insert polynucleotide. In one embodiment, the nuclease agent is an mRNA encoding a nuclease. In specific embodiments, the nuclease agent is (a) a zinc finger nuclease (ZFN); (b) is a Transcription Activator-Like Effector Nuclease (TALEN); or (c) a meganuclease. In other embodiments, the nuclease agent comprises a Clustered Regularly Interspaced Short Palindromic Repeats (CRISPR)-associated (Cas) protein and a guide RNA (gRNA). In such methods, the guide RNA (gRNA) comprises (a) a Clustered Regularly Interspaced Short Palindromic Repeats (CRISPR) RNA (crRNA) that targets the first recognition site; and (b) a trans-activating CRISPR RNA (tracrRNA). In some cases, the recognition site is immediately flanked by a Protospacer Adjacent Motif (PAM) sequence. In one embodiment, the Cas protein is Cas9.

Also provided is an in vitro culture comprising the non-human mammalian XY ES cell line according to any of the methods provided herein.

An in vitro culture is provided and comprises (a) a non-human mammalian XY embryonic stem (ES) cell having a modification that decreases the level and/or activity of an Sry protein; and, (b) a medium comprising a base medium and supplements suitable for maintaining the non-human mammalian ES cell in culture. In one embodiment, the base medium exhibits an osmolality from about 200 mOsm/kg to less than about 329 mOsm/kg. In other embodiments, the base medium exhibits one or more of the following characteristic: a conductivity of about 11 mS/cm to about 13 mS/cm; a salt of an alkaline metal and a halide in a concentration of about 50 mM to about 110 mM; a carbonic acid salt concentration of about 17 mM to about 30 mM; a total alkaline metal halide salt and carbonic acid salt concentration of about 85 mM to about 130 mM; and/or a combination of any two or more thereof. In one embodiment, the non-human mammalian XY ES cell is from a rodent. In one embodiment, the rodent is a mouse or a rat. In one embodiment, the mouse XY ES cell is a VGF1 mouse ES cell. In one embodiment, the rodent is a rat or a hamster. In one embodiment, the decreased level and/or activity of the Sry protein is from a genetic modification in the Sry gene. In one embodiment, the genetic modification in the Sry gene comprises an insertion of one or more nucleotides, a deletion of one or more nucleotides, a substitution of one or more nucleotides, a knockout, a knockin, a replacement of an endogenous nucleic acid sequence with a heterologous nucleic acid sequence or a combination thereof. In one embodiment, the non-human mammalian ES cell comprises one, two, three or more targeted genetic modifications. In one embodiment, the targeted genetic modification comprises an insertion, a deletion, a knockout, a knockin, a point mutation, or a combination thereof. In one embodiment, the targeted genetic modification comprises at least one insertion of a heterologous polynucleotide into the genome of the XY ES cell. In one embodiment, the targeted genetic modification is on an autosome. In one embodiment, the base medium exhibits 50±5 mM NaCl, 26±5 mM carbonate, and 218±22 mOsm/kg. In one embodiment, the base medium exhibits about 3 mg/mL NaCl, 2.2 mg/mL sodium bicarbonate, and 218 mOsm/kg. In one embodiment, the base medium exhibits 87±5 mM NaCl, 18±5 mM carbonate, and 261±26 mOsm/kg. In one embodiment, the base medium exhibits about 5.1 mg/mL NaCl, 1.5 mg/mL sodium bicarbonate, and 261 mOsm/kg. In one embodiment, the base medium exhibits 110±5 mM NaCl, 18±5 mM carbonate, and 294±29 mOsm/kg. In one embodiment, the base medium exhibits about 6.4 mg/mL NaCl, 1.5 mg/mL sodium bicarbonate, and 294 mOsm/kg. In one embodiment, the base medium exhibits 87±5 mM NaCl, 26±5 mM carbonate, and 270±27 mOsm/kg. In one embodiment, the base medium exhibits about 5.1 mg/mL NaCl, 2.2 mg/mL sodium bicarbonate, and 270 mOsm/kg. In one embodiment, the base medium exhibits 87±5 mM NaCl, 26±5 mM carbonate, 86±5 mM glucose, and 322±32 mOsm/kg. In one embodiment, the base medium exhibits about 5.1 mg/mL NaCl, 2.2 mg/mL sodium bicarbonate, 15.5 mg/mL glucose, and 322 mOsm/kg. In one embodiment, upon introduction of the non-human mammalian XY ES cells into a host embryo and following gestation of the host embryo, at least 80% of the F0 non-human mammals are XY females which upon attaining sexual maturity the F0 XY female non-human mammal is fertile.

Further provided is a method for making a fertile female XY non-human mammal in an F0 generation, comprising: (a) culturing a donor non-human mammalian XY embryonic stem (ES) cell having a modification that decreases the level and/or activity of an Sry protein in a medium comprising a base medium and supplements suitable for maintaining the non-human mammalian ES cell in culture, (b) introducing the donor XY non-human mammalian ES cell into a host embryo; (c) gestating the host embryo; and, (d) obtaining an F0 XY female non-human mammal, wherein upon attaining sexual maturity the F0 XY female non-human mammal is fertile. In one embodiment, the medium exhibits an osmolality from about 200 mOsm/kg to less than about 329 mOsm/kg. In other embodiments, the medium exhibits a characteristic comprising one or more of the following: a conductivity of about 11 mS/cm to about 13 mS/cm; a salt of an alkaline metal and a halide in a concentration of about 50 mM to about 110 mM; a carbonic acid salt concentration of about 17 mM to about 30 mM; a total alkaline metal halide salt and carbonic acid salt concentration of about 85 mM to about 130 mM; and/or a combination of any two or more thereof; In one embodiment, the non-human mammalian XY ES cell is from a rodent. In one embodiment, the rodent is a mouse or a rat. In one embodiment, the mouse XY ES cell is a VGF1 mouse ES cell. In one embodiment, the rodent is a rat or a hamster. In one embodiment, the decreased level and/or activity of the Sry protein is from a genetic modification in the Sry gene. In one embodiment, the genetic modification in the Sry gene comprises an insertion of one or more nucleotides, a deletion of one or more nucleotides, a substitution of one or more nucleotides, a knockout, a knockin, a replacement of an endogenous nucleic acid sequence with a heterologous nucleic acid sequence or a combination thereof. In one embodiment, the non-human mammalian ES cell comprises one, two, three or more targeted genetic modifications. In one embodiment, the targeted genetic modification comprises an insertion, a deletion, a knockout, a knockin, a point mutation, or a combination thereof. In one embodiment, the targeted genetic modification comprises at least one insertion of a heterologous polynucleotide into a genome of the XY ES cell. In one embodiment, the targeted genetic modification is on an autosome. In one embodiment, the base medium exhibits 50±5 mM NaCl, 26±5 mM carbonate, and 218±22 mOsm/kg. In one embodiment, the base medium exhibits about 3 mg/mL NaCl, 2.2 mg/mL sodium bicarbonate, and 218 mOsm/kg. In one embodiment, the base medium exhibits 87±5 mM NaCl, 18±5 mM carbonate, and 261±26 mOsm/kg. In one embodiment, the base medium exhibits about 5.1 mg/mL NaCl, 1.5 mg/mL sodium bicarbonate, and 261 mOsm/kg. In one embodiment, the base medium exhibits 110±5 mM NaCl, 18±5 mM carbonate, and 294±29 mOsm/kg. In one embodiment, the base medium exhibits about 6.4 mg/mL NaCl, 1.5 mg/mL sodium bicarbonate, and 294 mOsm/kg. In one embodiment, the base medium exhibits 87±5 mM NaCl, 26±5 mM carbonate, and 270±27 mOsm/kg. In one embodiment, the base medium exhibits about 5.1 mg/mL NaCl, 2.2 mg/mL sodium bicarbonate, and 270 mOsm/kg. In one embodiment, wherein the base medium exhibits 87±5 mM NaCl, 26±5 mM carbonate, 86±5 mM glucose, and 322±32 mOsm/kg. In one embodiment, wherein the base medium exhibits about 5.1 mg/mL NaCl, 2.2 mg/mL sodium bicarbonate, 15.5 mg/mL glucose, and 322 mOsm/kg.

Further provided are methods of producing a transgenic non-human mammal homozygous for a targeted genetic mutation in the F1 generation comprising: (a) crossing an F0 XY fertile female having a decreased level and/or activity of the Sry protein with a cohort clonal sibling, derived from the same ES cell clone, F0 XY male non-human mammal, wherein the F0 XY fertile female non-human mammal and the F0 XY male non-human mammal each is heterozygous for the genetic mutation; and, (b) obtaining an F1 progeny mouse that is homozygous for the genetic modification.

A method for modifying a target genomic locus on the Y chromosome in a cell is also provided and comprises (a) providing a cell comprising a target genomic locus on the Y chromosome comprising a recognition site for a nuclease agent, (b) introducing into the cell (i) the nuclease agent, wherein the nuclease agent induces a nick or double-strand break at the first recognition site; and, (ii) a first targeting vector comprising a first insert polynucleotide flanked by a first and a second homology arm corresponding to a first and a second target site located in sufficient proximity to the first recognition site; and, (c) identifying at least one cell comprising in its genome the first insert polynucleotide integrated at the target genomic locus. In one embodiment, a sum total of the first homology arm and the second homology arm is at least 4 kb but less than 150 kb. In one embodiment, the length of the first homology arm and/or the second homology arm is at least 400 bp but less than 1000 bp. In another embodiment, the length of the first homology arm and/or the second homology arm is from about 700 bp to about 800 bp.

Further provided is a method for modifying a target genomic locus on the Y chromosome in a cell is provided and comprises: (a) providing a cell comprising a target genomic locus on the Y chromosome comprising a recognition site for a nuclease agent, (b) introducing into the cell a first targeting vector comprising a first insert polynucleotide flanked by a first and a second homology arm corresponding to a first and a second target site; and, (c) identifying at least one cell comprising in its genome the first insert polynucleotide integrated at the target genomic locus. In one embodiment, the length of the first homology arm and/or the second homology arm is at least 400 bp but less than 1000 bp. In another embodiment, the length of the first homology arm and/or the second homology arm is from about 700 bp to about 800 bp. In one embodiment, the cell is a mammalian cell. In one embodiment, the mammalian cell is a non-human cell. In one embodiment, the mammalian cell is from a rodent. In one embodiment, the rodent is a rat, a mouse or a hamster. In one embodiment, the cell is a pluripotent cell. In one embodiment, the mammalian cell is an induced pluripotent stem (iPS) cell. In one embodiment, the pluripotent cell is a non-human embryonic stem (ES) cell. In one embodiment, the pluripotent cell is a rodent embryonic stem (ES) cell, a mouse embryonic stem (ES) cell or a rat embryonic stem (ES) cell. In one embodiment, the nuclease agent is an mRNA encoding a nuclease. In one embodiment, the nuclease agent is a zinc finger nuclease (ZFN). In one embodiment, the nuclease agent is a Transcription Activator-Like Effector Nuclease (TALEN). In one embodiment, the nuclease agent is a meganuclease. In some embodiments, the nuclease agent comprises a Clustered Regularly Interspaced Short Palindromic Repeats (CRISPR)-associated (Cas) protein and a guide RNA (gRNA). In such a method the guide RNA (gRNA) can comprise (a) a Clustered Regularly Interspaced Short Palindromic Repeats (CRISPR) RNA (crRNA) that targets the first recognition site; and (b) a trans-activating CRISPR RNA (tracrRNA). In one embodiment, the first or the second recognition sites are immediately flanked by a Protospacer Adjacent Motif (PAM) sequence. In some embodiments, the Cas protein is Cas9.

In some embodiments, the modification comprises a deletion of an endogenous nucleic acid sequence. In some embodiments, the deletion ranges from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb. In a specific embodiment, the deletion is at least 500 kb. In one embodiment, the cell is a mammalian cell. In one embodiment, the mammalian cell is a non-human cell. In one embodiment, the mammalian cell is from a rodent. In one embodiment, the rodent is a rat, a mouse or a hamster. In one embodiment, the cell is a pluripotent cell. In one embodiment, the mammalian cell is an induced pluripotent stem (iPS) cell. In one embodiment, the pluripotent cell is a non-human embryonic stem (ES) cell. In one embodiment, the pluripotent cell is a rodent embryonic stem (ES) cell, a mouse embryonic stem (ES) cell or a rat embryonic stem (ES) cell. In some embodiments, the nuclease agent comprises a Clustered Regularly Interspaced Short Palindromic Repeats (CRISPR)-associated (Cas) protein and a guide RNA (gRNA). In such a method the guide RNA (gRNA) can comprise (a) a Clustered Regularly Interspaced Short Palindromic Repeats (CRISPR) RNA (crRNA) that targets the first recognition site; and (b) a trans-activating CRISPR RNA (tracrRNA). In one embodiment, the first or the second recognition sites are immediately flanked by a Protospacer Adjacent Motif (PAM) sequence. In some embodiments, the Cas protein is Cas9. In one embodiment, the nuclease agent is a zinc finger nuclease (ZFN). In one embodiment, the nuclease agent is a Transcription Activator-Like Effector Nuclease (TALEN). In one embodiment, the nuclease agent is a meganuclease.

Methods for modifying the Y chromosome comprising exposing the Y chromosome to a Cas protein and a CRISPR RNA in the presence of a large targeting vector (LTVEC) comprising a nucleic acid sequence of at least 10 kb and comprises following exposure to the Cas protein, the CRISPR RNA, and the LTVEC, the Y chromosome is modified to contain at least 10 kb nucleic acid sequence. The LTVEC can comprise a nucleic acid sequence of at least 20 kb, at least 30 kb, at least 40 kb, at least 50 kb, at least 60 kb, at least 70 kb, at least 80 kb, or at least 90 kb. In other embodiments, the LTVEC comprises a nucleic acid sequence of at least 100 kb, at least 150 kb, or at least 200 kb.

Further provided is a method for modifying a target genomic locus on the Y chromosome, comprising: (a) providing a mammalian cell comprising the target genomic locus on the Y chromosome, wherein the target genomic locus comprises a guide RNA (gRNA) target sequence; (b) introducing into the mammalian cell: (i) a large targeting vector (LTVEC) comprising a first nucleic acid flanked with targeting arms homologous to the target genomic locus, wherein the LTVEC is at least 10 kb; (ii) a first expression construct comprising a first promoter operably linked to a second nucleic acid encoding a Cas protein, and (iii) a second expression construct comprising a second promoter operably linked to a third nucleic acid encoding a guide RNA (gRNA) comprising a nucleotide sequence that hybridizes to the gRNA target sequence and a trans-activating CRISPR RNA (tracrRNA), wherein the first and the second promoters are active in the mammalian cell; and (c) identifying a modified mammalian cell comprising a targeted genetic modification at the target genomic locus on the Y chromosome. In other embodiments, the LTVEC is at least 15 kb, at least 20 kb, at least 30 kb, at least 40 kb, at least 50 kb, at least 60 kb, at least 70 kb, at least 80 kb, or at least 90 kb. In other embodiments, the LTVEC is at least 100 kb, at least 150 kb, or at least 200 kb. In one embodiment, the mammalian cell is a non-human mammalian cell. In one embodiment, the mammalian cell is a fibroblast cell. In one embodiment, the mammalian cell is from a rodent. In one embodiment, the rodent is a rat, a mouse, or a hamster. In one embodiment, the mammalian cell is a pluripotent cell. In one embodiment, the pluripotent cell is an induced pluripotent stem (iPS) cell. In one embodiment, the pluripotent cell is a mouse embryonic stem (ES) cell or a rat embryonic stem (ES) cell. In one embodiment, the pluripotent cell is a developmentally restricted human progenitor cell. In one embodiment, the Cas protein is a Cas9 protein. In one embodiment, the gRNA target sequence is immediately flanked by a Protospacer Adjacent Motif (PAM) sequence. In one embodiment, the sum total of 5' and 3' homology arms of the LTVEC is from about 10 kb to about 150 kb. In one embodiment, the sum total of the 5' and the 3' homology arms of the LTVEC is from about 10 kb to about 20 kb, from about 20 kb to about 40 kb, from about 40 kb to about 60 kb, from about 60 kb to about 80 kb, from about 80 kb to about 100 kb, from about 100 kb to about 120 kb, or from about 120 kb to 150 kb. In one embodiment, the targeted genetic modification comprises: (a) a replacement of an endogenous nucleic acid sequence with a homologous or an orthologous nucleic acid sequence; (b) a deletion of an endogenous nucleic acid sequence; (c) a deletion of an endogenous nucleic acid sequence, wherein the deletion ranges from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb; (d) insertion of an exogenous nucleic acid sequence; (e) insertion of an exogenous nucleic acid sequence ranging from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb; (f) insertion of an exogenous nucleic acid sequence comprising a homologous or an orthologous nucleic acid sequence; (g) insertion of a chimeric nucleic acid sequence comprising a human and a non-human nucleic acid sequence; (h) insertion of a conditional allele flanked with site-specific recombinase target sequences; (i) insertion of a selectable marker or a reporter gene operably linked to a third promoter active in the mammalian cell; or (j) a combination thereof. In one embodiment, the target genomic locus comprises (i) a 5' target sequence that is homologous to a 5' homology arm; and (ii) a 3' target sequence that is homologous to a 3' homology arm. In one embodiment, the 5' target sequence and the 3' target sequence is separated by at least 5 kb but less than 3 Mb. In one embodiment, the 5' target sequence and the 3' target sequence is separated by at least 5 kb but less than 10 kb, at least 10 kb but less than 20 kb, at least 20 kb but less than 40 kb, at least 40 kb but less than 60 kb, at least 60 kb but less than 80 kb, at least about 80 kb but less than 100 kb, at least 100 kb but less than 150 kb, or at least 150 kb but less than 200 kb, at least about 200 kb but less than about 300 kb, at least about 300 kb but less than about 400 kb, at least about 400 kb but less than about 500 kb, at least about 500 kb but less than about 1 Mb, at least about 1 Mb but less than about 1.5 Mb, at least about 1.5 Mb but less than about 2 Mb, at least about 2 Mb but less than about 2.5 Mb, or at least about 2.5 Mb but less than about 3 Mb. In one embodiment, the first and the second expression constructs are on a single nucleic acid molecule. In one embodiment, the target genomic locus comprises the Sry locus.

Further provided is a method for targeted genetic modification on the Y chromosome of a non-human animal, comprising: (a) modifying a genomic locus of interest on the Y chromosome of a non-human pluripotent cell according to the methods described herein, thereby producing a genetically modified non-human pluripotent cell comprising a targeted genetic modification on the Y chromosome; (b) introducing the modified non-human pluripotent cell of (a) into a non-human host embryo; and gestating the non-human host embryo comprising the modified pluripotent cell in a surrogate mother, wherein the surrogate mother produces F0 progeny comprising the targeted genetic modification, wherein the targeted genetic modification is capable of being transmitted through the germline. In one embodiment, the genomic locus of interest comprises the Sry locus.

Methods and compositions are provided for generating targeted genetic modifications on the Y chromosome. Compositions include an in vitro culture comprising an XY pluripotent and/or totipotent animal cell (i.e., XY ES cells or XY iPS cells) having a modification that decreases the level and/or activity of an Sry protein; and, culturing these cells in a medium that promotes development of XY F0 fertile females. Such compositions find use in various methods for making a fertile female XY non-human mammals in an F0 generation.

BRIEF DESCRIPTION OF THE FIGURES

FIGS. 5 A, B, and C provides the sequencing confirmation of the large Y chromosome deletion in various clones. FIG. 5A is the sequencing result for clone 1-D5. The Kdm5 Up and Uspy9 down sequence is provided in SEQ ID NO:30; 1-D5 1500F (SEQ ID NO:31); 1-D5 1000R (SEQ ID NO:32); FIG. 5B is the sequencing result for clone 5-C4. The Kdm5 Up and Uspy9 down sequence is provided in SEQ ID NO:33; 1500F (SEQ ID NO:34); 1000R (SEQ ID NO:35); 1000F (SEQ ID NO:36); and FIG. 5C is the sequencing result for clone 6-A12. The Kdm5 Up and Uspy9 down sequence is provided in SEQ ID NO:37; 1500F (SEQ ID NO:38); 1000R (SEQ ID NO:39); 1000F (SEQ ID NO:40); 1500R (SEQ ID NO:41). The boxed regions in FIG. 5B and FIG. 5C represent micro-homology regions.

DETAILED DESCRIPTION

Definitions

Figure 1:
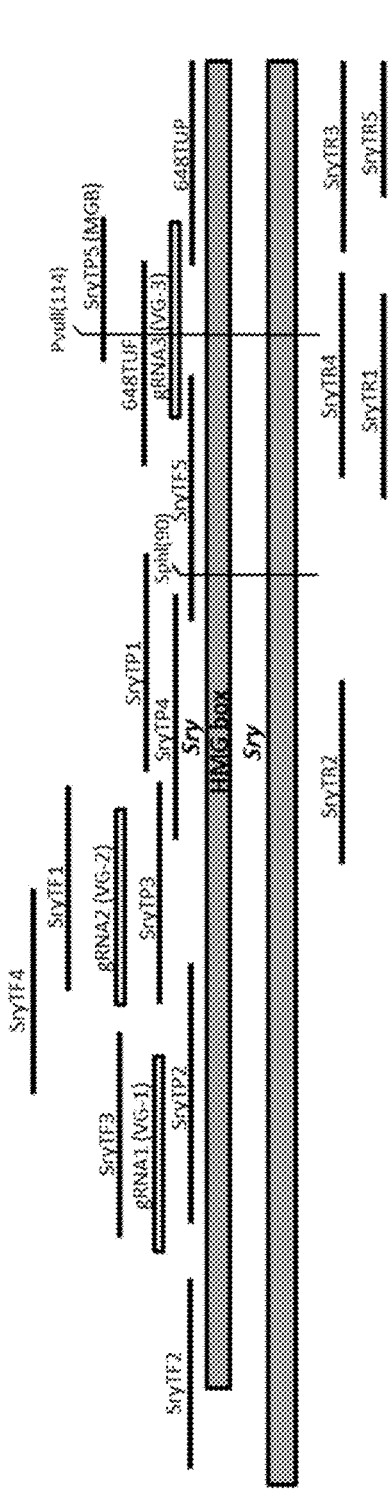
FIG. 1 provides a schematic of the CRISPR Cas9/gRNA targeting the mouse Sry gene. VG-1 (SEQ ID NO:10); VG-2 (SEQ ID NO:11); VG-3 (SEQ ID NO:12). The primers and probes indicated in FIG. 1 are provided in SEQ ID NOS: 13-29.

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones.

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases. For simplicity, nucleic acid size may be referred to in by whether the nucleic acid is in double- or single-stranded form, in the latter case, the by being those formed if and when the single-stranded nucleic acid is duplexed with its exactly complementary strand.

"Codon optimization" generally includes a process of modifying a nucleic acid sequence for enhanced expression in particular host cells by replacing at least one codon of the native sequence with a codon that is more frequently or most frequently used in the genes of the host cell while maintaining the native amino acid sequence. For example, a nucleic acid encoding a Cas protein can be modified to substitute codons having a higher frequency of usage in a given prokaryotic or eukaryotic cell, including a bacterial cell, a yeast cell, a human cell, a non-human cell, a mammalian cell, a rodent cell, a mouse cell, a rat cell, a hamster cell, or any other host cell, as compared to the naturally occurring nucleic acid sequence. Codon usage tables are readily available, for example, at the "Codon Usage Database." These tables can be adapted in a number of ways. See Nakamura et al. (2000) *Nucleic Acids Research* 28:292. Computer algorithms for codon optimization of a particular sequence for expression in a particular host are also available (see, e.g., Gene Forge).

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors.

"Complementarity" of nucleic acids means that a nucleotide sequence in one strand of nucleic acid, due to orientation of its nucleobase groups, forms hydrogen bonds with another sequence on an opposing nucleic acid strand. The complementary bases in DNA are typically A with T and C with G. In RNA, they are typically C with G and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm of hybridized strands, or by empirical determination of Tm by using routine methods. Tm includes the temperature at which a population of hybridization complexes formed between two nucleic acid strands are 50% denatured. At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+0.41(% G+C), although other known Tm computations take into account nucleic acid structural characteristics.

"Hybridization condition" includes the cumulative environment in which one nucleic acid strand bonds to a second nucleic acid strand by complementary strand interactions and hydrogen bonding to produce a hybridization complex. Such conditions include the chemical components and their concentrations (e.g., salts, chelating agents, formamide) of an aqueous or organic solution containing the nucleic acids, and the temperature of the mixture. Other factors, such as the length of incubation time or reaction chamber dimensions may contribute to the environment. See, e.g., Sambrook et al., Molecular Cloning, A Laboratory Manual, 2.sup.nd ed., pp. 1.90-1.91, 9.47-9.51, 1 1.47-11.57 (Cold Spring Harbor Laboratory Press, Cold Spring Harbor, N. Y., 1989).

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or fewer, 30 or fewer, 25 or fewer, 22 or fewer, 20 or fewer, or 18 or fewer nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid include at least about 15 nucleotides, at least about 20 nucleotides, at least about 22 nucleotides, at least about 25 nucleotides, and at least about 30 nucleotides. Furthermore, the temperature and wash solution salt concentration may be adjusted as necessary according to factors such as length of the region of complementation and the degree of complementation.

The sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure). A polynucleotide (e.g., gRNA) can comprise at least 70%, at least 80%, at least 90%, at least 95%, at least 99%, or 100% sequence complementarity to a target region within the target nucleic acid sequence to which they are targeted. For example, a gRNA in which 18 of 20 nucleotides are complementary to a target region, and would therefore specifically hybridize, would represent 90% complementarity. In this example, the remaining noncomplementary nucleotides may be clustered or interspersed with complementary nucleotides and need not be contiguous to each other or to complementary nucleotides.

Percent complementarity between particular stretches of nucleic acid sequences within nucleic acids can be determined routinely using BLAST programs (basic local alignment search tools) and PowerBLAST programs known in the art (Altschul et al. (1990) *J. Mol. Biol.* 215:403-410; Zhang and Madden (1997) *Genome Res.* 7:649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

The methods and compositions provided herein employ a variety of different components. It is recognized throughout the description that some components can have active variants and fragments. Such components include, for example, Cas proteins, CRISPR RNAs, tracrRNAs, and guide RNAs. Biological activity for each of these components is described elsewhere herein.

"Sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

"Percentage of sequence identity" includes the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" includes any sequence comparison program that, for any two sequences in question, generates an alignment having identical nucleotide or amino acid residue matches and an identical percent sequence identity when compared to the corresponding alignment generated by GAP Version 10.

Compositions or methods "comprising" or "including" one or more recited elements may include other elements not specifically recited. For example, a composition that "comprises" or "includes" a protein may contain the protein alone or in combination with other ingredients.

Designation of a range of values includes all integers within or defining the range, and all subranges defined by integers within the range.

Unless otherwise apparent from the context, the term "about" encompasses values within a standard margin of error of measurement (e.g., SEM) of a stated value.

The singular forms of the articles "a," "an," and "the" include plural references unless the context clearly dictates otherwise. For example, the term "a Cas protein" or "at least one Cas protein" can include a plurality of Cas proteins, including mixtures thereof.

I. Methods and Compositions to Make a Fertile Female XY Animal in an F0 Generation Methods for making non-human animals from donor ES cells and host embryos are known. Donor ES cells are selected for certain characteristics that enhance the ability of the cells to populate a host embryo and thus contribute in part or in substantial part to an animal formed by the donor ES cells and the host embryo. The animal formed may be male or female, based in large part on the genotype of the ES cell (e.g., XY or XX).

The majority of ES cell lines for making transgenic animals have a male XY genotype. Because of the dominance of the Y chromosome in mammalian sex determination, when XY ES cells are introduced into a blastocyst host embryo and gestated, they nearly always produce in the first generation (F0) phenotypically male animals that are chimeras, i.e., that contain cells derived from the male donor ES cell (XY) and cells derived from the host embryo, which can be either male (XY) or female (XX). XY ES cells, when introduced into an 8-cell host embryo by the VelociMouse method and gestated, can produce in the first generation (F0) phenotypically male animals that are fully derived from the XY ES cells.

WO2011/156723 provides methods and compositions which employ a culture media for maintaining XY donor cells in culture such that after introduction of the XY donor cells into a host embryo and gestation in a suitable host, fertile XY female animals are produced in the F0 population. Such compositions find use in making F1 progeny that are homozygous for the given targeted genetic modification.

The instant application provides methods and compositions that employ a combination of XY donor cells having a modification that decreases the level and/or activity of the Sry protein in combination with a culture media that promotes the production of anatomically normal, fertile and fecund, XY F0 females. Such methods and compositions allow for making a fertile female XY non-human animal in an F0 generation. The combination of XY ES cells having a modification that decreases the level and/or activity of the Sry protein in combination with the culture media described herein significantly increases the percentage of fertile female XY progeny in the F0 generation. Methods for the efficient male to female sex conversion are valuable to the domestic animal industry. For example, female calves are much more valuable to the dairy cattle industry than males. The same is true for poultry. For breeding purposes, whether it be cattle or hogs or sheep, it is preferred to breed many females to only a few bulls, boars, or rams. Thus, the various methods provided herein find use in various commercially important breeding industries.

Methods and compositions are also provided for making a XY embryonic stem (ES) cell line capable of producing a fertile XY female non-human mammal in an F0 generation without culturing in a feminizing media. In such methods, the XY ES cell line having a modification that decreases the level and/or activity of an Sry protein can produce an ES cell line capable of producing a fertile XY female non-human mammal in an F0 generation in the absence of a feminizing media provided elsewhere herein (e.g., by culturing in a base medium, such as DMEM, described elsewhere herein).

A. Animal XY Cells Having a Modification that Decreases the Level and/or Activity of an Sry Protein Various compositions and methods are provided herein which comprise various XY pluripotent and/or totipotent cells from an animal. The term "pluripotent cell" as used herein includes an undifferentiated cell that possesses the ability to develop into more than one differentiated cell types. Such pluripotent and/or totipotent XY cells can be, for example, an embryonic stem (ES) cell or an induced pluripotent stem (iPS) cell. The term "embryonic stem cell" or "ES cell" as used herein includes an embryo-derived totipotent or pluripotent cell that is capable of contributing to any tissue of the developing embryo upon introduction into an embryo.

The term "animal," in reference to cells, pluripotent and/or totipotent cells, XY cells, ES cells, iPS cells, donor cells and/or host embryos, includes mammals, fishes, and birds. Mammals include, e.g., humans, non-human primates, monkey, ape, cat dog, horse, bull, deer, bison, sheep, rodents (e.g., mice, rats, hamsters, guinea pigs), livestock (e.g., bovine species, e.g., cows, steer, etc.; ovine species, e.g., sheep, goats, etc.; and porcine species, e.g., pigs and boars). Birds include, e.g., chickens, turkeys, ostrich, geese, ducks, etc. Domesticated animals and agricultural animals are also included. The phrase "non-human animal," in reference to cells, XY cells, ES cells, donor cells and/or host embryos, excludes humans.

In specific embodiments, the pluripotent cell is a human XY ES cell, a human XY iPS cell, a human adult XY ES cell, a developmentally restricted human progenitor ES cell, a non-human XY ES cell, a non-human XY iPS cell, a rodent XY ES cell, a rodent XY iPS cell, a mouse XY ES cell, a mouse XY iPS cell, a rat XY ES cell, a rat XY iPS cell, a hamster XY ES cell, a hamster XY iPS cell, a monkey XY ES cell, a monkey XY iPS cell, an agricultural mammal XY ES cell, an agricultural XY iPS cell, a domesticated mammal XY ES cell, or a domesticated XY iPS cell. Moreover, the XY ES cell or the XY iPS cell can be from an inbred strain, a hybrid strain or an outbred strain. It is further recognized that the pluripotent and/or totipotent XY cells can comprise an XYY karyotype or an XXY karyotype.

Mouse pluripotent and/or totipotent cells (i.e., XY ES cells or XY iPS cells) can be from a 129 strain, a C57BL/6 strain, a mix of 129 and C57BL/6, a BALB/c strain, or a Swiss Webster strain. In a specific embodiment, the mouse is 50% 129 and 50% C57BL/6. In one embodiment, the mouse is a 129 strain selected from the group consisting of a strain that is 129P1, 129P2, 129P3, 129X1, 129S1 (e.g., 129S1/SV, 129S1/Svlm), 129S2, 129S4, 129S5, 129S9/SvEvH, 129S6 (129/SvEvTac), 129S7, 129S8, 129T1, 129T2. See, for example, Festing et al. (1999) *Mammalian Genome* 10:836). In one embodiment, the mouse is a C57BL strain, and in a specific embodiment is from C57BL/A, C57BL/An, C57BL/GrFa, C57BL/Kal_wN, C57BL/6, C57BL/6J, C57BL/6ByJ, C57BL/6NJ, C57BL/6NTac, C57BL/10, C57BL/10ScSn, C57BL/10Cr, or C57BL/O1a. In a specific embodiment, the mouse is a mix of an aforementioned 129 strain and an aforementioned C57BL/6 strain. In another specific embodiment, the mouse is a mix of aforementioned 129 strains, or a mix of aforementioned BL/6 strains. In a specific embodiment, the 129 strain of the mix is a 129S6 (129/SvEvTac) strain. In some embodiments, the mouse XY ES cell comprises a Y chromosome derived from the 129 strain.

In yet another embodiment, the XY mouse ES cell is a VGF1 mouse ES cell. VGF1 (also known as F1H4) mouse ES cells were derived from hybrid embryos produced by crossing a female C57BL/6NTac mouse to a male 129S6/SvEvTac mouse. Therefore, VGF1 ES cells contain a Y chromosome from 129S6/SvEvTac mouse. See, for example, Auerbach, W. et al. (2000) Establishment and chimera analysis of 129/SvEv- and C57BL/6-derived mouse embryonic stem cell lines. *Biotechniques* 29, 1024-1028, 1030, 1032, herein incorporated by reference in its entirety.

A rat pluripotent and/or totipotent cell (i.e., XY ES cell or XY iPS cell) can be from any rat strain, including but not limited to, an ACI rat strain, a Dark Agouti (DA) rat strain, a Wistar rat strain, a LEA rat strain, a Sprague Dawley (SD)

rat strain, or a Fischer rat strain such as Fisher F344 or Fisher F6. Rat pluripotent and/or totipotent cells (i.e., XY ES cells or XY iPS cells) can also be obtained from a strain derived from a mix of two or more strains recited above. In one embodiment, the rat pluripotent and/or totipotent cell (i.e., XY ES cell or XY iPS cell) is derived from a strain selected from a DA strain and an ACI strain. In a specific embodiment, the rat pluripotent and/or totipotent cell (i.e., XY ES cell or XY iPS cell) is derived from an ACI strain. The ACI rat strain is characterized as having black agouti, with white belly and feet and an RT1$^{av1}$ haplotype. Such strains are available from a variety of sources including Harlan Laboratories. In other embodiments, the various rat pluripotent and/or totipotent cell (i.e., XY ES cell or XY iPS cell) are from a Dark Agouti (DA) rat strain, which is characterized as having an agouti coat and an RT1$^{av1}$ haplotype. Such rats are available from a variety of sources including Charles River and Harlan Laboratories. In a further embodiment, the rat pluripotent and/or totipotent cells (i.e., XY ES cells or XY iPS cells) are from an inbred rat strain. In specific embodiments the rat ES cell line is from an ACI rat and comprises the ACI.G1 rat ES cell. In another embodiment, the rat ES cell line is from a DA rat and comprises the DA.2B rat ES cell line or the DA.2C rat ES cell line. See, for example, U.S. Utility application Ser. No. 14/185,703, filed on Feb. 20, 2014 and herein incorporated by reference in its entirety.

In various embodiments, the pluripotent and/or totipotent cell (i.e., XY ES cell or XY iPS cell), the donor cell and/or the host embryo are not from one or more of the following: *Akodon* spp., *Myopus* spp., *Microtus* spp., *Talpa* spp. In various embodiments, the donor cell and/or the host embryo are not from any species of which a normal wild-type characteristic is XY female fertility. In various embodiments, where a genetic modification is present in the pluripotent and/or totipotent cell (i.e., XY ES cell or XY iPS cell), the donor cell or the host embryo, the genetic modification is not an XYY or XXY, a Tdy-negative sex reversal, Tdy-positive sex reversal, an X0 modification, an aneuploidy, an fgf9$^{-/-}$ genotype, or a SOX9 modification.

The pluripotent and/or totipotent XY cells (i.e., an XY ES cell or an XY iPS cell) employed in the methods and compositions have a genetic modification that results in a decreased level and/or activity of the Sry protein. The "Sex Determining Region Y" protein or the "Sry" protein is a transcription factor that is a member of the high mobility group (HMG)-box family of DNA-binding proteins. Sry is the testis-determining factor that initiates male sex determination. The sequence of the Sry protein from a variety of organisms is known, including from mouse (Accession No. Q05738); rat (GenBank: CAA61882.1) human (Accession No. Q05066); cat (Accession No. Q67C50), and horse (Accession No. P36389), each of which is herein incorporated by reference.

In general, the level and/or activity of the Sry protein is decreased if the protein level and/or the activity level of the Sry protein is statistically lower than the protein level of Sry in an appropriate control cell that has not been genetically modified or mutagenized to inhibit the expression and/or activity of the Sry protein. In specific embodiments, the concentration and/or activity of the Sry protein is decreased by at least 1%, 5%, 10%, 20%, 30%, 40%, 50%, 60%, 70%, 80%, or 90% relative to a control cell which has not been modified to have the decreased level and/or activity of the Sry protein.

A "subject cell" is one in which a genetic alteration, such as a genetic modification disclosed herein has been effected, or is a cell which is descended from a cell so altered and which comprises the alteration. A "control" or "control cell" provides a reference point for measuring changes in phenotype of the subject cell. In one embodiment, a control cell is as closely matched as possible with the cell with reduced Sry activity except it lacks the genetic modification or mutation resulting in the reduced activity (for example, the respective cells can originate from the same cell line). In other instances, the control cell may comprise, for example: (a) a wild-type cell, i.e., of the same genotype as the starting material for the genetic alteration which resulted in the subject cell; (b) a cell of the same genotype as the starting material but which has been genetically modified with a null construct (i.e. with a construct which has no known effect on the trait of interest, such as a construct comprising a marker gene); (c) a cell which is a non-genetically modified progeny of a subject cell (i.e., the control cell and the subject cell originate from the same cell line); (d) a cell genetically identical to the subject cell but which is not exposed to conditions or stimuli that would induce expression of the gene of interest; or (e) the subject cell itself, under conditions in which the genetic modification does not result in an alteration in expression of the polynucleotide of interest.

The expression level of the Sry polypeptide may be measured directly, for example, by assaying for the level of the Sry polypeptide in the cell or organism, or indirectly, for example, by measuring the activity of the Sry polypeptide. Various methods for determining the activity of the Sry protein are known. See, Wang et al. (2013) *Cell* 153:910-918, Mandalos et al. (2012) *PLOS ONE* 7:e45768:1-9, and Wang et al. (2013) *Nat Biotechnol.* 31:530-532, each of which is herein incorporated by reference.

In other instances, cells having the targeted genetic modification that reduces the activity and/or level of the Sry polypeptide are selected using methods that include, but are not limited to, Southern blot analysis, DNA sequencing, PCR analysis, or phenotypic analysis. Such cells are then employed in the various methods, compositions and kits described herein.

A targeted genetic modification can comprise a targeted alteration to a polynucleotide of interest including, for example, a targeted alteration to a target genomic locus on the Y chromosome, a targeted alteration to the Sry gene, or a targeted alteration to other desired polynucleotides. Such targeted modifications include, but are not limited to, additions of one or more nucleotides, deletions of one or more nucleotides, substitutions of one or more nucleotides, a knockout of the polynucleotide of interest or a portion thereof, a knock-in of the polynucleotide of interest or a portion thereof, a replacement of an endogenous nucleic acid sequence with a heterologous nucleic acid sequence, or a combination thereof. In specific embodiments, at least 1, 2, 3, 4, 5, 7, 8, 9, 10 or more nucleotides are changed to form the targeted genomic modification.

A decrease in the level and/or activity of the Sry protein can result from a genetic modification in the Sry gene (i.e., a genetic modification in a regulatory region, the coding region, and/or introns etc). Such genetic modifications include, but are not limited to, additions, deletions, and substitutions of nucleotides into the genome. Such genetic modifications can include an alteration of the Sry gene, including, for example, an insertion of one or more nucleotides into the Sry gene, a deletion of one or more nucleotides from the Sry gene, a substitution of one or more nucleotides in the Sry gene, a knockout of the Sry gene or a portion thereof, a knockin of the Sry gene or a portion thereof, a replacement of an endogenous nucleic acid sequence with a heterologous nucleic acid sequence, or a combination thereof. Thus, in specific embodiments, the activity of an Sry polypeptide may be reduced or eliminated by disrupting the gene encoding the Sry polypeptide. In specific embodiments, at least 1, 2, 3, 4, 5, 7, 8, 9, 10 or more nucleotides are changed in the Sry gene. Various methods can be used to generate the additional targeted genetic modification. See, for example, Wang et al. (2013) Cell 153:910-918, Mandalos et al. (2012) PLOS ONE 7:e45768:1-9, and Wang et al. (2013) Nat Biotechnol. 31:530-532, each of which is herein incorporated by reference. In addition, the various methods described herein to modify genomic locus on the Y chromosome can be used to introduce targeted genetic modification to the Sry gene.

In other embodiments, the activity and/or level of the Sry polypeptide is reduced or eliminated by introducing into the cell a polynucleotide that inhibits the level or activity of the Sry polypeptide. The polynucleotide may inhibit the expression of the Sry polypeptide directly, by preventing translation of the Sry messenger RNA, or indirectly, by encoding a polypeptide that inhibits the transcription or translation of the gene encoding an Sry protein. In other embodiments, the activity of Sry polypeptide is reduced or eliminated by introducing into the cell a sequence encoding a polypeptide that inhibits the activity of the Sry polypeptide.

In one embodiment, the XY pluripotent and/or totipotent cells (i.e., XY ES cell or XY iPS cell) comprise a conditional Sry allele that reduces the activity and/or level of the Sry protein. A "conditional Sry allele" includes a modified Sry gene designed to have the decreased level and/or activity of the Sry protein at a desired developmental time and/or within a desired tissue of interest. Reduced level and/or activity can be compared with a control cell lacking the modification giving rise to the conditional allele, or in the case of reduced activity at a desired developmental time with preceding and/or following times, or in the case of a desired tissue, with a mean activity of all tissues. In one embodiment, the conditional Sry allele comprises a conditional null allele of Sry that can be switch off at a desired developmental time point and/or in specific tissues. Such a conditional allele can be used to create fertile XY females derived from any gene-targeted clone. As described elsewhere herein, such a method enables the creation of a desired homozygous genetic modification in the F1 generation. Such methods provide a quick look at the phenotype without having to breed to the F2 generation.

In a non-limiting embodiment, the conditional Sry allele is a multifunctional allele, as described in US 2011/0104799, which is incorporated by reference in its entirety. In specific embodiments, the conditional allele comprises: (a) an actuating sequence in sense orientation with respect to transcription of a target gene, and a drug selection cassette (DSC) in sense or antisense orientation; (b) in antisense orientation a nucleotide sequence of interest (NSI) and a conditional by inversion module (COIN, which utilizes an exon-splitting intron and an invertible genetrap-like module; see, for example, US 2011/0104799, which is incorporated by reference in its entirety); and (c) recombinable units that recombine upon exposure to a first recombinase to form a conditional allele that (i) lacks the actuating sequence and the DSC, and (ii) contains the NSI in sense orientation and the COIN in antisense orientation.

The conditional allele of the Sry gene can be generated in any cell type, and is not limited to an XY pluripotent and/or totipotent cell. Such cells types along with non-limiting methods to target a genomic locus on the Y chromosome are discussed in further detail elsewhere herein.

As discussed elsewhere herein, the pluripotent and/or totipotent XY cell (i.e., an XY ES cell or an XY iPS cell) having genetic modification that decreases the level and/or activity of the Sry protein can further comprise at least one additional targeted genetic modification to a polynucleotide of interest. The at least one additional targeted genetic modification can comprise a substitution of one or more nucleic acids, a replacement of an endogenous nucleic acid sequence with a heterologous nucleic acid sequence, a knockout, and a knock-in. The additional targeted genetic modification can be on the Y chromosome, the X chromosome or on an autosome. Various methods can be used to generate the additional targeted genetic modification, including employing targeting plasmids and large targeting vectors as discussed elsewhere herein. See, also, US20080092249, WO/1999/005266A2, US200401077390, WO/2008/017234A1, and U.S. Pat. No. 7,612,250, each of which is herein incorporated by reference, for methods related to nuclear transfer. In addition, the various methods described herein to modify genomic locus on the Y chromosome (i.e., the Sry gene) can also be used to introduce targeted genetic modifications to polynucleotides of interest that are not located on the Y chromosome.

B. Media for Culturing the Pluripotent and/or Totipotent XY Cells Having a Modification that Decreases the Level and/or Activity of an Sry Protein The culture media employed in the various methods and compositions that promote XY fertile female in the F0 generation is such that it maintains the pluripotent and/or totipotent cells (i.e., ES cell, iPS cells, XY ES cells, XY iPS cells, etc.). The terms "maintain", "maintaining" and "maintenance" refer to the stable preservation of at least one or more of the characteristics or phenotypes of pluripotent and/or totipotent cells described herein (including ES cells or iPS cells). Such phenotypes can include maintaining pluripotency and/or totipotency, cell morphology, gene expression profiles and the other functional characteristics of the cells. The terms "maintain", "maintaining" and "maintenance" can also encompass the propagation of cells, or an increase in the number of cells being cultured. The terms further contemplate culture conditions that permit the cells to remain pluripotent, while the cells may or may not continue to divide and increase in number.

In some embodiments, the XY cells having the genetic modification that reduces the level and/or activity of the Sry protein are maintained by culturing in any base medium known in the art (e.g., DMEM) that is suitable for use (with added supplements) in growing or maintaining the pluripotent and/or totipotent cells (i.e., ES cell, iPS cells, XY ES cells, XY iPS cells, etc.) in culture. In such cases, the cultured XY ES cells have the potential to develop into fertile female animals but still retain pluripotency and/or totipotency, such that the cells can be implemented into a recipient embryo and give rise to a fertile female progeny.

In other embodiments, XY cells having the genetic modification that reduces the level and/or activity of the Sry protein are maintained by culturing in a medium as further defined below for sufficient time that some of the cells convert to XY cells with the potential to develop into fertile female animals but still retain pluripotency and/or totipotency, such that the cells can be implemented into a recipient embryo and give rise to a fertile female progeny.

The medium employed to maintain the XY pluripotent and/or totipotent cells (i.e., XY ES cells, XY iPS cells, etc.) having the genetic modification that reduces the level and/or activity of the Sry protein promotes the development of XY F0 fertile females. Thus, culturing in such a medium increases the number of XY F0 fertile females that are obtained when compared to culturing in an appropriate control medium (such as, for example, one based on DMEM). Thus, an increased number of XY F0 fertile females can comprise at least 10%, 15%, 20%, 25%, 30%, 40%, 50%, 60%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% of the F0 non-human animals (following introduction of the non-human animal XY ES cells into a host embryo and gestation of the host embryo) are XY females and which upon attaining sexual maturity the F0 XY female non-human animal is fertile.

The phrase "base medium" or "base media" includes, for example, a base medium known in the art (e.g., DMEM) that is suitable for use (with added supplements) in growing or maintaining the pluripotent and/or totipotent cells (i.e., ES cell, iPS cells, XY ES cells, XY iPS cells, etc.) in culture. Base media suitable for making a fertile XY female (i.e., "low-salt DMEM" or "low-osmolality medium") differs from base media typically used to maintain ES cells in culture. For purposes of discussing base media in general, base media that are not suitable for making fertile XY females are described in this section as "DMEM" and in Table 1 (e.g., typical DMEM media). For purposes of discussing base media suitable for making fertile XY females, the phrase "low-salt DMEM" or "low-osmolality DMEM" is used. Differences between base media typically used to maintain pluripotent and/or totipotent cells in culture (e.g., DMEM) and base media suitable for making fertile XY females (e.g., "low-salt DMEM") are articulated herein. The phrase "low-salt DMEM" is used for convenience; suitable DMEM for making fertile XY females exhibits characteristics not limited to "low-salt," but includes those described herein. For example, the DMEM shown in Table 1 can be made suitable for making fertile XY females by altering the sodium chloride and/or sodium bicarbonate concentrations as provided for herein, which will also result in a different osmolality and a different conductivity as compared with the DMEM shown in Table 1. An example of base medium is Dulbeco's Modified Eagle's Medium (DMEM), in various forms (e.g., Invitrogen DMEM, Cat. No. 1 1971-025) (Table 1). A suitable low-salt DMEM is available commercially as KO-DMEM™ (Invitrogen Cat. No. 10829-018). Base medium is typically supplemented with a number of supplements known in the art when used to maintain cells in culture for use as donor cells. Such supplements are indicated as "supplements" or "+supplements" in this disclosure.

TABLE 1

DMEM Base Media for Maintaining or Culturing Pluripotent and/or Totipotent Cells

| Component | Mg/L | mM |
|---|---|---|
| Glycine | 30 | 0.4 |
| L-Arginine•HCl | 84 | 0.398 |
| L-Cystine•2HCl | 63 | 0.201 |
| L-Glutamine | 584 | 4 |
| L-Histidine•HCl•H2O | 42 | 0.2 |
| L-Isoleucine | 105 | 0.802 |
| L-Leucine | 105 | 0.802 |
| L-Lysine•HCl | 146 | 0.798 |
| L-Methionine | 30 | 0.201 |
| L-Phenylalanine | 66 | 0.4 |
| L-Serine | 42 | 0.4 |
| L-Threonine | 95 | 0.798 |
| L-Tryptophan | 16 | 0.0784 |
| L-Tyrosine disodium salt dihydrate | 104 | 0.398 |

TABLE 1-continued

DMEM Base Media for Maintaining or Culturing Pluripotent and/or Totipotent Cells

| Component | Mg/L | mM |
|---|---|---|
| L-Valine | 94 | 0.803 |
| Choline chloride | 4 | 0.0286 |
| D-Calcium pantothenate | 4 | $8.39 \times 10^{-3}$ |
| Folic Acid | 4 | $9.07 \times 10^{-3}$ |
| Niacinamide | 4 | 0.0328 |
| Pyridoxine•HCl | 4 | 0.0196 |
| Riboflavin | 0.4 | $1.06 \times 10^{-3}$ |
| Thiamine•HCl | 4 | 0.0119 |
| i-Inositol | 7.2 | 0.04 |
| Calcium Chloride (CaCl$_2$) (anhydrous) | 200 | 1.8 |
| Ferric Nitrate (Fe(NO$_3$)$_3$.9H$_2$O) | 0.1 | $2.48 \times 10^{-4}$ |
| Magnesium Sulfate (MgSO$_4$) (anhyd.) | 97.67 | 0.814 |
| Potassium Chloride (KCI) | 400 | 5.33 |
| D-Glucose (Dextrose) | 4500 | 25 |
| Phenol Red | 15 | 0.0399 |
| NaCL/NaHCO$_3$ Content of DMEM | | |
| Sodium Bicarbonate (NaHCO$_3$) | 3700 | 44.05 |
| Sodium Chloride (NaCl) | 6400 | 110.34 |
| NaCl/NaHCO$_3$ Content of Low-salt DMEM | | |
| Sodium Bicarbonate (NaHCO$_3$) | <3700 | <44.05 |
| Sodium Chloride (NaCl) | <6400 | <110.34 |

The term "supplements" or the phrase "+supplements," includes elements added to base medium for growing or maintaining pluripotent and/or totipotent cells (i.e., XY ES cell or XY iPS cells) in culture, e.g., for maintaining pluripotency or totipotency of donor cells in culture. For example, media supplements suitable for growing or maintaining pluripotent and/or totipotent cells in culture include, but are not limited to, fetal bovine serum (FBS), glutamine, antibiotic(s), penicillin and streptomycin (e.g., penstrep), pyruvate salts (e.g., sodium pyruvate), nonessential amino acids (e.g., MEM NEAA), 2-mercaptoethanol, and Leukemia Inhibitory Factor (LIF).

In one embodiment, the base medium comprises one or more supplements suitable for maintaining pluripotent cells in culture, including for example, XY ES cells or XY iPS cells having a reduced capacity to contribute to the male sex determination developmental program after injection into an embryo and intrauterine transfer to a surrogate mother mouse.

In a specific embodiment, the one or more supplements suitable for maintaining the pluripotent cell in culture are FBS (90 ml FBS/0.5 L base medium), glutamine (2.4 mmoles/0.5 L base medium), sodium pyruvate (0.6 mmoles/0.5 L base medium), nonessential amino acids (<0.1 mmol/0.5 L base medium), 2-mercaptoethanol, LIF, and one or more antibiotics.

In other embodiments, the media for maintaining pluripotent cells in culture, including for example, XY ES cells or XY iPS cells having a reduced capacity to contribute to the male sex determination developmental program after injection into an embryo and intrauterine transfer to a surrogate mother mouse, comprises about 500 ml of base medium in which the following supplements are added: about 90 ml FBS (e.g., Hylcone FBS Cat. No. SH30070.03), about 2.4 millimoles of glutamine (e.g., about 12 ml of a 200 mM glutamine solution, e.g., Invitrogen Cat. No. 25030-081, penicillin:streptomycin (e.g., 60,000 units of Penicillin G sodium and 60 mg of streptomycin sulfate, with about 51 mg of NaCl; e.g., about 6 ml. of Invitrogen pennstrep, Cat. No. 15140-122), about 0.6 millimoles of sodium pyruvate (e.g., 6 ml. of 100 mM sodium pyruvate, Invitrogen Cat. No. 1 1360-070), about 0.06 millimoles of nonessential amino acids (e.g., about 6 ml. of MEM NEAA, e.g., MEM NEAA from Invitrogen Cat. No. 1 1 140-050), about 1.2 ml. 2-mercaptoethanol, and about 1.2 micrograms of LIF (e.g., about 120 microliters of a 106 units/mL LIF preparation; e.g., about 120 microliters of Millipore ESGRO™-LIF, Cat. No. ESG1 107). When composing base media for maintaining XY ES or XY iPS cells for making fertile XY females, typically the same supplements in about the same amounts are employed, but the composition of the base medium will differ (from DMEM, e.g., from the medium described in the table above) and the difference(s) correspond to the difference(s) taught herein.

In some embodiments, supplements include Wnt-conditioned media, e.g., Wnt-3a conditioned media.

In one embodiment, the pluripotent cell, including for example, an XY ES cell or an XY iPS cell having a reduced capacity to contribute to the male sex determination developmental program after injection into an embryo and intrauterine transfer to a surrogate mother mouse, is maintained in an in vitro culture in a medium comprising base medium and supplements, wherein the base medium exhibits one or more of the following characteristics: (a) an osmolality from about 200 mOsm/kg to less than about 329 mOsm/kg; (b) a conductivity of about 11 mS/cm to about 13 mS/cm; (c) a salt of an alkaline metal and a halide in a concentration of about 50 mM to about 110 mM; (d) a carbonic acid salt concentration of about 17 mM to about 30 mM; (e) a total alkaline metal halide salt and carbonic acid salt concentration of about 85 mM to about 130 mM; and/or (f) a combination of any two or more thereof. In other embodiments, the XY pluripotent and/or totipotent cells (i.e., XY ES cell or XY iPS cell) is maintained in an in vitro culture in a media as described in WO2011/156723, herein incorporated by reference in its entirety.

In one embodiment, the base medium is a low-salt DMEM. In a specific embodiment, the low-salt DMEM has a NaCl concentration of 85-130 mM. In one embodiment, the base medium is a low osmolality DMEM. In a specific embodiment, the low osmolality DMEM has an osmolality of 250-310 mOsm/kg. In one embodiment, the base medium is a low conductivity DMEM. In a specific embodiment, the low conductivity DMEM has a conductivity of 11-13 mS/cm.

In other embodiments, the base medium exhibits an osmolality of no more than about 320, 310, 300, 290, 280, 275, 270, 260, 250, or 240 mOsm/kg. In one embodiment, the base medium or the medium comprising the base medium and the supplements exhibits an osmolality of no more than about 240-320, 250-310, 275-295, or 260-300 mOsm/kg. In a specific embodiment, the base medium or the medium comprising the base medium and the supplements exhibits an osmolality of about 270 mOsm/kg.

In other embodiments, the base medium exhibits a conductivity of no more than about 10.0, 10.5, 1 1.0, 1 1.5, 12.0, 12.5, 13.0, 13.5, or 14.0 mS/cm. In one embodiment, the base medium exhibits a conductivity of no more than about 10-14 mS/cm or 11-13 mS/cm. In a specific embodiment, the base medium exhibits a conductivity of about 12-13 mS/cm.

In a specific embodiment, the base medium exhibits a conductivity of about 12-13 mS/cm and an osmolality of about 260-300 mOsm/kg. In a further specific embodiment, the base medium comprises sodium chloride at a concentration of about 90 mM NaCl. In a further specific embodiment, the concentration of sodium chloride is about 70-95 mM. In a further specific embodiment, the base medium comprises sodium bicarbonate at a concentration of less than about 35 mM. In a further specific embodiment, the concentration of sodium bicarbonate is about 20-30 mM.

In one embodiment, the base medium exhibits a concentration of a salt of an alkaline metal and a halide of no more than about 100 mM. In one embodiment, the salt of the alkaline metal and the halide is NaCl. In one embodiment, the concentration of the salt of the alkaline metal and halide is no higher than 90, 80, 70, 60, or 50 mM. In one embodiment, the concentration in the base medium of the salt of the alkaline metal and halide is about 60-105, 70-95, or 80-90 mM. In a specific embodiment, the concentration is about 85 mM.

In one embodiment, the base medium exhibits a concentration of a salt of carbonic acid. In one embodiment, the salt of carbonic acid is a sodium salt. In one embodiment, the sodium salt is sodium bicarbonate. In one embodiment, the concentration of carbonic acid salt in the base medium is no higher than 40, 35, 30, 25, or 20 mM. In one embodiment the concentration of carbonic acid salt in the base medium is about 10-40, in another embodiment about 20-30 mM. In a specific embodiment, the concentration is about 25 or 26 mM. In still other embodiments, the sodium bicarbonate concentration is about 26 mM, about 18 mM, about 18 mM to about 26 mM or about 18 mM to about 44 mM.

In one embodiment, the sum of the concentration of the salt of the alkaline metal and halide and the salt of carbonic acid in the base medium is no more than 140, 130, 120, 110, 100, 90, or 80 mM. In one embodiment, the sum of the concentration of the salt of the alkaline metal and halide and the salt of carbonic acid in the base medium is about 80-140, 85-130, 90-120, 95-120, or 100-120 mM. In a specific embodiment, the sum of the concentration of the salt of the alkaline metal and halide and the salt of carbonic acid in the base medium is about 115 mM.

In one embodiment, the molar ratio of the salt of the alkaline metal and halide and the salt of carbonic acid is higher than 2.5. In one embodiment, the ratio is about 2.6-4.0, 2.8-3.8, 3-3.6, or 3.2-3.4. In one embodiment, the ratio is 3.3-3.5. In a specific embodiment, the ratio is 3.4.

In one embodiment, the base medium exhibits an osmolality of about 250-310 mOsm/kg, and a concentration of a salt of an alkaline metal and a halide of about 60-105 mM. In a further embodiment, the base medium has a concentration of a salt of carbonic acid of about 20-30 mM. In a further embodiment, the sum of the concentrations of the salt of an alkaline metal and halide and the salt of carbonic acid is about 80-140 mM. In a further embodiment, the conductivity of the base medium is about 12-13 mS/cm.

In one embodiment, the base medium comprises about 50±5 mM NaCl and about 26±5 mM carbonate, with an osmolality of about 218±22 mOsm/kg. In a specific embodiment, the base medium comprises about 3 mg/mL NaCl and 2.2 mg/mL sodium bicarbonate, with an osmolality of about 218 mOsm/kg.

In another embodiment, the base medium comprises about 87±5 mM NaCl and about 18±5 mM, with an osmolality of about 261±26 mOsm/kg. In a specific embodiment, the base medium comprises about 5.1 mg/mL NaCl and about 1.5 mg/mL sodium bicarbonate, with an osmolality of about 261 mOsm/kg.

In another embodiment, the base medium comprises about 110±5 mM NaCl and about 18±5 mM carbonate, with an osmolality of about 294±29 mOsm/kg. In a specific embodiment, the base medium comprises about 6.4 mg/mL NaCl and about 1.5 mg/mL sodium bicarbonate, with an osmolality of about 294 mOsm/kg.

In another embodiment, the base medium exhibits about 87±5 mM NaCl and about 26±5 mM carbonate, with an osmolality of about 270±27 mOsm/kg. In a specific embodiment, the base medium exhibits about 5.1 mg/mL NaCl and about 2.2 mg/mL sodium bicarbonate, with an osmolality of about 270 mOsm/kg.

In another embodiment, the base medium comprises about 87±5 mM NaCl, about 26±5 mM carbonate, and about 86±5 mM glucose, with an osmolality of about 322±32 mOsm/kg. In a specific embodiment, the base medium comprises about 5.1 mg/mL NaCl, about 2.2 mg/mL sodium bicarbonate, and about 15.5 mg/mL glucose, with an osmolality of about 322 mOsm/kg.

Additional base media that can be employed in the various methods and compositions disclosed herein include, a base medium comprising 50±5 mM NaCl and 26±5 mM carbonate, with an osmolality of 218±22 mOsm/kg. In a particular embodiment, the base medium comprises about 3 mg/mL NaCl and 2.2 mg/mL sodium bicarbonate, with an osmolality of about 218 mOsm/kg.

In other embodiments, the base medium comprises 50±5 mM NaCl and 26±5 mM carbonate, with an osmolality of 218±22 mOsm/kg. In a specific embodiment, the base medium comprises about 3 mg/mL NaCl and 2.2 mg/mL sodium bicarbonate, with an osmolality of about 218 mOsm/kg.

In other embodiments, high glucose DMEM media (LifeTech) with $NaHCO_3$ concentrations as disclosed herein, including, about 44 mM, 26 mM or 18 mM, were supplemented with 0.1 mM nonessential amino acids, 1 mM sodium pyruvate, 0.1 mM 2-mercaptoethanol, 2 mM L-glutamine, 50 ug/ml each penicillin and streptomycin (LifeTech), 15% FBS (Hyclone), and 2000 U/ml LIF (Millipore).

C. Method for Making Targeted Genetic Modifications

Various methods for making targeted genetic modifications that decrease the level and/or the activity of the Sry protein can be used. For example, in one instance, the targeted genetic modification employs a system that will generate a targeted genetic modification via a homologous recombination event. In other instances, the animal cell can be modified using nuclease agents that generate a single or double strand break at a targeted genomic location. The single or double-strand break is then repaired by the non-homologous end joining pathway (NHEJ). Such systems find use, for example, in generating targeted loss of function genetic modifications. Non-limiting methods for generating such targeted genetic modification are discussed in detail elsewhere herein, including, for example, the use of targeting plasmids, small targeting vectors (smallTVECs) or large targeting vectors. See, also, Wang et al. (2013) *Cell* 153: 910-918, Mandalos et al. (2012) *PLOS ONE* 7:e45768:1-9, and Wang et al. (2013) *Nat Biotechnol.* 31:530-532, each of which is herein incorporated by reference.

It is recognized that in specific embodiments, the targeted genetic modification of the Sry gene and/or the targeted genetic modification of any other polynucleotide of interest can occur while the pluripotent cell (i.e., ES cell) is being maintained in the culture media described herein (e.g. a medium that promotes the development of XY F0 fertile females). Alternatively, the targeted genetic modification of the Sry gene and/or any other polynucleotide of interest can occur while the pluripotent cell (i.e., ES cell) is being maintained in different culture media, and subsequently transferred to the culture media disclosed herein (e.g. a medium that promotes the development of XY F0 fertile females).

D. Method of Culturing and Maintaining a Pluripotent and/or Totipotent Cell in Culture A method for maintaining or culturing an XY pluripotent and/or totipotent cell (i.e., an XY ES cell or an XY iPS cell) in an in vitro culture is provided, wherein the cell comprises a modification that decreases the level and/or activity of an Sry protein and the cell is maintained in an in vitro culture under conditions described herein. Such methods of maintaining or culturing an XY pluripotent and/or totipotent cell (i.e., an XY ES cell or an XY iPS cell) in an in vitro culture is such as to promote an increase in the number XY F0 fertile female animals upon the introduction of the non-human animal XY ES cells into a host embryo and following gestation of the host embryos.

While any media disclosed herein can be employed for such maintaining or culturing methods, one non-limiting example, includes culturing in a medium comprising a base medium and supplements suitable for maintaining or culturing the XY pluripotent and/or totipotent cell (i.e., an XY ES cell or an XY iPS cell) in culture, wherein the base medium or the medium comprising the base medium and the supplements exhibits an osmolality from about 200 mOsm/kg to less than about 329 mOsm/kg.

In some embodiments, the base medium or the medium comprising the base medium and the supplements exhibits one or more of the following characteristic: a conductivity of about 11 mS/cm to about 13 mS/cm; a salt of an alkaline metal and a halide in a concentration of about 50 mM to about 110 mM; a carbonic acid salt concentration of about 17 mM to about 30 mM; a total alkaline metal halide salt and carbonic acid salt concentration of about 85 mM to about 130 mM; and/or a combination of any two or more thereof.

In one embodiment, the method comprises maintaining or culturing the XY pluripotent and/or totipotent cell (i.e., an XY ES cell or an XY iPS cell) in a suitable culture medium that comprises a base medium and supplements, wherein the base medium or the medium comprising the base medium and the supplements comprises an osmolality of about 240-320 mOsm/kg, a conductivity of about 10-14 mS/cm, an alkaline metal halide salt concentration of about 50-105 mM, a salt of carbonic acid concentration of 10-40 mM, and/or a combined alkaline metal salt and carbonic acid salt concentration of about 80-140 mM. In one embodiment, the XY pluripotent and/or totipotent cell (i.e., an XY ES cell or an XY iPS cell) is maintained in the medium (with supplements for maintaining ES cells) for a period of 1, 2, 3, 4, 5, 6, 7, 8, 9, 10, 11, 12, or 13 days, or 2 weeks, 3 weeks, or 4 weeks prior to introduction into a host embryo. In a specific embodiment, the XY pluripotent and/or totipotent cell (i.e., an XY ES cell or an XY iPS cell) is maintained in the medium (low-salt base medium with supplements for maintaining ES cells) for about 2-4 weeks prior to introduction into the host embryo.

In another embodiment, the XY pluripotent and/or totipotent cell (i.e., an XY ES cell or an XY iPS cell) is maintained in a medium with a low-salt base medium for at least 1, 2, 3, 4, 5, 6, 7, 8, 9, 10, 11, or 12 days, 2 weeks, 3 weeks, or 4 weeks prior to introducing the donor cell into a host embryo. In a specific embodiment, the XY pluripotent and/or totipotent cell (i.e., an XY ES cell or an XY iPS cell) is maintained in a medium with a low-salt base medium at least 2-4 weeks prior to introduction of the cell into the host embryo.

In another embodiment, the XY pluripotent and/or totipotent cell (i.e., an XY ES cell or an XY iPS cell) is maintained (e.g., frozen) in a medium that promotes XY fertile F0 females and the donor cell is thawed in and maintained in the medium that promotes XY fertile F0 females for at least 1, 2, 3, or 4 or more days before introducing the XY pluripotent and/or totipotent cell (i.e., an XY ES cell or an XY iPS cell) into the host embryo. In a specific embodiment, the XY pluripotent and/or totipotent cell (i.e., an XY ES cell or an XY iPS cell) is passaged at least once in a medium that promotes XY fertile F0 females, the cell is frozen in the medium that promotes XY fertile F0 females, and the cell is thawed in a medium that promotes XY fertile F0 females and grown for 1, 2, 3, 4, 5, 6, 7, 8, 9, 10, 11, 12, or 13 days, 2 weeks, 3 weeks, 4 weeks, or more prior to introduction into the host embryo.

In still another embodiment, the XY pluripotent and/or totipotent cell (i.e., an XY ES cell or an XY iPS cell) is maintained in the medium that promotes XY fertile F0 females for a period of one, two, three, or four days prior to introduction into a host embryo. In one embodiment, the XY pluripotent and/or totipotent cell (i.e., an XY ES cell or an XY iPS cell) is maintained in the medium that promotes XY fertile F0 females for a period of 3 days.

In one embodiment, the XY pluripotent and/or totipotent cell (i.e., an XY ES cell or an XY iPS cell) is maintained the medium that promotes XY fertile F0 females before introduction into the host embryo for about 1, 2, 3, 4, 5, 6, 7, 8, 9, 10, 11, or 12 days, 2 weeks, 3 weeks, or 4 weeks or more. In a specific embodiment, the donor cell is maintained in the medium that promotes XY fertile F0 females for at least a week before introduction into the host embryo. In a specific embodiment, the XY pluripotent and/or totipotent cell (i.e., an XY ES cell or an XY iPS cell) is maintained in the medium that promotes XY fertile F0 females for 2-4 weeks before introduction into the host embryo.

Thus, a method for maintaining or culturing an XY pluripotent and/or totipotent cell (i.e., an XY ES cell or an XY iPS cell) in culture is provided, wherein the cell is maintained under conditions that promote or favor development of a female XY animal following introduction of the XY cell into a host embryo and following gestation in a suitable female host.

In one aspect, a method for maintaining or culturing a donor XY pluripotent and/or totipotent cell (i.e., an XY ES cell or an XY iPS cell) in culture is provided, under conditions as described herein, wherein following introduction of the donor XY ES cell into a host embryo to form a F0 embryo and gestation of the F0 embryo in a suitable animal, the F0 embryo develops into an F0 animal that is at least 70%, 75%, 80%, 85%, 90%, 91%, 92%, 93%, 94%, 95%, 96%, 97%, 98%, 99% or greater XY and is a female which, upon attaining sexual maturity, is fertile.

E. Generating F0 Embryos and F1 Progeny Having a Targeted Genetic Modification

The various methods and compositions employing the XY pluripotent and/or totipotent cell (i.e., an XY ES cell or an XY iPS cell) having a decreased level and/or activity of Sry protein provided herein can be used to generate a genetically modified animal. Various methods for introducing genetic modifications are discussed in detail elsewhere herein.

i. Method for Making a Fertile Female XY Non-Human Animal in an F0 Generation

A method for making a fertile female XY non-human animal in an F0 generation is provided. Such methods comprise: (a) maintaining or culturing a donor non-human animal XY pluripotent and/or totipotent cell (i.e., an XY ES cell or an XY iPS cell) having a modification that decreases the level and/or activity of an Sry protein in a medium that promotes the development of XY fertile female ES cells; (b) introducing the donor XY non-human animal XY pluripotent and/or totipotent cell (i.e., an XY ES cell or an XY iPS cell) into a host embryo; (c) gestating the host embryo; and, (d) obtaining an F0 XY female non-human animal, wherein upon attaining sexual maturity the F0 XY female non-human animal is fertile. In specific embodiments, the donor non-human animal XY donor cell can comprise at least one additional targeted genetic modification in a polynucleotide of interest. Such modifications are discussed in detail elsewhere herein.

The XY ES cells having a modification that decreases the level and/or activity of an Sry protein can be maintained without a low-salt medium and can develop into an XY fertile female.

In some embodiments, the medium that promotes the development of XY fertile F0 female animals can comprise a low-salt based medium which comprises a base medium and supplements suitable for maintaining or culturing the non-human mammalian ES cell in culture, wherein the low-salt base medium exhibits a characteristic comprising one or more of the following: an osmolality from about 200 mOsm/kg to less than about 329 mOsm/kg; a conductivity of about 11 mS/cm to about 13 mS/cm; a salt of an alkaline metal and a halide in a concentration of about 50 mM to about 110 mM; a carbonic acid salt concentration of about 17 mM to about 30 mM; a total alkaline metal halide salt and carbonic acid salt concentration of about 85 mM to about 130 mM; and/or a combination of any two or more thereof.

In other embodiments, such methods for making a fertile female XY non-human animal in an F0 generation can be performed using the mediums disclosed herein including, but not limited to, (a) a base medium comprising 50±5 mM NaCl, 26±5 mM carbonate, and 218±22 mOsm/kg; (b) a base medium comprising about 3 mg/mL NaCl, 2.2 mg/mL sodium bicarbonate, and 218 mOsm/kg; (c) a base medium comprising 87±5 mM NaCl, 18±5 mM carbonate, and 261±26 mOsm/kg; (d) a base medium comprising about 5.1 mg/mL NaCl, 1.5 mg/mL sodium bicarbonate, and 261 mOsm/k; (e) a base medium comprises 110±5 mM NaCl, 18±5 mM carbonate, and 294±29 mOsm/kg; (f) a base medium comprises about 6.4 mg/mL NaCl, 1.5 mg/mL sodium bicarbonate, and 294 mOsm/kg; (g) a base medium comprises 87±5 mM NaCl, 26±5 mM carbonate, and 270±27 mOsm/kg; (h) a base medium comprises about 5.1 mg/mL NaCl, 2.2 mg/mL sodium bicarbonate, and 270 mOsm/kg; (i) a base medium comprises 87±5 mM NaCl, 26±5 mM carbonate, 86±5 mM glucose, and 322±32 mOsm/kg; and/or (j) a base medium comprises about 5.1 mg/mL NaCl, 2.2 mg/mL sodium bicarbonate, 15.5 mg/mL glucose, and 322 mOsm/kg.

The genetically modified XY pluripotent and/or totipotent cell (i.e., an XY ES cell or an XY iPS cell) having a modification that decreases the level and/or activity of an Sry protein and having been cultured in the medium that promotes the development of XY F0 fertile females can be implanted into a host embryo. Cells that have been implanted into a host embryo are referred to herein as "donor cells." In specific embodiments, the genetically modified XY pluripotent and/or totipotent cell (i.e., an XY ES cell or an XY iPS cell) is from the same strain as the host embryo or from a different strain as the host embryo. Likewise, the surrogate mother can be from the same strain as the genetically modified XY pluripotent and/or totipotent cell (i.e., an XY ES cell or an XY iPS cell) and/or the host embryo, or the surrogate mother can be from a different strain as the genetically modified XY pluripotent and/or totipotent cell (i.e., an XY ES cell or an XY iPS cell) and/or the host embryo. In one embodiment, the XY donor cell is implanted into an XX host embryo.

A variety of host embryos can be employed in the methods and compositions disclosed herein. In some embodiments, the XY pluripotent and/or totipotent cells (i.e., the XY ES cell or the XY iPS cell) having the targeted genetic modification resulting in a decreased level and/or activity of the Sry protein are introduced into a pre-morula stage embryo from a corresponding organism, e.g., an 8-cell stage embryo. See, e.g., U.S. Pat. No. 7,576,259, U.S. Pat. No. 7,659,442, U.S. Pat. No. 7,294,754, and US 2008-0078000 A1, all of which are incorporated by reference herein in their entireties. In other embodiments, the donor ES cells may be implanted into a host embryo at the 2-cell stage, 4-cell stage, 8-cell stage, 16-cell stage, 32-cell stage, or 64-cell stage host embryo. In another embodiment, the host embryo is a blastocyst. In one embodiment, the host embryo is in a stage selected from a pre-blastocyst embryo, a pre-morula stage, a morula stage, an uncompacted morula stage, and a compacted morula stage. In one embodiment, when employing a mouse embryo, the host embryo stage is selected from a Theiler Stage 1 (TS1), a TS2, a TS3, a TS4, a TS5, and a TS6, with reference to the Theiler stages described in Theiler (1989) "The House Mouse: Atlas of Mouse Development," Springer-Verlag, New York. In a specific embodiment, the Theiler Stage is selected from TS1, TS2, TS3, and a TS4. In one embodiment, the host embryo comprises a zona pellucida, and the donor cell is an XY ES cell that is introduced into the host embryo through a hole in the zona pellucida, while in other embodiments, the host embryo is a zona-less embryo. In yet other specific embodiments, the morula-stage host embryo is aggregated.

Nuclear transfer techniques can also be used to generate the genetically modified animals. Briefly, methods for nuclear transfer include the steps of: (1) enucleating an oocyte; (2) isolating a donor cell or nucleus to be combined with the enucleated oocyte; (3) inserting the cell or nucleus into the enucleated oocyte to form a reconstituted cell; (4) implanting the reconstituted cell into the womb of an animal to form an embryo; and (5) allowing the embryo to develop. In such methods oocytes are generally retrieved from deceased animals, although they may be isolated also from either oviducts and/or ovaries of live animals. Oocytes can be matured in a variety of medium known to those of ordinary skill in the art prior to enucleation. Enucleation of the oocyte can be performed in a number of manners well known to those of ordinary skill in the art. Insertion of the donor cell or nucleus into the enucleated oocyte to form a reconstituted cell is usually by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell is typically activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, are typically cultured in medium well known to those of ordinary skill in the art and then transferred to the womb of an animal. See, for example, US20080092249, WO/1999/005266A2, US20040177390, WO/2008/017234A1, and U.S. Pat. No. 7,612,250, each of which is herein incorporated by reference.

The host embryo comprising the genetically modified XY pluripotent and/or totipotent cell (i.e., an XY ES cell or an XY iPS cell) having the decreased level and/or activity of the Sry protein is incubated until the blastocyst stage and then implanted into a surrogate mother to produce an F0 animal. Animals bearing the genetically modified genomic locus can be identified via modification of allele (MOA) assay as described herein.

In one embodiment, the host embryo comprising the genetically modified XY pluripotent and/or totipotent cells (i.e., an XY ES cell or an XY iPS cell) having the decreased level and/or activity of the Sry protein is maintained in a medium that promotes the development of XY fertile female ES cells (i.e., a low-salt base medium) for one, two, three, or four or more days prior to implantation in a suitable host. Such methods provide for favoring the generation of an F0 fertile female animal.

In one embodiment, the cultured host embryo is implanted into a surrogate mother, and the cultured host embryo is gestated in the surrogate mother.

In specific embodiments, upon introduction of the non-human animal XY pluripotent and/or totipotent cells (i.e., an XY ES cell or an XY iPS cell) into a host embryo and following gestation of the host embryo, at least 15%, 20%, 30%, 40%, 50%, 60%, 70%, 75%, 80% 85%, 90%, 91%, 92%, 93%, 94%, 95%, 96%, 97%, 98%, 99% or 100% of the F0 non-human animals are XY females which upon attaining sexual maturity the F0 XY female non-human mammal is fertile.

Further provided is an F0 embryo comprising an inner cell mass having at least one heterologous stem cell comprising an XY ES cell or XY iPS cell having a targeted genetic modification that decreases the level and/or activity of the Sry protein.

The various methods described herein to generate a fertile female XY non-human animal in an F0 generation can employ XY pluripotent and/or totipotent cells (i.e., an XY ES cell or an XY iPS cell) having (1) the genetic modification to reduce the level and/or activity of the Sry polypeptide; and, in specific embodiments, (2) one or more additional targeted genetic modification in a polynucleotide of interest. As outlined elsewhere herein, at least 1, 2, 3, 4, 5, 6, 7, 8, 9, 10 or more additional targeted genetic modifications can be made in the XY pluripotent and/or totipotent cell (i.e., an XY ES cell or an XY iPS cell). In such instances, the F0 fertile female XY non-human animal can comprises one or more of these additional targeted genetic modifications.

In other embodiments, the F0 fertile female XY non-human animal produces 1, 2, 3, 4, 5, 6, 7, 8, or 9 litters during its lifetime. In one embodiment, the F0 fertile female XY non-human animal produces at least 1, 2, 3, 4, 5, 6, 7, 8, 9, or 10 offspring per litter. In one embodiment, the F0 fertile female XY non-human animal produces about 4-6 offspring per litter. In one embodiment, the F0 fertile female XY non-human animal produces 2-6 litters, wherein each litter has at least 2, 3, 4, 5, or 6 offspring. In one embodiment, at least about 10%, 15%, 20%, 25%, 30%, 35%, 40%, 45%, 50%, 60%, 70%, 80%, 85%, 90%, 95% or 100% of the offspring are XY fertile female offspring.

A method for generating a rodent litter (i.e., a mouse or a rat litter) is also provided and comprises introducing an XY pluripotent and/or totipotent donor cell (i.e., an XY donor ES cell or XY donor iPS cell) having the decreased level and/or activity of Sry protein prepared according to the methods set forth herein into host embryos, gestating the embryos in a suitable segregate mother, and obtaining F0 progeny that comprises at least one XY female rodent that upon reaching sexual maturity is a fertile XY female rodent. In one embodiment, the percentage of F0 XY female rodents born that upon reaching sexual maturity are fertile is about 10%, 15%, 20%, 25%, 30%, 35%, 40%, 45%, 50%, 60%, 70%, 75%, 80%, 85%, 95% or 100%.

In other embodiments, the F0 progeny produced from such methods are about 3%, about 10% or more, or about 63% or more derived from the genetically modified donor XY cell.

The methods and compositions provided herein allow for at least 1%, 3%, 5%, 10%, 15%, 20%, 25%, 30%, 35%, 40%, 45%, 50%, 55%, 60%, 65%, 70%, 75% or greater of the F0 animals to have the targeted genetic modification (i.e., the decrease in Sry protein level and/or activity and/or the targeted genetic modification to a polynucleotide of interest) to transmit the genetic modification to the F1 progeny.

In one embodiment, the F0 generation female XY non-human animal and/or the male XY non-human animal is at least 90%, 92%, 94%, 96%, 98%, 99%, or 99.8% derived from the donor cell. In one embodiment, the F0 female XY non-human animal and/or the F0 male XY non-human animal has a coat color that is 100% derived from the donor cell.

In one embodiment, the non-human female XY animal in the F0 generation is a rodent (i.e., a mouse or a rat) and has a coat color 100% derived from the donor cell. In one embodiment, the non-human female XY non-human animal formed in the F0 generation is at least 90%, 92%, 94%, 96%, 98%, or 99.8% derived from the XY donor cell. In one embodiment, the non-human female XY animal in the F0 generation is about 100% derived from the donor cell. In one embodiment, the contribution of a host embryo cell to the non-human female XY animal in the F0 generation is determined by a quantitative assay that is capable of detecting 1 cell in 2,000 (0.05%), and no tissue of the female XY animal is positive for host embryo cell contribution.

ii. Various Methods of Breeding the Female Fertile XY F0 Generation

In specific embodiments, the resulting female fertile XY F0 generation derived from the XY pluripotent and/or totipotent cells (i.e., the XY ES cell or XY iPS cell) having the genetic modification that decreases the level and/or activity of the Sry protein is crossed to an animal to obtain F1 generation offspring. In specific embodiments, the female fertile XY F0 is crossed to a wild type animal. In one embodiment, the female XY F0 non-human mammal is fertile when crossed to a wild type mouse. In specific embodiments, the wild type mouse is C57BL/6. The F1 progeny can be genotyped using specific primers and/or probes to determine if the targeted genetic modification comprising the decreased level and/or activity of the Sry protein is present. Moreover, if additional targeted genetic modifications were present in the F0 generation, the F1 progeny can be genotyped using specific primers and/or probes that determine if such modifications are present. An appropriate F1 progeny for a desired use can then be identified. In specific embodiments, F1 progeny lacking the genetic modification that reduced the level and/or activity of the Sry protein are selected. In other embodiments, F1 progeny lacking the genetic modification that reduced the level and/or activity of the Sry protein and which comprise at least one additional targeted genetic modification are selected.

In one non-limiting example, following genotyping with specific primers and/or probes, F1 animals that are heterozygous for the targeted genetic modification to the polynucleotide of interest and lacking the targeted modification that reduces the level and/or activity of the Sry protein are crossed to one another. Such a cross produces an F2 progeny that is homozygous for the genetically modified genomic locus of interest and does not comprise the genetic modification to reduce Sry protein levels and/or activity.

Further provided is a method of producing a transgenic non-human animal homozygous for a targeted genetic modification in the F1 generation. The method comprises (a) crossing an F0 XY fertile female non-human animal having a targeted genetic modification that decreases the level and/or activity of the Sry protein with a F0 XY male non-human animal, wherein the F0 XY fertile female non-human animal and the F0 XY male non-human animal are each heterozygous for the same genetic modification of a polynucleotide of interest, and (b) obtaining an F1 progeny that is homozygous for the targeted genetic modification in the polynucleotide of interest. In a specific embodiment, the F1 progeny selected are homozygous for the targeted genetic modification in the polynucleotide of interest and lack the targeted genetic modification that decreases the activity and/or level of the Sry protein. Such methods can be employed to develop breeding pairs of non-human animals, each fully derived from a donor ES cell or iPS cell, in the same F0 generation.

Various methods can be employed to obtain the F0 animals described above. In one non-limiting embodiment, an XY cell clone with a targeted modification in a polynucleotide of interest on any chromosome is isolated. It is recognized that various methods can be used to generate the targeted modification in the polynucleotide of interest. In a second step, a targeted modification is introduced into the Sry gene such that the modification decreases the level and/or activity of the Sry protein. Such methods will further employ culturing the XY ES cell in a media that promotes the development of XY F0 fertile females, as describe in detail elsewhere herein. Methods of targeted modification of the Sry gene are disclosed in detail elsewhere herein and can comprise, for example, the use of a targeting vector (including an LTVEC) either alone or in combination with a nuclease as described elsewhere herein (i.e., a Talen or CRISPR- or ZFN-system). A subclone is isolated that comprises both the first targeted modification in the polynucleotide of interest and the second targeted modification of the Sry gene that decreases the level and/or activity of the Sry protein. Both the original XY clone with the targeted modification in the polynucleotide of interest and the XY subclone comprising both the targeted modification to the Sry gene and the polynucleotide of interest are introduced into separate non-human host embryos, as discussed elsewhere herein. In specific embodiments, the non-human host embryos comprise a pre-morula embryo (i.e., an 8 cell stage embryo). Each of the non-human host embryos comprising the modified pluripotent cells is introduced into a surrogate mother for gestation. Each of the surrogate mothers produces F0 progeny comprising the targeted genome modification (i.e., an F0 XY male having the targeted modification in the polynucleotide of interest and an F0 XY fertile female having the targeted modification in the polynucleotide of interest and having the genetic modification that decreases the level and/or activity of the Sry protein). In specific embodiments, each of the targeted genomic modifications is capable of being transmitted through the germline. Each of these F0 animals are bred to one another, to generate an F1 animal comprising a homozygous targeted modification in the polynucleotide of interest. One-quarter of the F1 generation are expected to be homozygous for the targeted modification in the polynucleotide of interest. F1 progeny can be selected to retain the targeted modification to the Sry gene or the F1 progeny can be selected to not retain the targeted modification to the Sry gene.

In another embodiment, the introduction of the targeted modification of the Sry gene employing a targeting vector (and, in specific embodiments, nucleases such as Talen, Crispr, or Zfn) can occur simultaneously with the vector targeting for the genetic modification of the polynucleotide of interest. Such methods allow for the generation of an XY ES cell having both a genetic modification that decreases the level and/or activity of the Sry protein and further comprises the targeted modification to the polynucleotide of interest.

In one embodiment, the F1 generation progeny comprises a genome completely derived from the donor ES cell. In other embodiments, the frequency of crosses of F0 generation male and F0 generation female mice that give rise to fully ES cell-derived mice is 100%.

II. Methods and Compositions for Modifying a Challenging Target Genomic Locus or a Target Genomic Locus on the Y Chromosome Methods and compositions are provided that allow for modifying a target genomic locus on the Y chromosome in a cell. Further provided are methods that allow for modifying a "challenging" genomic locus. The term "challenging locus" includes a chromosomal region that is difficult to target by conventional gene targeting strategies. Such loci can be located on the Y chromosome, the X chromosome, or an autosome. In certain embodiments, challenging loci are located within or in proximity to gene-poor, repeat-rich, and/or largely heterochromatic chromosomal regions. See, e.g., Bernardini et al., *Proc. Natl. Acad. Sci. USA* 111:7600-7605 (2014), herein incorporated by reference in its entirety for all purposes. In certain embodiments, a challenging locus is located within or in proximity to chromosomal regions in which accessibility of the chromosomal DNA is limited by chromatin structure. In certain embodiments, a challenging locus is within or in proximity to chromosomal regions characterized by a high percentage of heterochromatin, such as at least about ~20%, at least about ~30%, at least about 40%, at least about 50%, at least about 60%, or at least about 70% heterochromatin. In certain embodiments, a challenging locus is located within or in proximity to chromosomal regions that have undergone duplications and rearrangements or that are characterized by the presence of repeats or inverted repeats. See, e.g., Gubbay et al., *Proc. Natl. Acad. Sci. USA* 89:7953-7957 (1992), herein incorporated by reference in its entirety for all purposes.

The term "chromatin" includes nucleoprotein complexes which compact and organize cellular genetic material to contain it within cells. The term "heterochromatin" includes regions in the genome that are in a highly condensed state and are generally transcriptionally silent. Heterochromatin is generally more tightly coiled and generally has more repetitive DNA sequences than euchromatin. The term "euchromatin" includes regions in the genome characterized by more extended and less condensed chromatin domains that are often transcriptionally active and accessible.

The term "exposing" includes using any method by which desired components are brought into immediate proximity or direct contact.

Methods and compositions are provided that allow for modifying a challenging target genomic locus or a target genomic locus on the Y chromosome in a cell. Perhaps due to unique structural features of the Y chromosome, conventional gene targeting strategies in mouse embryonic stem cells to generate mutations on the Y-linked genes has had limited success. Therefore, often the understanding of the functions of murine Y-linked genes is limited to insights gained from studies of mice that carry spontaneous deletions, random gene trap insertions or autosomal transgenes. Methods provided herein allow for the targeting of a genomic locus on the Y chromosome by employing a targeting vector in the absence of or in combination with a nuclease agent.

Some such methods utilize a small targeting vector or smallTVEC. A "smallTVEC" includes a targeting vector that comprises short homology arms. The length of a homology arm on a smallTVEC can be from about 400-1000 bp. A homology arm of the smallTVEC can be of any length that is sufficient to promote a homologous recombination event with a corresponding target site, including for example, from about 400 bp to about 500 bp, from about 500 bp to about 600 bp, from about 600 bp to about 700 bp, from about 700 bp to about 800 bp, from about 800 bp to about 900 bp, or from about 900 bp to about 1000 bp. A preferred length of a homology arm on a smallTVEC is from about 700 bp to about 800 bp. In another embodiment, the sum total of 5' and 3' homology arms of the smallTVEC is about 0.5 kb, 1 kb, 1.5 kb, 2 kb, 3 kb, 4 kb, 5 kb, 6 kb, 7 kb, 8 kb, 9 kb, about 0.5 kb to about 1 kb, about 1 kb to about 1.5 kb, about 1.5 kb to about 2 kb, about 2 kb to about 3 kb, about 3 kb to about 4 kb, about 4 kb to about 5 kb, about 5 kb to about 6 kb, about 6 kb to about 7 kb, about 8 kb to about 9 kb, or is at least 10 kb. In such methods, the short length of the homology arms increases the targeting efficiency as compared to a targeting vector with longer homology arms. Due to the nature of the Y chromosome which has highly repetitive sequences, the short arms of the smallTVECs allow for highly specific targeting on the Y chromosome.

Methods are provided for modifying a target genomic locus on the Y chromosome in a cell comprising: (a) providing a cell comprising a target genomic locus on the Y chromosome comprising a recognition site for a nuclease agent, (b) introducing into the cell a first targeting vector comprising a first insert polynucleotide flanked by a first and a second homology arm corresponding to a first and a second target site; and (c) identifying at least one cell comprising in its genome the first insert polynucleotide integrated at the target genomic locus on the Y chromosome. In specific embodiments, the sum total of the first homology arm and the second homology arm of the targeting vector is about 0.5 kb, 1 kb, 1.5 kb, 2 kb, 3 kb, 4 kb, 5 kb, 6 kb, 7 kb, 8 kb, 9 kb, about 0.5 kb to about 1 kb, about 1 kb to about 1.5 kb, about 1.5 kb to about 2 kb, about 2 kb to about 3 kb, about 3 kb to about 4 kb, about 4 kb to about 5 kb, about 5 kb to about 6 kb, about 6 kb to about 7 kb, about 8 kb to about 9 kb, or is at least 10 kb or at least 10 kb and less than 150 kb. In some embodiments, a smallTVEC is employed. In specific embodiments, an LTVEC is employed. Similar methods can be performed when targeting a challenging target genomic locus. In one non-limiting embodiment, such methods are performed employing the culture media that promotes the development of XY F0 fertile females disclosed herein and thereby generating XY F0 fertile female animals. In other instance, the methods described herein are employed to produce a targeted genetic modification in the Sry gene, as discussed elsewhere herein.

Further provided are methods for modifying a target genomic locus on the Y chromosome in a cell comprising: (a) providing a cell comprising a target genomic locus on the Y chromosome comprising a recognition site for a nuclease agent, (b) introducing into the cell (i) the nuclease agent, wherein the nuclease agent induces a nick or double-strand break at the first recognition site; and, (ii) a first targeting vector comprising a first insert polynucleotide flanked by a first and a second homology arm corresponding to a first and a second target site located in sufficient proximity to the first recognition site; and (c) identifying at least one cell comprising in its genome the first insert polynucleotide integrated at the target genomic locus on the Y chromosome. In specific embodiments, the sum total of the first homology arm and the second homology arm of the targeting vector is about 0.5 kb, 1 kb, 1.5 kb, 2 kb, 3 kb, 4 kb, 5 kb, 6 kb, 7 kb, 8 kb, 9 kb, about 0.5 kb to about 1 kb, about 1 kb to about 1.5 kb, about 1.5 kb to about 2 kb, about 2 kb to about 3 kb, about 3 kb to about 4 kb, about 4 kb to about 5 kb, about 5 kb to about 6 kb, about 6 kb to about 7 kb, about 8 kb to about 9 kb, or is at least 10 kb or at least 10 kb and less than 150 kb. In some embodiments, a smallTVEC is employed. In specific embodiments, an LTVEC is employed. Similar methods can be performed when targeting a challenging target genomic locus. In one non-limiting embodiment, such methods are performed employing the culture media that promotes the development of XY F0 fertile females disclosed herein and thereby generating XY F0 fertile female animals. In other instance, the methods described herein are employed to produce a targeted genetic modification in the Sry gene, as discussed elsewhere herein.

It is recognized that the various methods disclosed herein to generate a targeted modification in a genomic locus of the Y chromosome (or any challenging genomic locus) employing a targeting vector, a smallTVEC, or an LTVEC can be performed in any cell type, and is not limited to an XY pluripotent and/or totipotent cell. Such cell types include, but are not limited to, a human cell, a non-human cell, a mammalian cell, non-human mammalian cell, a rodent cell, a mouse cell, a rat cell, a hamster cell, a fibroblast cell or any other host cell. Such cells include pluripotent cells, including, for example, induced pluripotent stem (iPS) cells, mouse embryonic stem (ES) cells, rat embryonic stem (ES) cells, human embryonic (ES) cells, or developmentally restricted human progenitor cells.

Methods are further disclosed to generate a large deletion on the Y chromosome employing any of the various nuclease agents provided herein (e.g., CRISPR gRNAs in combination with Cas9; ZFNs; or TALENs). Such a deletion on the Y chromosome can be a deletion of an endogenous nucleic acid sequence. The deletion can range from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 300 kb, from about 300 kb to about 400 kb, from about 400 kb to about 500 kb, from about 500 kb to about 600 kb, from about 600 kb to about 700 kb, from about 700 kb to about 800 kb, from about 800 kb to about 900 kb, from about 900 kb to about 1 Mb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb. In one embodiment, the deletion is greater than 500 kb. In another embodiment, the deletion is from about 500 kb to about 600 kb. In a specific embodiment, the deletion is about 500 kb. Such a deletion on the Y chromosome can be a deletion of any nucleic acid sequence. In one embodiment, the deletion comprises a gene that is associated with fertility/infertility. The deletion on the Y chromosome can comprise a deletion of multiple genes. In such methods, 1, 2, 3, 4, 5, 6, 7, 8, 9, 10 or more genes can be deleted. In specific embodiments, the Kdm5d gene (Lysine (K)-specific demethylase 5d; for example, Entrez Gene ID 20592 (*mus musculus*)) and/or the Usp9y gene (ubiquitin specific peptidase 9, y-linked; for example, Entrez Gene ID 107868(*mus musculus*)) is targeted for deletion. In other embodiments, the Sry gene is targeted for deletion.

A. Nuclease Agents and Recognition Sites for Nuclease Agents

The term "recognition site for a nuclease agent" includes a DNA sequence at which a nick or double-strand break is induced by a nuclease agent. The recognition site for a nuclease agent can be endogenous (or native) to the cell or the recognition site can be exogenous to the cell. In specific embodiments, the recognition site is exogenous to the cell and thereby is not naturally occurring in the genome of the cell. In still further embodiments, the recognition site is exogenous to the cell and to the polynucleotides of interest that one desires to be positioned at the target locus. In further embodiments, the exogenous or endogenous recognition site is present only once in the genome of the host cell. In specific embodiments, an endogenous or native site that occurs only once within the genome is identified. Such a site can then be used to design nuclease agents that will produce a nick or double-strand break at the endogenous recognition site.

The length of the recognition site can vary, and includes, for example, recognition sites that are about 30-36 bp for a zinc finger nuclease (ZFN) pair (i.e., about 15-18 bp for each ZFN), about 36 bp for a Transcription Activator-Like Effector Nuclease (TALEN), or about 20 bp for a CRISPR/Cas9 guide RNA.

In one embodiment, each monomer of the nuclease agent recognizes a recognition site of at least 9 nucleotides. In other embodiments, the recognition site is from about 9 to about 12 nucleotides in length, from about 12 to about 15 nucleotides in length, from about 15 to about 18 nucleotides in length, or from about 18 to about 21 nucleotides in length, and any combination of such subranges (e.g., 9-18 nucleotides). It is recognized that a given nuclease agent can bind the recognition site and cleave that binding site or alternatively, the nuclease agent can bind to a sequence that is different from the recognition site. Moreover, the term recognition site comprises both the nuclease agent binding site and the nick/cleavage site irrespective whether the nick/cleavage site is within or outside the nuclease agent binding site. In another variation, the cleavage by the nuclease agent can occur at nucleotide positions immediately opposite each other to produce a blunt end cut or, in other cases, the incisions can be staggered to produce single-stranded overhangs, also called "sticky ends", which can be either 5' overhangs, or 3' overhangs.

Any nuclease agent that induces a nick or double-strand break into a desired recognition site can be used in the methods and compositions disclosed herein. A naturally-occurring or native nuclease agent can be employed so long as the nuclease agent induces a nick or double-strand break in a desired recognition site. Alternatively, a modified or engineered nuclease agent can be employed. An "engineered nuclease agent" includes a nuclease that is engineered (modified or derived) from its native form to specifically recognize and induce a nick or double-strand break in the desired recognition site. Thus, an engineered nuclease agent can be derived from a native, naturally-occurring nuclease agent or it can be artificially created or synthesized. The modification of the nuclease agent can be as little as one amino acid in a protein cleavage agent or one nucleotide in a nucleic acid cleavage agent. In some embodiments, the engineered nuclease induces a nick or double-strand break in a recognition site, wherein the recognition site was not a sequence that would have been recognized by a native (non-engineered or non-modified) nuclease agent. Producing a nick or double-strand break in a recognition site or other DNA can be referred to herein as "cutting" or "cleaving" the recognition site or other DNA.

Active variants and fragments of the exemplified recognition sites are also provided. Such active variants can comprise at least 65%, 70%, 75%, 80%, 85%, 90%, 91%, 92%, 93%, 94%, 95%, 96%, 97%, 98%, 99% or more sequence identity to the given recognition site, wherein the active variants retain biological activity and hence are capable of being recognized and cleaved by a nuclease agent in a sequence-specific manner. Assays to measure the double-strand break of a recognition site by a nuclease agent are known in the art (e.g., TaqMan® qPCR assay, Frendewey D. et al., *Methods in Enzymology*, 2010, 476: 295-307, which is incorporated by reference herein in its entirety).

In specific embodiments, the recognition site is positioned within the polynucleotide encoding the selection marker. Such a position can be located within the coding region of the selection marker or within the regulatory regions, which influence the expression of the selection marker. Thus, a recognition site of the nuclease agent can be located in an intron of the selection marker, a promoter, an enhancer, a regulatory region, or any non-protein-coding region of the polynucleotide encoding the selection marker. In specific embodiments, a nick or double-strand break at the recognition site disrupts the activity of the selection marker. Methods to assay for the presence or absence of a functional selection marker are known.

In one embodiment, the nuclease agent is a Transcription Activator-Like Effector Nuclease (TALEN). TAL effector nucleases are a class of sequence-specific nucleases that can be used to make double-strand breaks at specific target sequences in the genome of a prokaryotic or eukaryotic organism. TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See, WO 2010/079430; Morbitzer et al. (2010) *PNAS* 10.1073/pnas.1013133107; Scholze & Boch (2010) *Virulence* 1:428-432; Christian et al. *Genetics* (2010) 186:757-761; Li et al. (2010) *Nuc. Acids Res*. (2010) doi:10.1093/nar/gkq704; and Miller et al. (2011) *Nature Biotechnology* 29:143-148; all of which are herein incorporated by reference.

Examples of suitable TAL nucleases, and methods for preparing suitable TAL nucleases, are disclosed, e.g., in US Patent Application No. 2011/0239315 A1, 2011/0269234 A1, 2011/0145940 A1, 2003/0232410 A1, 2005/0208489 A1, 2005/0026157 A1, 2005/0064474 A1, 2006/0188987 A1, and 2006/0063231 A1 (each hereby incorporated by reference). In various embodiments, TAL effector nucleases are engineered that cut in or near a target nucleic acid sequence in, e.g., a locus of interest or a genomic locus of interest, wherein the target nucleic acid sequence is at or near a sequence to be modified by a targeting vector. The TAL nucleases suitable for use with the various methods and compositions provided herein include those that are specifically designed to bind at or near target nucleic acid sequences to be modified by targeting vectors as described herein.

In one embodiment, each monomer of the TALEN comprises 33-35 TAL repeats that recognize a single base pair via two hypervariable residues. In one embodiment, the nuclease agent is a chimeric protein comprising a TAL repeat-based DNA binding domain operably linked to an independent nuclease. In one embodiment, the independent nuclease is a FokI endonuclease. In one embodiment, the nuclease agent comprises a first TAL-repeat-based DNA binding domain and a second TAL-repeat-based DNA binding domain, wherein each of the first and the second TAL-repeat-based DNA binding domain is operably linked to a FokI nuclease, wherein the first and the second TAL-repeat-based DNA binding domain recognize two contiguous target DNA sequences in each strand of the target DNA sequence separated by a spacer sequence of varying length (12-20 bp), and wherein the FokI nuclease subunits dimerize to create an active nuclease that makes a double strand break at a target sequence.

The nuclease agent employed in the various methods and compositions disclosed herein can further comprise a zinc-finger nuclease (ZFN). In one embodiment, each monomer of the ZFN comprises 3 or more zinc finger-based DNA binding domains, wherein each zinc finger-based DNA binding domain binds to a 3 bp subsite. In other embodiments, the ZFN is a chimeric protein comprising a zinc finger-based DNA binding domain operably linked to an independent nuclease. In one embodiment, the independent endonuclease is a FokI endonuclease. In one embodiment, the nuclease agent comprises a first ZFN and a second ZFN, wherein each of the first ZFN and the second ZFN is operably linked to a FokI nuclease subunit, wherein the first and the second ZFN recognize two contiguous target DNA sequences in each strand of the target DNA sequence separated by about 5-7 bp spacer, and wherein the FokI nuclease subunits dimerize to create an active nuclease to make a double strand break. See, for example, US20060246567; US20080182332; US20020081614; US20030021776; WO/2002/057308A2; US20130123484; US20100291048; WO/2011/017293A2; and Gaj et al. (2013) *Trends in Biotechnology*, 31(7):397-405 each of which is herein incorporated by reference.

In still another embodiment, the nuclease agent is a meganuclease. Meganucleases have been classified into four families based on conserved sequence motifs, the families are the LAGLIDADG, GIY-YIG, H—N—H, and His-Cys box families. These motifs participate in the coordination of metal ions and hydrolysis of phosphodiester bonds. Meganucleases are notable for their long recognition sites, and for tolerating some sequence polymorphisms in their DNA substrates. Meganuclease domains, structure and function are known, see for example, Guhan and Muniyappa (2003) *Crit Rev Biochem Mol Biol* 38:199-248; Lucas et al., (2001) *Nucleic Acids Res* 29:960-9; Jurica and Stoddard, (1999) *Cell Mol Life Sci* 55:1304-26; Stoddard, (2006) *Q Rev Biophys* 38:49-95; and Moure et al., (2002) *Nat Struct Biol* 9:764. In some examples a naturally occurring variant, and/or engineered derivative meganuclease is used. Methods for modifying the kinetics, cofactor interactions, expression, optimal conditions, and/or recognition site specificity, and screening for activity are known, see for example, Epinat et al., (2003) *Nucleic Acids Res* 31:2952-62; Chevalier et al., (2002) *Mol Cell* 10:895-905; Gimble et al., (2003) *Mol Biol*

334:993-1008; Seligman et al., (2002) *Nucleic Acids Res* 30:3870-9; Sussman et al., (2004) *J Mol Biol* 342:31-41; Rosen et al., (2006) *Nucleic Acids Res* 34:4791-800; Chames et al., (2005) *Nucleic Acids Res* 33:e178; Smith et al., (2006) *Nucleic Acids Res* 34:e149; Gruen et al., (2002) *Nucleic Acids Res* 30:e29; Chen and Zhao, (2005) *Nucleic Acids Res* 33:e154; WO2005105989; WO2003078619; WO2006097854; WO2006097853; WO2006097784; and WO2004031346.

Any meganuclease can be used herein, including, but not limited to, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, PI-PspI, F-SceI, F-SceII, F-SuvI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NcIIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or any active variants or fragments thereof.

In one embodiment, the meganuclease recognizes double-stranded DNA sequences of 12 to 40 base pairs. In one embodiment, the meganuclease recognizes one perfectly matched target sequence in the genome. In one embodiment, the meganuclease is a homing nuclease. In one embodiment, the homing nuclease is a LAGLIDADG family of homing nuclease. In one embodiment, the LAGLIDADG family of homing nuclease is selected from I-SceI, I-CreI, and I-Dmol.

Nuclease agents can further comprise restriction endonucleases, which include Type I, Type II, Type III, and Type IV endonucleases. Type I and Type III restriction endonucleases recognize specific recognition sites, but typically cleave at a variable position from the nuclease binding site, which can be hundreds of base pairs away from the cleavage site (recognition site). In Type II systems the restriction activity is independent of any methylase activity, and cleavage typically occurs at specific sites within or near to the binding site. Most Type II enzymes cut palindromic sequences, however Type IIa enzymes recognize non-palindromic recognition sites and cleave outside of the recognition site, Type IIb enzymes cut sequences twice with both sites outside of the recognition site, and Type IIs enzymes recognize an asymmetric recognition site and cleave on one side and at a defined distance of about 1-20 nucleotides from the recognition site. Type IV restriction enzymes target methylated DNA. Restriction enzymes are further described and classified, for example in the REBASE database (webpage at rebase.neb.com; Roberts et al., (2003) *Nucleic Acids Res* 31:418-20), Roberts et al., (2003) *Nucleic Acids Res* 31:1805-12, and Belfort et al., (2002) in *Mobile DNA II*, pp. 761-783, Eds. Craigie et al., (ASM Press, Washington, D.C.).

The nuclease agent employed in the various methods and compositions can also comprise a CRISPR/Cas system. Such systems can employ a Cas9 nuclease, which in some instances, is codon-optimized for the desired cell type in which it is to be expressed. The system further employs a fused crRNA-tracrRNA construct that functions with the codon-optimized Cas9. This single RNA is often referred to as a guide RNA or gRNA. Within a gRNA, the crRNA portion is identified as the 'target sequence' for the given recognition site and the tracrRNA is often referred to as the 'scaffold'. This system has been shown to function in a variety of eukaryotic and prokaryotic cells. Briefly, a short DNA fragment containing the target sequence is inserted into a guide RNA expression plasmid. The gRNA expression plasmid comprises the target sequence (in some embodiments around 20 nucleotides), a form of the tracrRNA sequence (the scaffold) as well as a suitable promoter that is active in the cell and necessary elements for proper processing in eukaryotic cells, Many of the systems rely on custom, complementary oligos that are annealed to form a double stranded DNA and then cloned into the gRNA expression plasmid. The gRNA expression cassette and the Cas9 expression cassette are then introduced into the cell. See, for example, Mali P et al. (2013) *Science* 2013 Feb. 15; 339 (6121):823-6; Jinek M et al. *Science* 2012 Aug. 17; 337 (6096):816-21; Hwang W Y et al. *Nat Biotechnol* 2013 March; 31(3):227-9; Jiang W et al. *Nat Biotechnol* 2013 March; 31(3):233-9; and, Cong L et al. *Science* 2013 Feb. 15; 339(6121):819-23, each of which is herein incorporated by reference.

The methods and compositions disclosed herein can utilize Clustered Regularly Interspersed Short Palindromic Repeats (CRISPR)/CRISPR-associated (Cas) systems or components of such systems to modify a genome within a cell. CRISPR/Cas systems include transcripts and other elements involved in the expression of or directing the activity of Cas genes. A CRISPR/Cas system can be a type I, a type II, or a type III system. The methods and compositions disclosed herein employ CRISPR/Cas systems by utilizing CRISPR complexes (comprising a guide RNA (gRNA) complexed with a Cas protein) for site-directed cleavage of nucleic acids.

Some CRISPR/Cas systems used in the methods disclosed herein are non-naturally occurring. A "non-naturally occurring" system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, some CRISPR/Cas systems employ non-naturally occurring CRISPR complexes comprising a gRNA and a Cas protein that do not naturally occur together.

(i) A. Cas RNA-Guided Endonucleases

Cas proteins generally comprise at least one RNA recognition or binding domain. Such domains can interact with guide RNAs (gRNAs, described in more detail below). Cas proteins can also comprise nuclease domains (e.g., DNase or RNase domains), DNA binding domains, helicase domains, protein-protein interaction domains, dimerization domains, and other domains. A nuclease domain possesses catalytic activity for nucleic acid cleavage. Cleavage includes the breakage of the covalent bonds of a nucleic acid molecule. Cleavage can produce blunt ends or staggered ends, and it can be single-stranded or double-stranded.

Examples of Cas proteins include Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

Cas proteins can be from a type II CRISPR/Cas system. For example, the Cas protein can be a Cas9 protein or be derived from a Cas9 protein. Cas9 proteins typically share four key motifs with a conserved architecture. Motifs 1, 2, and 4 are RuvC-like motifs, and motif 3 is an HNH motif. The Cas9 protein can be from, for example, *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, AlicyclobacHlus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus,* or *Acaryochloris marina.* Additional examples of the Cas9 family members are described in WO 2014/131833, herein incorporated by reference in its entirety. Cas9 protein from *S. pyogenes* or derived therefrom is a preferred enzyme. Cas9 protein from *S. pyogenes* is assigned SwissProt accession number Q99ZW2.

Cas proteins can be wild type proteins (i.e., those that occur in nature), modified Cas proteins (i.e., Cas protein variants), or fragments of wild type or modified Cas proteins. Cas proteins can also be active variants or fragments of wild type or modified Cas proteins. Active variants or fragments can comprise at least 80%, 85%, 90%, 91%, 92%, 93%, 94%, 95%, 96%, 97%, 98%, 99% or more sequence identity to the wild type or modified Cas protein or a portion thereof, wherein the active variants retain the ability to cut at a desired cleavage site and hence retain nick-inducing or double-strand-break-inducing activity. Assays for nick-inducing or double-strand-break-inducing activity are known and generally measure the overall activity and specificity of the Cas protein on DNA substrates containing the cleavage site.

Cas proteins can be modified to increase or decrease nucleic acid binding affinity, nucleic acid binding specificity, and/or enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity of the Cas protein.

Some Cas proteins comprise at least two nuclease domains, such as DNase domains. For example, a Cas9 protein can comprise a RuvC-like nuclease domain and an HNH-like nuclease domain. The RuvC and HNH domains can each cut a different strand of double-stranded DNA to make a double-stranded break in the DNA. See, e.g., Jinek et al. (2012) *Science* 337:816-821, hereby incorporated by reference in its entirety.

One or both of the nuclease domains can be deleted or mutated so that they are no longer functional or have reduced nuclease activity. If one of the nuclease domains is deleted or mutated, the resulting Cas protein (e.g., Cas9) can be referred to as a nickase and can generate a single-strand break at a CRISPR RNA recognition sequence within a double-stranded DNA but not a double-strand break (i.e., it can cleave the complementary strand or the non-complementary strand, but not both). If both of the nuclease domains are deleted or mutated, the resulting Cas protein (e.g., Cas9) will have a reduced ability to cleave both strands of a double-stranded DNA. An example of a mutation that converts Cas9 into a nickase is a D10A (aspartate to alanine at position 10 of Cas9) mutation in the RuvC domain of Cas9 from *S. pyogenes*. Likewise, H939A (histidine to alanine at amino acid position 839) or H840A (histidine to alanine at amino acid position 840) in the HNH domain of Cas9 from *S. pyogenes* can convert the Cas9 into a nickase. Other examples of mutations that convert Cas9 into a nickase include the corresponding mutations to Cas9 from *S. thermophilus*. See, e.g., Sapranauskas et al. (2011) *Nucleic Acids Research* 39:9275-9282 and WO 2013/141680, each of which is herein incorporated by reference in its entirety. Such mutations can be generated using methods such as site-directed mutagenesis, PCR-mediated mutagenesis, or total gene synthesis. Examples of other mutations creating nickases can be found, for example, in WO/2013/176772A1 and WO/2013/142578A1, each of which is herein incorporated by reference.

Cas proteins can also be fusion proteins. For example, a Cas protein can be fused to a cleavage domain, an epigenetic modification domain, a transcriptional activation domain, or a transcriptional repressor domain. See WO 2014/089290, incorporated herein by reference in its entirety. Cas proteins can also be fused to a heterologous polypeptide providing increased or decreased stability. The fused domain or heterologous polypeptide can be located at the N-terminus, the C-terminus, or internally within the Cas protein.

A Cas protein can be fused to a heterologous polypeptide that provides for subcellular localization. Such heterologous peptides include, for example, a nuclear localization signal (NLS) such as the SV40 NLS for targeting to the nucleus, a mitochondrial localization signal for targeting to the mitochondria, an ER retention signal, and the like. See, e.g., Lange et al. (2007) *J. Biol. Chem.* 282:5101-5105. Such subcellular localization signals can be located at the N-terminus, the C-terminus, or anywhere within the Cas protein. An NLS can comprise a stretch of basic amino acids, and can be a monopartite sequence or a bipartite sequence.

Cas proteins can also be linked to a cell-penetrating domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. See, for example, WO 2014/089290, herein incorporated by reference in its entirety. The cell-penetrating domain can be located at the N-terminus, the C-terminus, or anywhere within the Cas protein.

Cas proteins can also comprise a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreen1), yellow fluorescent proteins (e.g., YFP, eYFP, Citrine, Venus, YPet, PhiYFP, ZsYellow1), blue fluorescent proteins (e.g. eBFP, eBFP2, Azurite, mKalaml, GFPuv, Sapphire, T-sapphire), cyan fluorescent proteins (e.g. eCFP, Cerulean, CyPet, AmCyanl, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, Jred), orange fluorescent proteins (mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, hemagglutinin (HA), nus, Softag 1, Softag 3, Strep, SBP, Glu-Glu, HSV, KT3, S, S1, T7, V5, VSV-G, histidine (His), biotin carboxyl carrier protein (BCCP), and calmodulin.

Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism.

Nucleic acids encoding Cas proteins can be stably integrated in the genome of the cell and operably linked to a promoter active in the cell. Alternatively, nucleic acids encoding Cas proteins can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. Promoters that can be used in an expression construct include, for example, promoters active in a pluripotent rat, eukaryotic, mammalian, non-human mammalian, human, rodent, mouse, or hamster cell. Examples of other promoters are described elsewhere herein.

(ii) B. Guide RNAs (gRNAs)

A "guide RNA" or "gRNA" includes an RNA molecule that binds to a Cas protein and targets the Cas protein to a specific location within a target DNA. Guide RNAs can comprise two segments: a "DNA-targeting segment" and a "protein-binding segment." "Segment" includes a segment, section, or region of a molecule, such as a contiguous stretch of nucleotides in an RNA. Some gRNAs comprise two separate RNA molecules: an "activator-RNA" and a "targeter-RNA." Other gRNAs are a single RNA molecule (single RNA polynucleotide), which can also be called a "single-molecule gRNA," a "single-guide RNA," or an "sgRNA." See, e.g., WO/2013/176772A1, WO/2014/065596A1, WO/2014/089290A1, WO/2014/093622A2, WO/2014/099750A2, WO/2013142578A1, and WO 2014/131833A1, each of which is herein incorporated by reference. The terms "guide RNA" and "gRNA" include both double-molecule gRNAs and single-molecule gRNAs.

An exemplary two-molecule gRNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA" or "scaffold") molecule. A crRNA comprises both the DNA-targeting segment (single-stranded) of the gRNA and a stretch of nucleotides that forms one half of the dsRNA duplex of the protein-binding segment of the gRNA.

A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA.

The crRNA and the corresponding tracrRNA hybridize to form a gRNA. The crRNA additionally provides the single-stranded DNA-targeting segment that hybridizes to a CRISPR RNA recognition sequence. If used for modification within a cell, the exact sequence of a given crRNA or tracrRNA molecule can be designed to be specific to the species in which the RNA molecules will be used. See, for example, Mali et al. (2013) Science 339:823-826; Jinek et al. (2012) Science 337:816-821; Hwang et al. (2013) Nat. Biotechnol. 31:227-229; Jiang et al. (2013) Nat. Biotechnol. 31:233-239; and Cong et al. (2013) Science 339:819-823, each of which is herein incorporated by reference.

The DNA-targeting segment (crRNA) of a given gRNA comprises a nucleotide sequence that is complementary to a sequence in a target DNA. The DNA-targeting segment of a gRNA interacts with a target DNA in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the Cas9 system and organism but often contain a targeting segment of between 21 to 72 nucleotides length, flanked by two direct repeats (DR) of a length of between 21 to 46 nucleotides (see, e.g., WO2014/131833). In the case of S. pyogenes, the DRs are 36 nucleotides long and the targeting segment is 30 nucleotides long. The 3' located DR is complementary to and hybridizes with the corresponding tracrRNA, which in turn binds to the Cas9 protein.

The DNA-targeting segment can have a length of from about 12 nucleotides to about 100 nucleotides. For example, the DNA-targeting segment can have a length of from about 12 nucleotides (nt) to about 80 nt, from about 12 nt to about 50 nt, from about 12 nt to about 40 nt, from about 12 nt to about 30 nt, from about 12 nt to about 25 nt, from about 12 nt to about 20 nt, or from about 12 nt to about 19 nt. Alternatively, the DNA-targeting segment can have a length of from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 19 nt to about 70 nt, from about 19 nt to about 80 nt, from about 19 nt to about 90 nt, from about 19 nt to about 100 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, from about 20 nt to about 60 nt, from about 20 nt to about 70 nt, from about 20 nt to about 80 nt, from about 20 nt to about 90 nt, or from about 20 nt to about 100 nt.

The nucleotide sequence of the DNA-targeting segment that is complementary to a nucleotide sequence (CRISPR RNA recognition sequence) of the target DNA can have a length at least about 12 nt. For example, the DNA-targeting sequence (i.e., the sequence within the DNA-targeting segment that is complementary to a CRISPR RNA recognition sequence within the target DNA) can have a length at least about 12 nt, at least about 15 nt, at least about 18 nt, at least about 19 nt, at least about 20 nt, at least about 25 nt, at least about 30 nt, at least about 35 nt, or at least about 40 nt. Alternatively, the DNA-targeting sequence can have a length of from about 12 nucleotides (nt) to about 80 nt, from about 12 nt to about 50 nt, from about 12 nt to about 45 nt, from about 12 nt to about 40 nt, from about 12 nt to about 35 nt, from about 12 nt to about 30 nt, from about 12 nt to about 25 nt, from about 12 nt to about 20 nt, from about 12 nt to about 19 nt, from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. In some cases, the DNA-targeting sequence can have a length of at about 20 nt.

TracrRNAs can be in any form (e.g., full-length tracrRNAs or active partial tracrRNAs) and of varying lengths. They can include primary transcripts or processed forms. For example, tracrRNAs (as part of a single-guide RNA or as a separate molecule as part of a two-molecule gRNA) may comprise or consist of all or a portion of a wild-type tracrRNA sequence (e.g., about or more than about 20, 26, 32, 45, 48, 54, 63, 67, 85, or more nucleotides of a wild-type tracrRNA sequence). Examples of wild-type tracrRNA sequences from *S. pyogenes* include 171-nucleotide, 89-nucleotide, 75-nucleotide, and 65-nucleotide versions. See, for example, Deltcheva et al. (2011) *Nature* 471:602-607; WO 2014/093661, each of which is incorporated herein by reference in their entirety. Examples of tracrRNAs within single-guide RNAs (sgRNAs) include the tracrRNA segments found within +48, +54, +67, and +85 versions of sgRNAs, where "+n" indicates that up to the +n nucleotide of wild-type tracrRNA is included in the sgRNA. See U.S. Pat. No. 8,697,359, incorporated herein by reference in its entirety.

The percent complementarity between the DNA-targeting sequence and the CRISPR RNA recognition sequence within the target DNA can be at least 60% (e.g., at least 65%, at least 70%, at least 75%, at least 80%, at least 85%, at least 90%, at least 95%, at least 97%, at least 98%, at least 99%, or 100%). The percent complementarity between the DNA-targeting sequence and the CRISPR RNA recognition sequence within the target DNA can be at least 60% over about 20 contiguous nucleotides. As an example, the percent complementarity between the DNA-targeting sequence and the CRISPR RNA recognition sequence within the target DNA is 100% over the 14 contiguous nucleotides at the 5' end of the CRISPR RNA recognition sequence within the complementary strand of the target DNA and as low as 0% over the remainder. In such a case, the DNA-targeting sequence can be considered to be 14 nucleotides in length. As another example, the percent complementarity between the DNA-targeting sequence and the CRISPR RNA recognition sequence within the target DNA is 100% over the seven contiguous nucleotides at the 5' end of the CRISPR RNA recognition sequence within the complementary strand of the target DNA and as low as 0% over the remainder. In such a case, the DNA-targeting sequence can be considered to be 7 nucleotides in length.

The protein-binding segment of a gRNA can comprise two stretches of nucleotides that are complementary to one another. The complementary nucleotides of the protein-binding segment hybridize to form a double-stranded RNA duplex (dsRNA). The protein-binding segment of a subject gRNA interacts with a Cas protein, and the gRNA directs the bound Cas protein to a specific nucleotide sequence within target DNA via the DNA-targeting segment.

Guide RNAs can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin)); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like); and combinations thereof.

Guide RNAs can be provided in any form. For example, the gRNA can be provided in the form of RNA, either as two molecules (separate crRNA and tracrRNA) or as one molecule (sgRNA), and optionally in the form of a complex with a Cas protein. The gRNA can also be provided in the form of DNA encoding the RNA. The DNA encoding the gRNA can encode a single RNA molecule (sgRNA) or separate RNA molecules (e.g., separate crRNA and tracrRNA). In the latter case, the DNA encoding the gRNA can be provided as separate DNA molecules encoding the crRNA and tracrRNA, respectively.

DNAs encoding gRNAs can be stably integrated in the genome of the cell and operably linked to a promoter active in the cell. Alternatively, DNAs encoding gRNAs can be operably linked to a promoter in an expression construct. Such promoters can be active, for example, in a pluripotent rat, eukaryotic, mammalian, non-human mammalian, human, rodent, mouse, or hamster cell. In some instances, the promoter is an RNA polymerase III promoter, such as a human U6 promoter, a rat U6 polymerase III promoter, or a mouse U6 polymerase III promoter. Examples of other promoters are described elsewhere herein.

Alternatively, gRNAs can be prepared by various other methods. For example, gRNAs can be prepared by in vitro transcription using, for example, T7 RNA polymerase (see, for example, WO 2014/089290 and WO 2014/065596). Guide RNAs can also be a synthetically produced molecule prepared by chemical synthesis.

(iii) C. CRISPR RNA Recognition Sequences

The term "CRISPR RNA recognition sequence" includes nucleic acid sequences present in a target DNA to which a DNA-targeting segment of a gRNA will bind, provided sufficient conditions for binding exist. For example, CRISPR RNA recognition sequences include sequences to which a guide RNA is designed to have complementarity, where hybridization between a CRISPR RNA recognition sequence and a DNA targeting sequence promotes the formation of a CRISPR complex. Full complementarity is not necessarily required, provided there is sufficient complementarity to cause hybridization and promote formation of a CRISPR complex. CRISPR RNA recognition sequences also include cleavage sites for Cas proteins, described in more detail below. A CRISPR RNA recognition sequence can comprise any polynucleotide, which can be located, for example, in the nucleus or cytoplasm of a cell or within an organelle of a cell, such as a mitochondrion or chloroplast.

The CRISPR RNA recognition sequence within a target DNA can be targeted by (i.e., be bound by, or hybridize with, or be complementary to) a Cas protein or a gRNA. Suitable DNA/RNA binding conditions include physiological conditions normally present in a cell. Other suitable DNA/RNA binding conditions (e.g., conditions in a cell-free system) are known in the art (see, e.g., Molecular Cloning: A Laboratory Manual, 3rd Ed. (Sambrook et al., Harbor Laboratory Press 2001)). The strand of the target DNA that is complementary to and hybridizes with the Cas protein or gRNA can be called the "complementary strand," and the strand of the target DNA that is complementary to the "complementary strand" (and is therefore not complementary to the Cas protein or gRNA) can be called "noncomplementary strand" or "template strand."

The Cas protein can cleave the nucleic acid at a site within or outside of the nucleic acid sequence present in the target DNA to which the DNA-targeting segment of a gRNA will bind. The "cleavage site" includes the position of a nucleic acid at which a Cas protein produces a single-strand break or a double-strand break. For example, formation of a CRISPR complex (comprising a gRNA hybridized to a CRISPR RNA recognition sequence and complexed with a Cas protein) can result in cleavage of one or both strands in or near (e.g., within 1, 2, 3, 4, 5, 6, 7, 8, 9, 10, 20, 50, or more base pairs from) the nucleic acid sequence present in a target DNA to which a DNA-targeting segment of a gRNA will bind. If the cleavage site is outside of the nucleic acid sequence to which the DNA-targeting segment of the gRNA will bind, the cleavage site is still considered to be within the "CRISPR RNA recognition sequence." The cleavage site can be on only one strand or on both strands of a nucleic acid. Cleavage sites can be at the same position on both strands of the nucleic acid (producing blunt ends) or can be at different sites on each strand (producing staggered ends). Staggered ends can be produced, for example, by using two Cas proteins, each of which produces a single-strand break at a different cleavage site on each strand, thereby producing a double-strand break. For example, a first nickase can create a single-strand break on the first strand of double-stranded DNA (dsDNA), and a second nickase can create a single-strand break on the second strand of dsDNA such that overhanging sequences are created. In some cases, the CRISPR RNA recognition sequence of the nickase on the first strand is separated from the CRISPR RNA recognition sequence of the nickase on the second strand by at least 2, 3, 4, 5, 6, 7, 8, 9, 10, 15, 20, 25, 30, 40, 50, 75, 100, 250, 500, or 1,000 base pairs.

Site-specific cleavage of target DNA by Cas9 can occur at locations determined by both (i) base-pairing complementarity between the gRNA and the target DNA and (ii) a short motif, called the protospacer adjacent motif (PAM), in the target DNA. The PAM can flank the CRISPR RNA recognition sequence. Optionally, the CRISPR RNA recognition sequence can be flanked by the PAM. For example, the cleavage site of Cas9 can be about 1 to about 10 or about 2 to about 5 base pairs (e.g., 3 base pairs) upstream or downstream of the PAM sequence. In some cases (e.g., when Cas9 from *S. pyogenes* or a closely related Cas9 is used), the PAM sequence of the non-complementary strand can be 5'-$N_1$GG-3', where $N_1$ is any DNA nucleotide and is immediately 3' of the CRISPR RNA recognition sequence of the non-complementary strand of the target DNA. As such, the PAM sequence of the complementary strand would be 5'-CC $N_2$-3', where $N_2$ is any DNA nucleotide and is immediately 5' of the CRISPR RNA recognition sequence of the complementary strand of the target DNA. In some such cases, $N_1$ and $N_2$ can be complementary and the $N_1$-$N_2$ base pair can be any base pair (e.g., $N_1$=C and $N_2$=G; $N_1$=G and $N_2$=C; $N_1$=A and $N_2$=T, $N_1$=T, and $N_2$=A).

Examples of CRISPR RNA recognition sequences include a DNA sequence complementary to the DNA-targeting segment of a gRNA, or such a DNA sequence in addition to a PAM sequence. For example, the target motif can be a 20-nucleotide DNA sequence immediately preceding an NGG motif recognized by a Cas protein (see, for example, WO 2014/165825). The guanine at the 5' end can facilitate transcription by RNA polymerase in cells. Other examples of CRISPR RNA recognition sequences can include two guanine nucleotides at the 5' end (e.g., GGN$_{20}$NGG; SEQ ID NO: 9) to facilitate efficient transcription by T7 polymerase in vitro. See, for example, WO 2014/065596.

The CRISPR RNA recognition sequence can be any nucleic acid sequence endogenous or exogenous to a cell. The CRISPR RNA recognition sequence can be a sequence coding a gene product (e.g., a protein) or a non-coding sequence (e.g., a regulatory sequence) or can include both.

In one embodiment, the target sequence is immediately flanked by a Protospacer Adjacent Motif (PAM) sequence. In one embodiment, the locus of interest comprises the nucleotide sequence of SEQ ID NO: 1. In one embodiment, the gRNA comprises a third nucleic acid sequence encoding a Clustered Regularly Interspaced Short Palindromic Repeats (CRISPR) RNA (crRNA) and a trans-activating CRISPR RNA (tracrRNA). In another embodiment, the genome of the pluripotent rat cell comprises a target DNA region complementary to the target sequence. In some such methods, the Cas protein is Cas9. In some embodiments, the gRNA comprises (a) the chimeric RNA of the nucleic acid sequence of SEQ ID NO: 2; or (b) the chimeric RNA of the nucleic acid sequence of SEQ ID NO: 3. In some such methods, the crRNA comprises the sequence set forth in SEQ ID NO: 4, SEQ ID NO: 5, or SEQ ID NO: 6. In some such methods, the tracrRNA comprises the sequence set forth in SEQ ID NO: 7 or SEQ ID NO: 8.

Active variants and fragments of nuclease agents (i.e. an engineered nuclease agent) are also provided. Such active variants can comprise at least 65%, 70%, 75%, 80%, 85%, 90%, 91%, 92%, 93%, 94%, 95%, 96%, 97%, 98%, 99% or more sequence identity to the native nuclease agent, wherein the active variants retain the ability to cut at a desired recognition site and hence retain nick or double-strand-break-inducing activity. For example, any of the nuclease agents described herein can be modified from a native endonuclease sequence and designed to recognize and induce a nick or double-strand break at a recognition site that was not recognized by the native nuclease agent. Thus, in some embodiments, the engineered nuclease has a specificity to induce a nick or double-strand break at a recognition site that is different from the corresponding native nuclease agent recognition site. Assays for nick or double-strand-break-inducing activity are known and generally measure the overall activity and specificity of the endonuclease on DNA substrates containing the recognition site.

The nuclease agent may be introduced into the cell by any means known in the art. The polypeptide encoding the nuclease agent may be directly introduced into the cell. Alternatively, a polynucleotide encoding the nuclease agent can be introduced into the cell. When a polynucleotide encoding the nuclease agent is introduced into the cell, the nuclease agent can be transiently, conditionally or constitutive expressed within the cell. Thus, the polynucleotide encoding the nuclease agent can be contained in an expression cassette and be operably linked to a conditional promoter, an inducible promoter, a constitutive promoter, or a tissue-specific promoter. Such promoters of interest are discussed in further detail elsewhere herein. Alternatively, the nuclease agent is introduced into the cell as an mRNA encoding a nuclease agent.

In specific embodiments, the polynucleotide encoding the nuclease agent is stably integrated in the genome of the cell and operably linked to a promoter active in the cell. In other embodiments, the polynucleotide encoding the nuclease agent is in the same targeting vector comprising the insert polynucleotide, while in other instances the polynucleotide encoding the nuclease agent is in a vector or a plasmid that is separate from the targeting vector comprising the insert polynucleotide.

When the nuclease agent is provided to the cell through the introduction of a polynucleotide encoding the nuclease agent, such a polynucleotide encoding a nuclease agent can be modified to substitute codons having a higher frequency of usage in the cell of interest, as compared to the naturally occurring polynucleotide sequence encoding the nuclease agent. For example the polynucleotide encoding the nuclease agent can be modified to substitute codons having a higher frequency of usage in a given prokaryotic or eukaryotic cell of interest, including a bacterial cell, a yeast cell, a human cell, a non-human cell, a mammalian cell, a rodent cell, a mouse cell, a rat cell or any other host cell of interest, as compared to the naturally occurring polynucleotide sequence.

B. Employing the CRISPR/Cas System in Combination with a Large Targeting Vector (LTVEC) or a Small Targeting Vector (SmallTVEC) to Modify a Challenging Genomic Loci or a Y Chromosome Locus Non-limiting methods for modifying a challenging genomic locus or a locus of the Y chromosome comprise exposing the chromosome (i.e., the Y chromosome) to a Cas protein and a CRISPR RNA in the presence of a large targeting vector (LTVEC) comprising a nucleic acid sequence of at least 10 kb, wherein following exposure to the Cas protein, the CRISPR RNA, and the LTVEC, the chromosome (i.e., the Y chromosome) is modified to contain at least 10 kb nucleic acid sequence.

The method can employ any of the LTVECs or smallTVECs described herein. In non-limiting embodiments, the LTVEC or smallTVEC comprises a nucleic acid sequence of at least 20 kb, at least 30 kb, at least 40 kb, at least 50 kb, at least 60 kb, at least 70 kb, at least 80 kb, at least 90 kb, at least 100 kb, at least 150 kb, or at least 200 kb. In other embodiments, the sum total of 5' and 3' homology arms of the LTVEC is from about 10 kb to about 150 kb, about 10 kb to about 20 kb, from about 20 kb to about 40 kb, from about 40 kb to about 60 kb, from about 60 kb to about 80 kb, from about 80 kb to about 100 kb, from about 100 kb to about 120 kb, or from about 120 kb to 150 kb. In another embodiment, the sum total of 5' and 3' homology arms of the smallTVEC is about 0.5 kb, 1 kb, 1.5 kb, 2 kb, 3 kb, 4 kb, 5 kb, 6 kb, 7 kb, 8 kb, 9 kb, about 0.5 kb to about 1 kb, about 1 kb to about 1.5 kb, about 1.5 kb to about 2 kb, about 2 kb to about 3 kb, about 3 kb to about 4 kb, about 4 kb to about 5 kb, about 5 kb to about 6 kb, about 6 kb to about 7 kb, about 8 kb to about 9 kb, or is at least 10 kb.

Further provided is a method for modifying a challenging target locus or a target genomic locus on the Y chromosome, comprising: (a) providing a mammalian cell comprising the challenging target locus or a target genomic locus on the Y chromosome, wherein the target genomic locus comprises a guide RNA (gRNA) target sequence; (b) introducing into the mammalian cell: (i) a large targeting vector (LTVEC) comprising a first nucleic acid flanked with targeting arms homologous to the target genomic locus, wherein the LTVEC is at least 10 kb; (ii) a first expression construct comprising a first promoter operably linked to a second nucleic acid encoding a Cas protein, and (iii) a second expression construct comprising a second promoter operably linked to a third nucleic acid encoding a guide RNA (gRNA) comprising a nucleotide sequence that hybridizes to the gRNA target sequence and a trans-activating CRISPR RNA (tracrRNA), wherein the first and the second promoters are active in the mammalian cell; and, (c) identifying a modified mammalian cell comprising a targeted genetic modification at the challenging target genomic locus or at the target genomic locus on the Y chromosome. In specific embodiments, the first and the second expression constructs are on a single nucleic acid molecule. In other embodiments, the target genomic locus of the Y chromosomes is the Sry locus.

As outlined above, in one embodiment, the Cas protein can comprise a Cas9 protein. In another embodiment, the gRNA target sequence is immediately flanked by a Protospacer Adjacent Motif (PAM) sequence.

The method can employ any of the LTVECs or smallTVECs described herein. In non-limiting embodiments, the LTVEC or smallTVEC is at least 0.5 kb, at least 1 kb, at least 5 kb, at least 10 kb, at least 15 kb, at least 20 kb, at least 30 kb, at least 40 kb, at least 50 kb, at least 60 kb, at least 70 kb, at least 80 kb, at least 90 kb, at least 100 kb, at least 150 kb, or at least 200 kb. In other embodiments, the sum total of 5' and 3' homology arms of the LTVEC is from about 10 kb to about 150 kb, about 10 kb to about 20 kb, from about 20 kb to about 40 kb, from about 40 kb to about 60 kb, from about 60 kb to about 80 kb, from about 80 kb to about 100 kb, from about 100 kb to about 120 kb, or from about 120 kb to 150 kb.

The various methods employing the CRISPR/Cas system (or any method disclosed herein) can be performed on, for example, mammalian cells, non-human mammalian cells, fibroblast cells, rodent cells, rat cells, mouse cells, or hamster cells. The cell can be a pluripotent cell, an induced pluripotent stem (iPS) cell, a mouse embryonic stem (ES) cell, a rat embryonic stem (ES) cell, a human embryonic stem (ES) cell or a developmentally restricted human progenitor cell.

As discussed in detail below, following the modification a challenging genomic locus or a genomic locus of interest on the Y chromosome (i.e., the Sry locus) of a non-human pluripotent cell employing, for example, using the CRISPR/CAS system outline above, the genetically modified non-human pluripotent cell that is produced can be introduced into a non-human host embryo; and the non-human host embryo comprising the modified pluripotent cell in a surrogate mother is gestated. The surrogate mother produces F0 progeny comprising the targeted genetic modification. In specific embodiments, the targeted genetic modification is capable of being transmitted through the germline.

C. Selection Markers

Various selection markers can be used in the methods and compositions disclosed herein which provide for modifying a target genomic locus on the Y chromosome or a challenging target genomic locus. Such markers are disclosed elsewhere herein and include, but are not limited to, selection markers that impart resistance to an antibiotic such as G418, hygromycin, blastocidin, neomycin, or puromycin. The polynucleotide encoding the selection markers are operably linked to a promoter active in the cell. Such expression cassettes and their various regulatory components are discussed in further detailed elsewhere herein.

D. Target Genomic Locus

Various methods and compositions are provided which allow for the integration of at least one insert polynucleotide at a target genomic locus on the Y chromosome or a challenging target genomic locus. As used herein, a "target genomic locus on the Y chromosome" comprises any segment or region of DNA on the Y chromosome that one desires to integrate an insert polynucleotide.

The genomic locus on the Y chromosome or a challenging target genomic locus being targeted can be native to the cell, or alternatively can comprise a heterologous or exogenous segment of DNA that was integrated into the chromosome of the cell. Such heterologous or exogenous segments of DNA can include transgenes, expression cassettes, polynucleotide encoding selection makers, or heterologous or exogenous regions of genomic DNA. The target genomic locus on the Y chromosome or the challenging target genomic locus can comprise any of the targeted genomic integration system including, for example, the recognition site, the selection marker, previously integrated insert polynucleotides, polynucleotides encoding nuclease agents, promoters, etc. Alternatively, the target genomic locus on the Y chromosome or the challenging target genomic locus can be located within a yeast artificial chromosome (YAC), bacterial artificial chromosome (BAC), a human artificial chromosome, or any other engineered genomic region contained in an appropriate host cell. Thus, in specific embodiments, the targeted genomic locus on the Y chromosome or the challenging target genomic locus can comprise native, heterologous or exogenous genomic nucleic acid sequence from a non-human mammal, a non-human cell, a rodent, a human, a rat, a mouse, a hamster, a rabbit, a pig, a bovine, a deer, a sheep, a goat, a chicken, a cat, a dog, a ferret, a primate (e.g., marmoset, rhesus monkey), domesticated mammal or an agricultural mammal or any other organism of interest or a combination thereof.

Non-limiting examples of the target genomic locus on the Y chromosome include, the Sry gene, the Uty gene, the Eif2s3y gene, the Ddx3y gene, the gene, the Ube1y gene, the Tspy gene, the Usp9y gene, the Zfy1 gene, and the Zfy2 gene and the region on the Y chromosome encompassing the Kdm5d, Eif2s3y, Tspy, Uty, Ddx3y, and Usp9y genes. Such a locus on the Y chromosome can be from a non-human mammal, a mammal, a rodent, a human, a rat, a mouse, a hamster, a rabbit, a pig, a bovine, a deer, a sheep, a goat, a chicken, a cat, a dog, a ferret, a primate (e.g., marmoset, rhesus monkey), domesticated mammal or an agricultural mammal or any other organism of interest or a combination thereof. Such cells include pluripotent cells, including, for example, induced pluripotent stem (iPS) cells, mouse embryonic stem (ES) cells, rat embryonic stem (ES) cells, human embryonic stem (ES) cell, or developmentally restricted human progenitor cells.

As described elsewhere herein, various methods and compositions are provided which comprise XY pluripotent and/or totipotent cells (such as XY ES cells or iPS cells) having a decreased activity or level of the Sry protein. The various methods described herein to modify genomic locus on the Y chromosome can also be used to introduce targeted genetic modifications to polynucleotides of interest that are not located on the Y chromosome.

E. Targeting Vectors and Insert Polynucleotides

As outlined above, methods and compositions provided herein employ targeting vectors alone or in combination with a nuclease agent. "Homologous recombination" is used conventionally to refer to the exchange of DNA fragments between two DNA molecules at cross-over sites within the regions of homology.

i. Insert Polynucleotide

As used herein, the "insert polynucleotide" comprises a segment of DNA that one desires to integrate at the target genomic locus. In specific embodiments, the target genomic locus is on the Y chromosome. In other embodiments, the target genomic locus is a challenging genomic locus. In one embodiment, the insert polynucleotide comprises one or more polynucleotides of interest. In other embodiments, the insert polynucleotide can comprise one or more expression cassettes. A given expression cassette can comprise a polynucleotide of interest, a polynucleotide encoding a selection marker and/or a reporter gene along with the various regulatory components that influence expression. Non-limiting examples of polynucleotides of interest, selection markers, and reporter genes that can be included within the insert polynucleotide are discussed in detail elsewhere herein.

In specific embodiments, the insert polynucleotide can comprise a genomic nucleic acid. In one embodiment, the genomic nucleic acid is derived from an animal, a mouse, a human, a non-human, a rodent, a non-human, a rat, a hamster, a rabbit, a pig, a bovine, a deer, a sheep, a goat, a chicken, a cat, a dog, a ferret, a primate (e.g., marmoset, rhesus monkey), domesticated mammal or an agricultural mammal, an avian, or any other organism of interest or a combination thereof.

In further embodiments, the insert polynucleotide comprises a conditional allele. In one embodiment, the conditional allele is a multifunctional allele, as described in US 2011/0104799, which is incorporated by reference in its entirety. In specific embodiments, the conditional allele comprises: (a) an actuating sequence in sense orientation with respect to transcription of a target gene, and a drug selection cassette in sense or antisense orientation; (b) in antisense orientation a nucleotide sequence of interest (NSI) and a conditional by inversion module (COIN, which utilizes an exon-splitting intron and an invertible genetrap-like module; see, for example, US 2011/0104799, which is incorporated by reference in its entirety); and (c) recombinable units that recombine upon exposure to a first recombinase to form a conditional allele that (i) lacks the actuating sequence and the DSC, and (ii) contains the NSI in sense orientation and the COIN in antisense orientation.

The insert polynucleotide can be from about 5 kb to about 200 kb, from about 5 kb to about 10 kb, from about 10 kb to about 20 kb, from about 20 kb to about 30 kb, from about 30 kb to about 40 kb, from about 40 kb to about 50 kb, from about 60 kb to about 70 kb, from about 80 kb to about 90 kb, from about 90 kb to about 100 kb, from about 100 kb to about 110 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, from about 190 kb to about 200 kb, from about 200 kb to about 250 kb, from about 250 kb to about 300 kb, from about 300 kb to about 350 kb, or from about 350 kb to about 400 kb.

In specific embodiments, the insert polynucleotide comprises a nucleic acid flanked with site-specific recombination target sequences. It is recognized that while the entire insert polynucleotide can be flanked by such site-specific recombination target sequence, any region or individual polynucleotide of interest within the insert polynucleotide can also be flanked by such sites. The term "recombination site" as used herein includes a nucleotide sequence that is recognized by a site-specific recombinase and that can serve as a substrate for a recombination event. The term "site-specific recombinase" as used herein includes a group of enzymes that can facilitate recombination between recombination sites where the two recombination sites are physically separated within a single nucleic acid molecule or on separate nucleic acid molecules. Examples of site-specific recombinases include, but are not limited to, Cre, Flp, and Dre recombinases. The site-specific recombinase can be introduced into the cell by any means, including by introducing the recombinase polypeptide into the cell or by introducing a polynucleotide encoding the site-specific recombinase into the host cell. The polynucleotide encoding the site-specific recombinase can be located within the insert polynucleotide or within a separate polynucleotide. The site-specific recombinase can be operably linked to a promoter active in the cell including, for example, an inducible promoter, a promoter that is endogenous to the cell, a promoter that is heterologous to the cell, a cell-specific promoter, a tissue-specific promoter, or a developmental stage-specific promoter. Site-specific recombination target sequences which can flank the insert polynucleotide or any polynucleotide of interest in the insert polynucleotide can include, but are not limited to, loxP, lox511, lox2272, lox66, lox71, loxM2, lox5171, FRT, FRT11, FRT71, attp, att, FRT, rox, and a combination thereof.

In other embodiments, the site-specific recombination sites flank a polynucleotide encoding a selection marker and/or a reporter gene contained within the insert polynucleotide. In such instances following integration of the insert polynucleotide at the targeted genomic locus the sequences between the site-specific recombination sites can be removed.

In one embodiment, the insert polynucleotide comprises a polynucleotide encoding a selection marker. Such selection markers include, but are not limited, to neomycin phosphotransferase (neo$^r$), hygromycin B phosphotransferase (hyg$^r$), puromycin-N-acetyltransferase (puro$^r$), blasticidin S deaminase (bsr$^r$), xanthine/guanine phosphoribosyl transferase (gpt), or herpes simplex virus thymidine kinase (HSV-k), or a combination thereof. In one embodiment, the polynucleotide encoding the selection marker is operably linked to a promoter active in the cell. When serially tiling polynucleotides of interest into a targeted genomic locus, the selection marker can comprise a recognition site for a nuclease agent, as outlined above. In one embodiment, the polynucleotide encoding the selection marker is flanked with a site-specific recombination target sequences.

The insert polynucleotide can further comprise a reporter gene operably linked to a promoter, wherein the reporter gene encodes a reporter protein selected from the group consisting of LacZ, mPlum, mCherry, tdTomato, mStrawberry, J-Red, DsRed, mOrange, mKO, mCitrine, Venus, YPet, enhanced yellow fluorescent protein (EYFP), Emerald, enhanced green fluorescent protein (EGFP), CyPet, cyan fluorescent protein (CFP), Cerulean, T-Sapphire, luciferase, alkaline phosphatase, and a combination thereof. Such reporter genes can be operably linked to a promoter active in the cell. Such promoters can be an inducible promoter, a promoter that is endogenous to the reporter gene or the cell, a promoter that is heterologous to the reporter gene or to the cell, a cell-specific promoter, a tissue-specific promoter manner or a developmental stage-specific promoter.

ii. Targeting Vectors

Targeting vectors are employed to introduce the insert polynucleotide into the targeted genomic locus on the Y chromosome or into a challenging target locus or on another chromosome of interest. The targeting vector comprises the insert polynucleotide and further comprises an upstream and a downstream homology arm that flank the insert polynucleotide. The homology arms that flank the insert polynucleotide correspond to genomic regions within the targeted genomic locus. For ease of reference, the corresponding genomic regions within the targeted genomic locus are referred to herein as "target sites". Thus, in one example, a targeting vector can comprise a first insert polynucleotide flanked by a first and a second homology arm corresponding to a first and a second target site located in sufficient proximity to the first recognition site within the polynucleotide encoding the selection marker. As such, the targeting vector thereby aids in the integration of the insert polynucleotide into the targeted genomic locus through a homologous recombination event that occurs between the homology arms and the corresponding target sites within the genome of the cell.

A homology arm of the targeting vector can be of any length that is sufficient to promote a homologous recombination event with a corresponding target site, including for example, from about 400 bp to about 500 bp, from about 500 bp to about 600 bp, from about 600 bp to about 700 bp, from about 700 bp to about 800 bp, from about 800 bp to about 900 bp, or from about 900 bp to about 1000 bp; or at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 100-200, or 200-300 kilobases in length or greater. In specific embodiments, the sum total of the targeting arms is at least 0.5 kb, 1 kb, 1.5 kb, 2 kb, 3 kb, 4 kb, 5 kb, 6 kb, 7 kb, 8 kb, 9 kb or at least 10 kb. In other embodiments, the sum total of the homology arms is between about 0.5 kb to about 1 kb, about 1 kb to about 1.5 kb, about 1.5 kb to about 2 kb, about 2 kb to about 3 kb, about 3 kb to about 4 kb, about 4 kb to about 5 kb, about 5 kb to about 6 kb, about 6 kb to about 7 kb, about 7 kb to about 8 kb, about 8 kb to about 9 kb, or about 10 kb to about 150 kb. As outlined in further detail below, large targeting vectors can employ targeting arms of greater length.

The target sites within the targeted genomic locus that correspond to the upstream and downstream homology arms of the targeting vector are located in "sufficient proximity to the recognition site" located in the polynucleotide encoding the selection marker. As used herein, the upstream and downstream homology arms of a targeting vector are "located in sufficient proximity" to a recognition site when the distance is such as to promote the occurrence of a homologous recombination event between the target sites and the homology arms upon a nick or double-strand break at the recognition site. Thus, in specific embodiments, the target sites corresponding to the upstream and/or downstream homology arm of the targeting vector are within at least 10 nucleotide to about 14 kb of a given recognition site. In specific embodiments, the recognition site is immediately adjacent to at least one or both of the target sites.

The spatial relationship of the target sites that correspond to the homology arms of the targeting vector to the recognition site within the polynucleotide encoding the selection marker can vary. For example, both target sites can be located 5' to the recognition site, both target sites can be located 3' to the recognition site, or the target sites can flank the recognition site.

In specific embodiments, the target genomic locus comprises (i) a 5' target sequence that is homologous to a 5' homology arm; and (ii) a 3' target sequence that is homologous to a 3' homology arm. In specific embodiments, the 5' target sequence and the 3' target sequence is separated by at least 5 kb but less than 3 Mb, at least 5 kb but less than 10 kb, at least 10 kb but less than 20 kb, at least 20 kb but less than 40 kb, at least 40 kb but less than 60 kb, at least 60 kb but less than 80 kb, at least about 80 kb but less than 100 kb, at least 100 kb but less than 150 kb, or at least 150 kb but less than 200 kb, at least about 200 kb but less than about 300 kb, at least about 300 kb but less than about 400 kb, at least about 400 kb but less than about 500 kb, at least about 500 kb but less than about 1 Mb, at least about 1 Mb but less than about 1.5 Mb, at least about 1.5 Mb but less than about 2 Mb, at least about 2 Mb but less than about 2.5 Mb, or at least about 2.5 Mb but less than about 3 Mb.

As used herein, a homology arm and a target site "correspond" or are "corresponding" to one another when the two regions share a sufficient level of sequence identity to one another to act as substrates for a homologous recombination reaction. By "homology" is meant DNA sequences that are either identical or share sequence identity to a corresponding sequence. The sequence identity between a given target site and the corresponding homology arm found on the targeting vector can be any degree of sequence identity that allows for homologous recombination to occur. For example, the amount of sequence identity shared by the homology arm of the targeting vector (or a fragment thereof) and the target site (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination. Moreover, a corresponding region of homology between the homology arm and the corresponding target site can be of any length that is sufficient to promote homologous recombination at the cleaved recognition site. For example, a given homology arm and/or corresponding target site can comprise corresponding regions of homology that are from about 400 bp to about 500 bp, from about 500 bp to about 600 bp, from about 600 bp to about 700 bp, from about 700 bp to about 800 bp, from about 800 bp to about 900 bp, or from about 900 bp to about 1000 bp (such as described for the smallTVEC vectors described elsewhere herein); or at least about 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 100-200, or 200-300 kilobases in length or more (such as described in the LTVEC vectors described elsewhere herein) such that the homology arm has sufficient homology to undergo homologous recombination with the corresponding target sites within the genome of the cell.

For ease of reference the homology arms are referred to herein an upstream and a downstream homology arm. This terminology relates to the relative position of the homology arms to the insert polynucleotide within the targeting vector.

The homology arms of the targeting vector are therefore designed to correspond to a target site with the targeted genomic locus on the Y chromosome or within a challenging target locus. Thus, the homology arms can correspond to a genomic locus that is native to the cell, or alternatively they can correspond to a region of a heterologous or exogenous segment of DNA that was integrated into the Y chromosome, including, but not limited to, transgenes, expression cassettes, or heterologous or exogenous regions of genomic DNA. Alternatively, the homology arms of the targeting vector can correspond to a region of a yeast artificial chromosome (YAC), a bacterial artificial chromosome (BAC), a human artificial chromosome, or any other engineered genomic region contained in an appropriate host cell. Still further the homology arms of the targeting vector can correspond to or be derived from a region of a BAC library, a cosmid library, or a P1 phage library. Thus, in specific embodiments, the homology arms of the targeting vector correspond to a genomic locus on the Y chromosome or to a challenging target locus that is native, heterologous or exogenous to a non-human mammal, a rodent, a human, a rat, a mouse, a hamster a rabbit, a pig, a bovine, a deer, a sheep, a goat, a chicken, a cat, a dog, a ferret, a primate (e.g., marmoset, rhesus monkey), domesticated mammal or an agricultural mammal, an avian, or any other organism of interest. In further embodiments, the homology arms correspond to a genomic locus of the cell that is not targetable using a conventional method or can be targeted only incorrectly or only with significantly low efficiency, in the absence of a nick or double-strand break induced by a nuclease agent. In one embodiment, the homology arms are derived from a synthetic DNA.

In still other embodiments, the upstream and downstream homology arms correspond to the same genome as the targeted genome. In one embodiment, the homology arms are from a related genome, e.g., the targeted genome is a mouse genome of a first strain, and the targeting arms are from a mouse genome of a second strain, wherein the first strain and the second strain are different. In other embodiments, the homology arms are from the genome of the same animal or are from the genome of the same strain, e.g., the targeted genome is a mouse genome of a first strain, and the targeting arms are from a mouse genome from the same mouse or from the same strain.

The targeting vector (such as a large targeting vector) can also comprise a selection cassette or a reporter gene as discussed elsewhere herein. The selection cassette can comprise a nucleic acid sequence encoding a selection marker, wherein the nucleic acid sequence is operably linked to a promoter. Such promoters can be an inducible promoter, a promoter that is endogenous to the report gene or the cell, a promoter that is heterologous to the reporter gene or to the cell, a cell-specific promoter, a tissue-specific promoter manner or a developmental stage-specific promoter. In one embodiment, the selection marker is selected from neomycin phosphotransferase (neo$^r$), hygromycin B phosphotransferase (hyg$^r$), puromycin-N-acetyltransferase (puro$^r$), blasticidin S deaminase (bsr$^r$), xanthine/guanine phosphoribosyl transferase (gpt), and herpes simplex virus thymidine kinase (HSV-k), and a combination thereof. The selection marker of the targeting vector can be flanked by the upstream and downstream homology arms or found either 5' or 3' to the homology arms.

In one embodiment, the targeting vector (such as a large targeting vector) comprises a reporter gene operably linked to a promoter, wherein the reporter gene encodes a reporter protein selected from the group consisting of LacZ, mPlum, mCherry, tdTomato, mStrawberry, J-Red, DsRed, mOrange, mKO, mCitrine, Venus, YPet, enhanced yellow fluorescent protein (EYFP), Emerald, enhanced green fluorescent protein (EGFP), CyPet, cyan fluorescent protein (CFP), Cerulean, T-Sapphire, luciferase, alkaline phosphatase, and a combination thereof. Such reporter genes can be operably linked to a promoter active in the cell. Such promoters can be an inducible promoter, a promoter that is endogenous to the report gene or the cell, a promoter that is heterologous to the reporter gene or to the cell, a cell-specific promoter, a tissue-specific promoter manner or a developmental stage-specific promoter.

In one non-limiting embodiment, the combined use of the targeting vector (including, for example, a large targeting vector) with the nuclease agent results in an increased targeting efficiency compared to the use of the targeting vector alone. In one embodiment, when the targeting vector is used in conjunction with the nuclease agent, targeting efficiency of the targeting vector is increased at least by two-fold, at least three-fold, at least 4-fold, or at least 10-fold when compared to when the targeting vector is used alone.

iii. Large Targeting Vectors

The term "large targeting vector" or "LTVEC" as used herein includes large targeting vectors that comprise homology arms that correspond to and are derived from nucleic acid sequences larger than those typically used by other approaches intended to perform homologous targeting in cells and/or comprising insert polynucleotides comprising nucleic acid sequences larger than those typically used by other approaches intended to perform homologous recombination targeting in cells. In specific embodiments, the homology arms and/or the insert polynucleotide of the LTVEC comprises a genomic sequence of a eukaryotic cell. The size of the LTVEC is too large to enable screening of targeting events by conventional assays, e.g., southern blotting and long-range (e.g., 1 kb-5 kb) PCR. Examples of the LTVEC, include, but are not limited to, vectors derived from a bacterial artificial chromosome (BAC), a human artificial chromosome or a yeast artificial chromosome (YAC). Non-limiting examples of LTVECs and methods for making them are described, e.g., in U.S. Pat. Nos. 6,586,251, 6,596,541, 7,105,348, and WO 2002/036789 (PCT/US01/45375), each of which is herein incorporated by reference.

The LTVEC can be of any length, including, but not limited to, at least about 10 kb, about 15 kb, about 20 kb, about 30 kb, about 40 kb, about 50 kb, about 60 kb, about 70 kb, about 80 kb, about 90 kb, about 100 kb, about 150 kb, about 200 kb, from about 10 kb to about 15 kb, about 15 kb to about 20 kb, about 20 kb to about 30 kb, from about 30 kb to about 50 kb, from about 50 kb to about 300 kb, from about 50 kb to about 75 kb, from about 75 kb to about 100 kb, from about 100 kb to 125 kb, from about 125 kb to about 150 kb, from about 150 kb to about 175 kb, about 175 kb to about 200 kb, from about 200 kb to about 225 kb, from about 225 kb to about 250 kb, from about 250 kb to about 275 kb or from about 275 kb to about 300 kb.

In one embodiment, the LTVEC comprises an insert polynucleotide ranging from about 5 kb to about 200 kb, from about 5 kb to about 10 kb, from about 10 kb to about 20 kb, from about 20 kb to about 30 kb, from about 30 kb to about 40 kb, from about 40 kb to about 50 kb, from about 60 kb to about 70 kb, from about 80 kb to about 90 kb, from about 90 kb to about 100 kb, from about 100 kb to about 110 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb, from about 200 kb to about 250 kb, from about 250 kb to about 300 kb, from about 300 kb to about 350 kb, or from about 350 kb to about 400 kb.

In other instances, the LTVEC design can be such as to allow for the replacement of a given sequence that is from about 5 kb to about 200 kb or from about 5 kb to about 3.0 Mb as described herein. In one embodiment, the replacement is from about 5 kb to about 10 kb, from about 10 kb to about 20 kb, from about 20 kb to about 30 kb, from about 30 kb to about 40 kb, from about 40 kb to about 50 kb, from about 50 kb to about 60 kb, from about 60 kb to about 70 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, from about 190 kb to about 200 kb, from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb.

In one embodiment, the homology arms of the LTVEC are derived from a BAC library, a cosmid library, or a P1 phage library. In other embodiments, the homology arms are derived from the targeted genomic locus of the cell and in some instances the target genomic locus that the LTVEC is designed to target is not targetable using a conventional method. In still other embodiments, the homology arms are derived from a synthetic DNA.

In one embodiment, a sum total of the upstream homology arm and the downstream homology arm in the LTVEC is at least 10 kb. In other embodiments, the upstream homology arm ranges from about 5 kb to about 100 kb. In one embodiment, the downstream homology arm ranges from about 5 kb to about 100 kb. In other embodiments, the sum total of the upstream and downstream homology arms are from about 5 kb to about 10 kb, from about 10 kb to about 20 kb, from about 20 kb to about 30 kb, from about 30 kb to about 40 kb, from about 40 kb to about 50 kb, from about 50 kb to about 60 kb, from about 60 kb to about 70 kb, from about 70 kb to about 80 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb. In one embodiment, the size of the deletion is the same or similar to the size of the sum total of the 5' and 3' homology arms of the LTVEC.

In one embodiment, the LTVEC comprises a selection cassette or a reporter gene as discussed elsewhere herein.

iv. Methods of Integrating an Insert Polynucleotide Near the Recognition Site on the Y Chromosome by Homologous Recombination Methods are provided for modifying a target genomic locus on the Y chromosome in a cell comprising: (a) providing a cell comprising a target genomic locus on the Y chromosome, (b) introducing into the cell a first targeting vector comprising a first insert polynucleotide flanked by a first and a second homology arm corresponding to a first and a second target site; and (c) identifying at least one cell comprising in its genome the first insert polynucleotide integrated at the target genomic locus on the Y chromosome. Similar methods can be performed to target a challenging chromosomal locus. As discussed in detail elsewhere herein, in specific embodiments, the sum total of the first homology arm and the second homology arm of the targeting vector is about 0.5 kb, 1 kb, 1.5 kb, 2 kb, 3 kb, 4 kb, 5 kb, 6 kb, 7 kb, 8 kb, 9 kb, about 0.5 kb to about 1 kb, about 1 kb to about 1.5 kb, about 1.5 kb to about 2 kb, about 2 kb to about 3 kb, about 3 kb to about 4 kb, about 4 kb to about 5 kb, about 5 kb to about 6 kb, about 6 kb to about 7 kb, about 8 kb to about 9 kb, or is at least 10 kb or at least 10 kb and less than 150 kb. In specific embodiments, an LTVEC is employed. In other specific embodiments, a smallTVEC is employed. In one non-limiting embodiment, such methods are performed employing the culture media that promotes the development of XY F0 fertile females disclosed herein and thereby generating XY F0 fertile female animals. In other instance, the methods described herein are employed to produce a targeted genetic modification in the Sry gene, as discussed elsewhere herein.

Further provided are methods for modifying a target genomic locus on the Y chromosome in a cell comprising: (a) providing a cell comprising a target genomic locus on the Y chromosome comprising a recognition site for a nuclease agent, (b) introducing into the cell (i) the nuclease agent, wherein the nuclease agent induces a nick or double-strand break at the first recognition site; and, (ii) a first targeting vector comprising a first insert polynucleotide flanked by a first and a second homology arm corresponding to a first and a second target site located in sufficient proximity to the first recognition site; and (c) identifying at least one cell comprising in its genome the first insert polynucleotide integrated at the target genomic locus on the Y chromosome. Similar methods can be performed to target a challenging target locus. As discussed in detail elsewhere herein, in specific embodiments, the sum total of the first homology arm and the second homology arm of the targeting vector is about 0.5 kb, 1 kb, 1.5 kb, 2 kb, 3 kb, 4 kb, 5 kb, 6 kb, 7 kb, 8 kb, 9 kb, about 0.5 kb to about 1 kb, about 1 kb to about 1.5 kb, about 1.5 kb to about 2 kb, about 2 kb to about 3 kb, about 3 kb to about 4 kb, about 4 kb to about 5 kb, about 5 kb to about 6 kb, about 6 kb to about 7 kb, about 8 kb to about 9 kb, or is at least 10 kb or at least 10 kb and less than 150 kb. In specific embodiments, an LTVEC is employed. In other specific embodiments, a smallTVEC is employed. In one non-limiting embodiment, such methods are performed employing the culture media that promotes the development of XY F0 fertile females disclosed herein and thereby generating XY F0 fertile female animals. In other instance, the methods described herein are employed to produce a targeted genetic modification in the Sry gene, as discussed elsewhere herein.

Various methods can also be employed to identify cells having the insert polynucleotide integrated at the genomic target locus. Insertion of the insert polynucleotide at the genomic target locus results in a "modification of allele". The term "modification of allele" or "MOA" includes the modification of the exact DNA sequence of one allele of a gene(s) or chromosomal locus (loci) in a genome. Examples of "modification of allele (MOA)" include, but are not limited to, deletions, substitutions, or insertions of as little as a single nucleotide or deletions of many kilobases spanning a gene(s) or chromosomal locus (loci) of interest, as well as any and all possible modifications between these two extremes.

In various embodiments, to facilitate identification of the targeted modification, a high-throughput quantitative assay, namely, modification of allele (MOA) assay, is employed. The MOA assay described herein allows a large-scale screening of a modified allele(s) in a parental chromosome following a genetic modification. The MOA assay can be carried out via various analytical techniques, including, but not limited to, a quantitative PCR, e.g., a real-time PCR (qPCR). For example, the real-time PCR comprises a first primer-probe set that recognizes the target locus and a second primer-probe set that recognizes a non-targeted reference locus. In addition, the primer-probe set comprises a fluorescent probe that recognizes the amplified sequence. The quantitative assay can also be carried out via a variety of analytical techniques, including, but not limited to, fluorescence-mediated in situ hybridization (FISH), comparative genomic hybridization, isothermic DNA amplification, quantitative hybridization to an immobilized probe(s), Invader Probes®, MMP Assays®, TaqMan® Molecular Beacon, and Eclipse™ probe technology. (See, for example, US2005/0144655, incorporated by reference herein in its entirety).

In various embodiments, in the presence of the nick or double strand bread, targeting efficiency of a targeting vector (such as a LTVEC or a smallTVEC) at the target genomic locus is at least about 2-fold higher, at least about 3-fold higher, at least about 4-fold higher than in the absence of the nick or double-strand break (using, e.g., the same targeting vector and the same homology arms and corresponding target sites at the genomic locus of interest but in the absence of an added nuclease agent that makes the nick or double strand break).

The various methods set forth above can be sequentially repeated to allow for the targeted integration of any number of insert polynucleotides into a given targeted genomic locus on the Y chromosome or into a challenging target locus. Thus, the various methods provide for the insertion of at least 1, 2, 3, 4, 5, 6, 7, 8, 9, 10, 11, 12, 13, 14, 15, 16, 17, 18, 19, 20 or more insert polynucleotides into the target genomic locus on the Y chromosome or into a challenging target locus. In particular embodiments, such sequential tiling methods allow for the reconstruction of large genomic regions from an animal cell or from a mammalian cell (i.e., a human, a non-human, a rodent, a mouse, a monkey, a rat, a hamster, a domesticated mammal or an agricultural animal) into a targeted genomic locus on a Y chromosome. In such instances, the transfer and reconstruction of genomic regions that include both coding and non-coding regions allow for the complexity of a given region to be preserved by retaining, at least in part, the coding regions, the non-coding regions and the copy number variations found within the native genomic region. Thus, the various methods provide, for example, methods to generate "heterologous" or "exogenous" genomic regions within any mammalian cell or animal of interest. In one non-limiting example, a "humanized" genomic region within a non-human animal is generated.

It is further recognized that along with modifying the target genomic locus on the Y chromosome, the various methods and compositions disclosed herein can be employed to also generate at targeted genetic modification on another chromosome.

v. Polynucleotides of Interest

Any polynucleotide of interest may be contained in the various insert polynucleotides and thereby integrated at the target genomic locus on the Y chromosome or into a challenging target locus. The methods disclosed herein, provide for at least 1, 2, 3, 4, 5, 6 or more polynucleotides of interest to be integrated into the targeted genomic locus.

The polynucleotide of interest within the insert polynucleotide when integrated at the target genomic locus on the Y chromosome or at a challenging target locus can introduce one or more genetic modifications into the cell. The genetic modification can comprise a deletion of an endogenous nucleic acid sequence and/or the addition of an exogenous or heterologous or orthologous polynucleotide into the target genomic locus. In one embodiment, the genetic modification comprises a replacement of an endogenous nucleic acid sequence with an exogenous polynucleotide of interest at the target genomic locus. Thus, methods provided herein allow for the generation of a genetic modification comprising a knockout, a deletion, an insertion, a replacement ("knock-in"), a point mutation, a domain swap, an exon swap, an intron swap, a regulatory sequence swap, a gene swap, or a combination thereof in a target genomic locus on the Y chromosome. Such modifications may occur upon integration of the first, second, third, fourth, fifth, six, seventh, or any subsequent insert polynucleotides into the target genomic locus.

The polynucleotide of interest within the insert polynucleotide and/or integrated at the target genomic locus can comprise a sequence that is native or homologous to the cell it is introduced into; the polynucleotide of interest can be heterologous to the cell it is introduced to; the polynucleotide of interest can be exogenous to the cell it is introduced into; the polynucleotide of interest can be orthologous to the cell it is introduced into; or the polynucleotide of interest can be from a different species than the cell it is introduced into. As used herein "homologous" in reference to a sequence is a sequence that is native to the cell. As used herein, "heterologous" in reference to a sequence is a sequence that originates from a foreign species, or, if from the same species, is substantially modified from its native form in composition and/or genomic locus by deliberate human intervention. As used herein, "exogenous" in reference to a sequence is a sequence that originates from a foreign species. As used herein, "orthologous" is a polynucleotide from one species that is functionally equivalent to a known reference sequence in another species (i.e., a species variant). The polynucleotide of interest can be from any organism of interest including, but not limited to, non-human, a rodent, a hamster, a mouse, a rat, a human, a monkey, an avian, an agricultural mammal or a non-agricultural mammal. The polynucleotide of interest can further comprise a coding region, a non-coding region, a regulatory region, or a genomic DNA. Thus, the $1^{st}$, $2^{nd}$, $3^{rd}$, $4^{th}$, $5^{th}$, $6^{th}$, $7^{th}$, and/or any of the subsequent insert polynucleotides can comprise such sequences.

In one embodiment, the polynucleotide of interest within the insert polynucleotide and/or integrated at the target genomic locus on the Y chromosome is homologous to a mouse nucleic acid sequence, a human nucleic acid, a non-human nucleic acid, a rodent nucleic acid, a rat nucleic acid, a hamster nucleic acid, a monkey nucleic acid, an agricultural mammal nucleic acid, or a non-agricultural mammal nucleic acid. In still further embodiments, the polynucleotide of interest integrated at the target locus is a fragment of a genomic nucleic acid. In one embodiment, the genomic nucleic acid is a mouse genomic nucleic acid, a human genomic nucleic acid, a non-human nucleic acid, a rodent nucleic acid, a rat nucleic acid, a hamster nucleic acid, a monkey nucleic acid, an agricultural mammal nucleic acid or a non-agricultural mammal nucleic acid or a combination thereof.

In one embodiment, the polynucleotide of interest can range from about 500 nucleotides to about 200 kb as described above. The polynucleotide of interest can be from about 500 nucleotides to about 5 kb, from about 5 kb to about 200 kb, from about 5 kb to about 10 kb, from about 10 kb to about 20 kb, from about 20 kb to about 30 kb, from about 30 kb to about 40 kb, from about 40 kb to about 50 kb, from about 60 kb to about 70 kb, from about 80 kb to about 90 kb, from about 90 kb to about 100 kb, from about 100 kb to about 110 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb.

The polynucleotide of interest within the insert polynucleotide and/or inserted at the target genomic locus on the Y chromosome or into a challenging target locus can encode a polypeptide, can encode an miRNA, can encode a long non-coding RNA, or it can comprise any regulatory regions or non-coding regions of interest including, for example, a regulatory sequence, a promoter sequence, an enhancer sequence, a transcriptional repressor-binding sequence, or a deletion of a non-protein-coding sequence, but does not comprise a deletion of a protein-coding sequence. In addition, the polynucleotide of interest within the insert polynucleotide and/or inserted at the target genomic locus on the Y chromosome or at a challenging target locus can encode a protein expressed in the nervous system, the skeletal system, the digestive system, the circulatory system, the muscular system, the respiratory system, the cardiovascular system, the lymphatic system, the endocrine system, the urinary system, the reproductive system, or a combination thereof.

The polynucleotide of interest within the insert polynucleotide and/or integrated at the target genomic locus on the Y chromosome or at a challenging target locus can comprises a genetic modification in a coding sequence. Such genetic modifications include, but are not limited to, a deletion mutation of a coding sequence or the fusion of two coding sequences.

The polynucleotide of interest within the insert polynucleotide and/or integrated at the target genomic locus on the Y chromosome or at a challenging target locus can comprise a polynucleotide encoding a mutant protein. In one embodiment, the mutant protein is characterized by an altered binding characteristic, altered localization, altered expression, and/or altered expression pattern. In one embodiment, the polynucleotide of interest within the insert polynucleotide and/or integrated at the genomic target locus on the Y chromosome or at a challenging target locus comprises at least one disease allele. In such instances, the disease allele can be a dominant allele or the disease allele is a recessive allele. Moreover, the disease allele can comprise a single nucleotide polymorphism (SNP) allele. The polynucleotide of interest encoding the mutant protein can be from any organism, including, but not limited to, a mammal, a non-human mammal, rodent, mouse, rat, a human, a monkey, an agricultural mammal or a domestic mammal polynucleotide encoding a mutant protein.

The polynucleotide of interest within the insert polynucleotide and/or integrated at the target genomic locus on the Y chromosome or at a challenging target locus can also comprise a regulatory sequence, including for example, a promoter sequence, an enhancer sequence, a transcriptional repressor-binding sequence, or a transcriptional terminator sequence. In specific embodiments, the polynucleotide of interest within the insert polynucleotide and/or integrated at the target genomic locus on the Y chromosome or at a challenging target locus comprises a polynucleotide having a deletion of a non-protein-coding sequence, but does not comprise a deletion of a protein-coding sequence. In one embodiment, the deletion of the non-protein-coding sequence comprises a deletion of a regulatory sequence. In another embodiment, the deletion of the regulatory element comprises a deletion of a promoter sequence. In one embodiment, the deletion of the regulatory element comprises a deletion of an enhancer sequence. Such a polynucleotide of interest can be from any organism, including, but not limited to, a mammal, a non-human mammal, rodent, mouse, rat, a human, a monkey, an agricultural mammal or a domestic mammal polynucleotide encoding a mutant protein.

The various methods disclosed herein can be employed to generate a variety of modifications in a challenging genomic locus or in the Y chromosome locus (such as Sry). Such modifications include, for example, a replacement of an endogenous nucleic acid sequence with a homologous or an orthologous nucleic acid sequence; a deletion of an endogenous nucleic acid sequence; a deletion of an endogenous nucleic acid sequence, wherein the deletion ranges from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 300 kb, from about 300 kb to about 400 kb, from about 400 kb to about 500 kb, from about 500 kb to about 600 kb, from about 600 kb to about 700 kb, from about 700 kb to about 800 kb, from about 800 kb to about 900 kb, from about 900 kb to about 1 Mb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb; an insertion of an exogenous nucleic acid sequence; an insertion of an exogenous nucleic acid sequence ranging from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb; an insertion of an exogenous nucleic acid sequence comprising a homologous or an orthologous nucleic acid sequence; an insertion of a chimeric nucleic acid sequence comprising a human and a non-human nucleic acid sequence; an insertion of a conditional allele flanked with site-specific recombinase target sequences; an insertion of a selectable marker or a reporter gene operably linked to a third promoter active in the mammalian cell; or a combination thereof.

III. Methods of Introducing Sequences and Generation of Transgenic Animals

As outlined above, methods and compositions are provided herein to allow for the targeted genetic modification of one or more polynucleotides of interest located on the Y chromosome, at a challenging target locus, or a decrease in the level and/or activity of the Sry protein. It is further recognized that in addition to a targeted genetic modification to a sequence on the Y chromosome or on a challenging target chromosomal locus, additional targeted genetic modification can be made on other chromosomes. Such systems that allow for these targeted genetic modifications can employ a variety of components and for ease of reference, herein the term "targeted genomic integration system" generically includes all the components required for an integration event (i.e. the various nuclease agents, recognition sites, insert DNA polynucleotides, targeting vectors, target genomic locus, and polynucleotides of interest).

The methods provided herein comprise introducing into a cell one or more polynucleotides or polypeptide constructs comprising the various components of the targeted genomic integration system. "Introducing" means presenting to the cell the sequence (polypeptide or polynucleotide) in such a manner that the sequence gains access to the interior of the cell. The methods provided herein do not depend on a particular method for introducing any component of the targeted genomic integration system into the cell, only that the polynucleotide gains access to the interior of a least one cell. Methods for introducing polynucleotides into various cell types are known in the art and include, but are not limited to, stable transfection methods, transient transfection methods, and virus-mediated methods.

In some embodiments, the cells employed in the methods and compositions have a DNA construct stably incorporated into their genome. "Stably incorporated" or "stably introduced" means the introduction of a polynucleotide into the cell such that the nucleotide sequence integrates into the genome of the cell and is capable of being inherited by progeny thereof. Any protocol may be used for the stable incorporation of the DNA constructs or the various components of the targeted genomic integration system.

Transfection protocols as well as protocols for introducing polypeptides or polynucleotide sequences into cells may vary. Non-limiting transfection methods include chemical-based transfection methods include the use of liposomes; nanoparticles; calcium phosphate (Graham et al. (1973). *Virology* 52 (2): 456-67, Bacchetti et al. (1977) *Proc Natl Acad Sci USA* 74 (4): 1590-4 and, Kriegler, M (1991). *Transfer and Expression: A Laboratory Manual*. New York: W. H. Freeman and Company. pp. 96-97); dendrimers; or cationic polymers such as DEAE-dextran or polyethylenimine. Non chemical methods include electroporation; Sono-poration; and optical transfection. Particle-based transfection include the use of a gene gun, magnet assisted transfection (Bertram, J. (2006) *Current Pharmaceutical Biotechnology* 7, 277-28). Viral methods can also be used for transfection.

In one embodiment, the nuclease agent is introduced into the cell simultaneously with the targeting vector, the small-TVEC, or the large targeting vector (LTVEC). Alternatively, the nuclease agent is introduced separately from the targeting vector, smallTVEC, or the LTVEC over a period of time. In one embodiment, the nuclease agent is introduced prior to the introduction of the targeting vector, smallTVEC, or the LTVEC, while in other embodiments, the nuclease agent is introduced following introduction of the targeting vector, smallTVEC, or the LTVEC.

Non-human animals can be generated employing the various methods disclosed herein. Such methods comprises (1) integrating one or more polynucleotide of interest at the target genomic locus of the Y chromosome of a pluripotent cell of the non-human animal to generate a genetically modified pluripotent cell comprising the insert polynucleotide in the targeted genomic locus of the Y chromosome employing the methods disclosed herein; (2) selecting the genetically modified pluripotent cell having the one or more polynucleotides of interest at the target genomic locus of the Y chromosome; (3) introducing the genetically modified pluripotent cell into a host embryo of the non-human animal at a pre-morula stage; and (4) implanting the host embryo comprising the genetically modified pluripotent cell into a surrogate mother to generate an F0 generation derived from the genetically modified pluripotent cell. Similar methods can be employed to target a challenging target chromosomal locus. The non-human animal can be a non-human mammal, a rodent, a mouse, a rat, a hamster, a monkey, an agricultural mammal or a domestic mammal, or a fish or a bird.

The pluripotent cell can be a human ES cell, a non-human ES cell, a rodent ES cell, a mouse ES cell, a rat ES cell, a hamster ES cell, a monkey ES cell, an agricultural mammal ES cell or a domesticated mammal ES cell. In other embodiments, the pluripotent cell is a mammalian cell, human cell, a non-human mammalian cell, a human pluripotent cell, a human ES cell, a human adult stem cell, a developmentally-restricted human progenitor cell, a human iPS cell, a human cell, a rodent cell, a rat cell, a mouse cell, a hamster cell. In one embodiment, the targeted genetic modification decreases the level and/or activity of the Sry protein. In such instances, the pluripotent cell can comprise an XY ES cell or an XY iPS cell. Methods of culturing such cells to promote the development of F0 fertile XY female animals are described in detail elsewhere herein.

Nuclear transfer techniques can also be used to generate the non-human mammalian animals. Briefly, methods for nuclear transfer include the steps of: (1) enucleating an oocyte; (2) isolating a donor cell or nucleus to be combined with the enucleated oocyte; (3) inserting the cell or nucleus into the enucleated oocyte to form a reconstituted cell; (4) implanting the reconstituted cell into the womb of an animal to form an embryo; and (5) allowing the embryo to develop. In such methods oocytes are generally retrieved from deceased animals, although they may be isolated also from either oviducts and/or ovaries of live animals. Oocytes can be matured in a variety of medium known to those of ordinary skill in the art prior to enucleation. Enucleation of the oocyte can be performed in a number of manners well known to those of ordinary skill in the art. Insertion of the donor cell or nucleus into the enucleated oocyte to form a reconstituted cell is usually by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell is typically activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, are typically cultured in medium well known to those of ordinary skill in the art and then transferred to the womb of an animal. See, for example, US20080092249, WO/1999/005266A2, US20040177390, WO/2008/017234A1, and U.S. Pat. No. 7,612,250, each of which is herein incorporated by reference.

Other methods for making a non-human animal comprising in its germline one or more genetic modifications as described herein is provided, comprising: (a) modifying a targeted genomic locus on the Y chromosome of a non-human animal in a prokaryotic cell employing the various methods described herein; (b) selecting a modified prokaryotic cell comprising the genetic modification at the targeted genomic locus; (c) isolating the genetically modified targeting vector from the genome of the modified prokaryotic cell; (d) introducing the genetically modified targeting vector into a pluripotent cell of the non-human animal to generate a genetically modified pluripotent cell comprising the insert nucleic acid at the targeted genomic locus of the Y chromosome; (e) selecting the genetically modified pluripotent cell; (f) introducing the genetically modified pluripotent cell into a host embryo of the non-human animal at a pre-morula stage; and (g) implanting the host embryo comprising the genetically modified pluripotent cell into a surrogate mother to generate an F0 generation derived from the genetically modified pluripotent cell. In such methods the targeting vector can comprise a large targeting vector or a smallT-VEC. Similar methods can be employed to target a challenging target locus. The non-human animal can be a non-human mammal, a rodent, a mouse, a rat, a hamster, a monkey, an agricultural mammal or a domestic mammal. The pluripotent cell can be a human ES cell, a non-human ES cell, a rodent ES cell, a mouse ES cell, a rat ES cell, a hamster ES cell, a monkey ES cell, an agricultural mammal ES cell or a domestic mammal ES cell. In other embodiments, the pluripotent cell is a mammalian cell, human cell, a non-human mammalian cell, a human pluripotent cell, a human ES cell, a human adult stem cell, a developmentally-restricted human progenitor cell, a human iPS cell, a human cell, a rodent cell, a rat cell, a mouse cell, a hamster cell. In one embodiment, the targeted genetic modification decreases the level and/or activity of the Sry protein. In such instances, the pluripotent cell can comprise an XY ES cell or an XY iPS cell. Methods of culturing such cells to promote the development of F0 fertile XY female animals are described in detail elsewhere herein.

In further methods, the isolating step (c) further comprises (c1) linearizing the genetically modified targeting vector (i.e., the genetically modified LTVEC). In still further embodiments, the introducing step (d) further comprises (d1) introducing a nuclease agent as described herein into the pluripotent cell. In one embodiment, selecting steps (b) and/or (e) are carried out by applying a selectable agent as described herein to the prokaryotic cell or the pluripotent cell. In one embodiment, selecting steps (b) and/or (e) are carried out via a modification of allele (MOA) assay as described herein.

Further methods for modifying a target genomic locus of an animal cell via bacterial homologous recombination (BHR) in a prokaryotic cell are provided and comprise: (a) providing a prokaryotic cell comprising a target genomic locus of the Y chromosome; (b) introducing into the prokaryotic cell a targeting vector (as described above) comprising an insert polynucleotide flanked with a first upstream homology arm and a first downstream homology arm, wherein the insert polynucleotide comprises a mammalian genomic region, and introducing into the prokaryotic cell a nuclease agent that makes a nick or double-strand break at or near the first recognition site, and (c) selecting a targeted prokaryotic cell comprising the insert polynucleotide at the target genomic locus of the chromosome, wherein the prokaryotic cell is capable of expressing a recombinase that mediates the BHR. Similar methods can be employed to target a challenging target locus. Steps (a)-(c) can be serially repeated as disclosed herein to allow the introduction of multiple insert polynucleotides at the targeted genomic locus in the prokaryotic cell. Once the targeted genomic locus is "built" with the prokaryotic cell, a targeting vector comprising the modified target genomic locus of the Y chromosome can be isolated from the prokaryotic cell and introduced into a target genomic locus of the Y chromosome within a mammalian cell. Mammalian cells comprising the modified genomic locus of the Y chromosome can then be made into non-human transgenic animals.

Further methods for modifying a target genomic locus of an animal cell via bacterial homologous recombination (BHR) in a prokaryotic cell are provided and comprise: (a) providing a prokaryotic cell comprising a target genomic locus of the Y chromosome; (b) introducing into the prokaryotic cell a targeting vector (as described above) comprising an insert polynucleotide flanked with a first upstream homology arm and a first downstream homology arm, wherein the insert polynucleotide comprises a mammalian genomic region, and (c) selecting a targeted prokaryotic cell comprising the insert polynucleotide at the target genomic locus of the chromosome, wherein the prokaryotic cell is capable of expressing a recombinase that mediates the BHR. Similar methods can be employed to target a challenging target locus. Steps (a)-(c) can be serially repeated as disclosed herein to allow the introduction of multiple insert polynucleotides at the targeted genomic locus in the prokaryotic cell. Once the targeted genomic locus is "built" with the prokaryotic cell, a targeting vector comprising the modified target genomic locus of the Y chromosome can be isolated from the prokaryotic cell and introduced into a target genomic locus of the Y chromosome within a mammalian cell. Mammalian cells comprising the modified genomic locus of the Y chromosome can then be made into non-human transgenic animals In some embodiments, various genetic modifications of the target genomic loci described herein can be carried out by a series of homologous recombination reactions (BHR) in bacterial cells using an LTVEC derived from Bacterial Artificial Chromosome (BAC) DNA using VELOCIGENE® genetic engineering technology (see, e.g., U.S. Pat. No. 6,586,251 and Valenzuela, D. M. et al. (2003), High-throughput engineering of the mouse genome coupled with high-resolution expression analysis, *Nature Biotechnology* 21(6): 652-659, which is incorporated herein by reference in their entireties).

In some embodiments, targeted XY pluripotent and/or totipotent cells (i.e., X YES cells or XY iPS cells) comprising various genetic modifications as described herein are used as insert donor cells and introduced into a pre-morula stage embryo from a corresponding organism, e.g., an 8-cell stage mouse embryo, via the VELOCIMOUSE® method (see, e.g., U.S. Pat. No. 7,576,259, U.S. Pat. No. 7,659,442, U.S. Pat. No. 7,294,754, and US 2008-0078000 A1, all of which are incorporated by reference herein in their entireties). The non-human animal embryo comprising the genetically modified XY pluripotent and/or totipotent cells (i.e., XY ES cells or XY iPS cells) is incubated until the blastocyst stage and then implanted into a surrogate mother to produce an F0 generation. In some embodiments, targeted mammalian ES cells comprising various genetic modifications as described herein are introduced into a blastocyst stage embryo. Non-human animals bearing the genetically modified genomic locus of the Y chromosome can be identified via modification of allele (MOA) assay as described herein. The resulting F0 generation non-human animal derived from the genetically modified XY pluripotent and/or totipotent cells (i.e., X YES cells or XY iPS cells) is crossed to a wild-type non-human animal to obtain F1 generation offspring. Following genotyping with specific primers and/or probes, F1 non-human animals that are heterozygous for the genetically modified genomic locus are crossed to each other to produce F2 generation non-human animal offspring that are homozygous for the genetically modified genomic locus of the Y chromosome or for the genetically modified challenging target locus.

IV. Cells and Expression Cassettes

The various methods described herein employ a genomic locus targeting system for the Y chromosome or for a challenging target locus in a cell. Such cells include prokaryotic cells such as bacterial cells including *E. coli*, or eukaryotic cells such as yeast, insect, amphibian, plant, or mammalian cells, including, but not limited to a mouse cell, a rat cell, a rabbit cell, a pig cell, a bovine cell, a deer cell, a sheep cell, a goat cell, a chicken cell, a cat cell, a dog cell, a ferret cell, a primate (e.g., marmoset, rhesus monkey) cell, and the like and cells from domesticated mammals or cells from agricultural mammals. Some cells are non-human, particularly non-human mammalian cells. In some embodiments, for those mammals for which suitable genetically modifiable pluripotent cells are not readily available, other methods are employed to reprogram somatic cells into pluripotent cells, e.g., via introduction into somatic cells of a combination of pluripotency-inducing factors, including, but not limited to, Oct3/4, Sox2, KLF4, Myc, Nanog, LIN28, and Glis1. In such methods, the cell can also be a mammalian cell, human cell, a non-human mammalian cell, a non-human cell, a cell from a rodent, a rat, a mouse, a hamster, a fibroblast cell or any other host cell. In other embodiments, the cell is a pluripotent cell, an induced pluripotent stem (iPS) cell, a non-human embryonic stem (ES) cell. Such cells include pluripotent cells, including, for example, induced pluripotent stem (iPS) cells, mouse embryonic stem (ES) cells, rat embryonic stem (ES) cells, human embryonic (ES) cells, or developmentally restricted human progenitor cells, a rodent embryonic stem (ES) cell, a mouse embryonic stem (ES) cell or a rat embryonic stem (ES) cell.

The terms "polynucleotide," "polynucleotide sequence," "nucleic acid sequence," and "nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Polynucleotides can comprise deoxyribonucleotides and ribonucleotides include both naturally occurring molecules and synthetic analogues, and any combination these. The polynucleotides provided herein also encompass all forms of sequences including, but not limited to, single-stranded forms, double-stranded forms, hairpins, stem-and-loop structures, and the like.

Further provided are recombinant polynucleotides. The terms "recombinant polynucleotide" and "recombinant DNA construct" are used interchangeably herein. A recombinant construct comprises an artificial or heterologous combination of nucleic acid sequences, e.g., regulatory and coding sequences that are not found together in nature. In other embodiments, a recombinant construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that is used to transform the host cells as is well known to those skilled in the art. For example, a plasmid vector can be used. Screening may be accomplished by Southern analysis of DNA, Northern analysis of mRNA expression, immunoblotting analysis of protein expression, or phenotypic analysis, among others.

In specific embodiments, one or more of the components described herein can be provided in an expression cassette for expression in the pluripotent and/or totipotent cell. The cassette can include 5' and 3' regulatory sequences operably linked to a polynucleotide provided herein. "Operably linked" means a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, operably linked means that the coding regions are in the same reading frame. In another instance, a nucleic acid sequence encoding a protein may be operably linked to regulatory sequences (e.g., promoter, enhancer, silencer sequence, etc.) so as to retain proper transcriptional regulation. The cassette may additionally contain at least one additional polynucleotide of interest to be co-introduced into the ES cell. Alternatively, the additional polynucleotide of interest can be provided on multiple expression cassettes. Such an expression cassette is provided with a plurality of restriction sites and/or recombination sites for insertion of a recombinant polynucleotide to be under the transcriptional regulation of the regulatory regions. The expression cassette may additionally contain selection marker genes.

The expression cassette can include in the 5'-3' direction of transcription, a transcriptional and translational initiation region (i.e., a promoter), a recombinant polynucleotide provided herein, and a transcriptional and translational termination region (i.e., termination region) functional in mammalian cell or a host cell of interest. The regulatory regions (i.e., promoters, transcriptional regulatory regions, and transcriptional and translational termination regions) and/or a polynucleotide provided herein may be native/analogous to the host cell or to each other. Alternatively, the regulatory regions and/or a polynucleotide provided herein may be heterologous to the host cell or to each other. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. Alternatively, the regulatory regions and/or a recombinant polynucleotide provided herein may be entirely synthetic.

The termination region may be native with the transcriptional initiation region, may be native with the operably linked recombinant polynucleotide, may be native with the host cell, or may be derived from another source (i.e., foreign or heterologous) to the promoter, the recombinant polynucleotide, the host cell, or any combination thereof.

In preparing the expression cassette, the various DNA fragments may be manipulated, so as to provide for the DNA sequences in the proper orientation. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the expression cassettes provided herein. The promoters can be selected based on the desired outcome. It is recognized that different applications can be enhanced by the use of different promoters in the expression cassettes to modulate the timing, location and/or level of expression of the polynucleotide of interest. Such expression constructs may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

Non-limiting embodiments include:

1. An in vitro culture comprising
   (a) a non-human mammalian XY embryonic stem (ES) cell having a modification that decreases the level and/or activity of an Sry protein; and,
   (b) a medium comprising a base medium and supplements suitable for maintaining the non-human mammalian ES cell in culture, wherein the medium exhibits one or more of the following characteristic: an osmolality from about 200 mOsm/kg to less than about 329 mOsm/kg; a conductivity of about 11 mS/cm to about 13 mS/cm; a salt of an alkaline metal and a halide in a concentration of about 50 mM to about 110 mM; a carbonic acid salt concentration of about 17 mM to about 30 mM; a total alkaline metal halide salt and carbonic acid salt concentration of about 85 mM to about 130 mM; and/or a combination of any two or more thereof.

2. The in vitro culture of claim 1, wherein the non-human mammalian XY ES cell is from a rodent.

3. The in vitro culture of claim 2, wherein the rodent is a mouse.

4. The in vitro culture of embodiment 3, wherein the mouse XY ES cell is a VGF1 mouse ES cell.

5. The in vitro culture of embodiment 2, wherein the rodent is a rat or a hamster.

6. The in vitro culture of any one of embodiments 1-5, wherein the decreased level and/or activity of the Sry protein is from a genetic modification in the Sry gene.

7. The in vitro culture of embodiment 6, wherein the genetic modification in the Sry gene comprises an insertion of one or more nucleotides, a deletion of one or more nucleotides, a substitution of one or more nucleotides, a knockout, a knockin, a replacement of an endogenous nucleic acid sequence with a heterologous nucleic acid sequence or a combination thereof.

8. The in vitro culture of any one of embodiments 1-7, wherein the non-human mammalian ES cell comprises one, two, three or more targeted genetic modifications.

9. The in vitro culture of embodiment 8, wherein the targeted genetic modification comprises an insertion, a deletion, a knockout, knockin, a point mutation, or a combination thereof.

10. The in vitro culture of embodiment 8, wherein the targeted genetic modification comprises at least one insertion of a heterologous polynucleotide into the genome of the XY ES cell.

11. The in vitro culture of any one of embodiments 8-10, wherein the targeted genetic modification is on an autosome.

12. The in vitro culture of any one of embodiments 1-11, wherein the base medium exhibits 50±5 mM NaCl, 26±5 mM carbonate, and 218±22 mOsm/kg.

13. The in vitro culture of any one of embodiments 1-11, wherein the base medium exhibits about 3 mg/mL NaCl, 2.2 mg/mL sodium bicarbonate, and 218 mOsm/kg.

14. The in vitro culture of any one of embodiments 1-11, wherein the base medium exhibits 87±5 mM NaCl, 18±5 mM carbonate, and 261±26 mOsm/kg.

15. The in vitro culture of any one of embodiments 1-11, wherein the base medium exhibits about 5.1 mg/mL NaCl, 1.5 mg/mL sodium bicarbonate, and 261 mOsm/kg.

16. The in vitro culture of any one of embodiments 1-11, wherein the base medium exhibits 110±5 mM NaCl, 18±5 mM carbonate, and 294±29 mOsm/kg.

17. The in vitro culture of any one of embodiments 1-11, wherein the base medium exhibits about 6.4 mg/mL NaCl, 1.5 mg/mL sodium bicarbonate, and 294 mOsm/kg.

18. The in vitro culture of any one of embodiments 1-11, wherein the base medium exhibits 87±5 mM NaCl, 26±5 mM carbonate, and 270±27 mOsm/kg.

19. The in vitro culture of any one of embodiments 1-11, wherein the base medium exhibits about 5.1 mg/mL NaCl, 2.2 mg/mL sodium bicarbonate, and 270 mOsm/kg.

20. The in vitro culture of any one of embodiments 1-11, wherein the base medium exhibits 87±5 mM NaCl, 26±5 mM carbonate, 86±5 mM glucose, and 322±32 mOsm/kg.

21. The in vitro culture of any one of embodiments 1-11, wherein the base medium exhibits about 5.1 mg/mL NaCl, 2.2 mg/mL sodium bicarbonate, 15.5 mg/mL glucose, and 322 mOsm/kg.

22. The in vitro culture of any one of embodiments 1-21, wherein upon introduction of the non-human mammalian XY ES cells into a host embryo and following gestation of the host embryo, at least 80% of the F0 non-human mammals are XY females which upon attaining sexual maturity the F0 XY female non-human mammal is fertile.

23. A method for making a fertile female XY non-human mammal in an F0 generation, comprising:
   (a) culturing a donor non-human mammalian XY embryonic stem (ES) cell having a modification that decreases the level and/or activity of an Sry protein in a medium comprising a base medium and supplements suitable for maintaining the non-human mammalian ES cell in culture, wherein the medium exhibits a characteristic comprising one or more of the following: an osmolality from about 200 mOsm/kg to less than about 329 mOsm/kg; a conductivity of about 11 mS/cm to about 13 mS/cm; a salt of an alkaline metal and a halide in a concentration of about 50 mM to about 110 mM; a carbonic acid salt concentration of about 17 mM to about 30 mM; a total alkaline metal halide salt and carbonic acid salt concentration of about 85 mM to about 130 mM; and/or a combination of any two or more thereof;
   (b) introducing the donor XY non-human mammalian ES cell into a host embryo;
   (c) gestating the host embryo; and,
   (d) obtaining an F0 XY female non-human mammal, wherein upon attaining sexual maturity the F0 XY female non-human mammal is fertile.

24. The method of embodiment 23, wherein the non-human mammalian XY ES cell is from a rodent.

25. The method of embodiment 24, wherein the rodent is a mouse.

26. The method of embodiment 25, wherein the mouse XY ES cell is a VGF1 mouse ES cell.

27. The method of embodiment 24, wherein the rodent is a rat or a hamster.

28. The method of any one of embodiments 23-27, wherein the decreased level and/or activity of the Sry protein is from a genetic modification in the Sry gene.

29. The method of embodiment 28, wherein the genetic modification in the Sry gene comprises an insertion of one or more nucleotides, a deletion of one or more nucleotides, a substitution of one or more nucleotides, a knockout, a knockin, a replacement of an endogenous nucleic acid sequence with a heterologous nucleic acid sequence or a combination thereof.

30. The method of any one of embodiments 23-29, wherein the non-human mammalian ES cell comprises one, two, three or more targeted genetic modifications.

31. The method of embodiment 30, wherein the targeted genetic modification comprises an insertion, a deletion, a knockout, a knockin, a point mutation, or a combination thereof.

32. The method of embodiment 30, wherein the targeted genetic modification comprises at least one insertion of a heterologous polynucleotide into a genome of the XY ES cell.

33. The method of any one of embodiments 30-32, wherein the targeted genetic modification is on an autosome.

34. The method of any one of embodiments 23-33, wherein the base medium exhibits 50±5 mM NaCl, 26±5 mM carbonate, and 218±22 mOsm/kg.

35. The method of any one of embodiments 23-33, wherein the base medium exhibits about 3 mg/mL NaCl, 2.2 mg/mL sodium bicarbonate, and 218 mOsm/kg.

36. The method of any one of embodiments 23-33, wherein the base medium exhibits 87±5 mM NaCl, 18±5 mM carbonate, and 261±26 mOsm/kg.

37. The method of any one of embodiments 23-33, wherein the base medium exhibits about 5.1 mg/mL NaCl, 1.5 mg/mL sodium bicarbonate, and 261 mOsm/kg.

38. The method of any one of embodiments 23-33, wherein the base medium exhibits 110±5 mM NaCl, 18±5 mM carbonate, and 294±29 mOsm/kg.

39. The method of any one of embodiments 23-33, wherein the base medium exhibits about 6.4 mg/mL NaCl, 1.5 mg/mL sodium bicarbonate, and 294 mOsm/kg.

40. The method of any one of embodiments 23-33, wherein the base medium exhibits 87±5 mM NaCl, 26±5 mM carbonate, and 270±27 mOsm/kg.

41. The method of any one of embodiments 23-33, wherein the base medium exhibits about 5.1 mg/mL NaCl, 2.2 mg/mL sodium bicarbonate, and 270 mOsm/kg.

42. The method of any one of embodiments 23-33, wherein the base medium exhibits 87±5 mM NaCl, 26±5 mM carbonate, 86±5 mM glucose, and 322±32 mOsm/kg.

43. The method of any one of embodiments 23-33, wherein the base medium exhibits about 5.1 mg/mL NaCl, 2.2 mg/mL sodium bicarbonate, 15.5 mg/mL glucose, and 322 mOsm/kg.

44. A method of producing a transgenic non-human mammal homozygous for a targeted genetic mutation in the F1 generation comprising: (a) crossing an F0 XY fertile female having a decreased level and/or activity of the Sry protein with a cohort clonal sibling, derived from the same ES cell clone, F0 XY male non-human mammal, wherein the F0 XY fertile female non-human mammal and the F0 XY male non-human mammal each is heterozygous for the genetic mutation; and, (b) obtaining an F1 progeny mouse that is homozygous for the genetic modification.

45. A method for modifying a target genomic locus on the Y chromosome in a cell comprising: (a) providing a cell comprising a target genomic locus on the Y chromosome comprising a recognition site for a nuclease agent, (b) introducing into the cell (i) the nuclease agent, wherein the nuclease agent induces a nick or double-strand break at the first recognition site; and, (ii) a first targeting vector comprising a first insert polynucleotide flanked by a first and a second homology arm corresponding to a first and a second target site located in sufficient proximity to the first recognition site, wherein a sum total of the first homology arm and the second homology arm is at least 4 kb but less than 150 kb; and, (c) identifying at least one cell comprising in its genome the first insert polynucleotide integrated at the target genomic locus.

46. A method for modifying a target genomic locus on the Y chromosome in a cell comprising:
(a) providing a cell comprising a target genomic locus on the Y chromosome comprising a recognition site for a nuclease agent,
(b) introducing into the cell a first targeting vector comprising a first insert polynucleotide flanked by a first and a second homology arm corresponding to a first and a second target site, wherein a sum total of the first homology arm and the second homology arm is at least 4 kb but less than 150 kb; and,
(c) identifying at least one cell comprising in its genome the first insert polynucleotide integrated at the target genomic locus.

47. The method of embodiment 45 or 46, wherein the cell is a mammalian cell.

48. The method of embodiment 47, wherein the mammalian cell is a non-human cell.

49. The method of embodiment 47, wherein the mammalian cell is from a rodent.

50. The method of embodiment 49, wherein the rodent is a rat, a mouse or a hamster.

51. The method of any one of embodiments 45-50, wherein the cell is a pluripotent cell.

52. The method of any one of embodiments 45-50, wherein the mammalian cell is an induced pluripotent stem (iPS) cell.

53. The method of embodiment 51, wherein the pluripotent cell is a non-human embryonic stem (ES) cell.

54. The method of embodiment 51, wherein the pluripotent cell is a rodent embryonic stem (ES) cell, a mouse embryonic stem (ES) cell or a rat embryonic stem (ES) cell.

55. The method of any one of embodiments 45 and 47-54, wherein the nuclease agent is an mRNA encoding a nuclease.

56. The method of any one of embodiments 45 and 47-54, wherein the nuclease agent is a zinc finger nuclease (ZFN).

57. The method of any one of embodiments 45 and 47-54, wherein the nuclease agent is a Transcription Activator-Like Effector Nuclease (TALEN).

58. The method of any one of embodiments 45 and 47-54, wherein the nuclease agent is a meganuclease.

59. The method any one of embodiments 45 and 47-54, wherein the nuclease agent is a CRISPR RNA guided Cas9 endonuclease.

60. A method for modifying the Y chromosome comprising exposing the Y chromosome to a Cas protein and a CRISPR RNA in the presence of a large targeting vector (LTVEC) comprising a nucleic acid sequence of at least 10 kb, wherein following exposure to the Cas protein, the CRISPR RNA, and the LTVEC, the Y chromosome is modified to contain at least 10 kb nucleic acid sequence.

61. The method of embodiment 60, wherein the LTVEC comprises a nucleic acid sequence of at least 20 kb, at least 30 kb, at least 40 kb, at least 50 kb, at least 60 kb, at least 70 kb, at least 80 kb, or at least 90 kb.

62. The method of embodiment 60, wherein the LTVEC comprises a nucleic acid sequence of at least 100 kb, at least 150 kb, or at least 200 kb.

63. A method for modifying a target genomic locus on the Y chromosome, comprising: (a) providing a mammalian cell comprising the target genomic locus on the Y chromosome, wherein the target genomic locus comprises a guide RNA (gRNA) target sequence; (b) introducing into the mammalian cell: (i) a large targeting vector (LTVEC) comprising a first nucleic acid flanked with targeting arms homologous to the target genomic locus, wherein the LTVEC is at least 10 kb; (ii) a first expression construct comprising a first promoter operably linked to a second nucleic acid encoding a Cas protein, and (iii) a second expression construct comprising a second promoter operably linked to a third nucleic acid encoding a guide RNA (gRNA) comprising a nucleotide sequence that hybridizes to the gRNA target sequence and a trans-activating CRISPR RNA (tracrRNA), wherein the first and the second promoters are active in the mammalian cell; and (c) identifying a modified mammalian cell comprising a targeted genetic modification at the target genomic locus on the Y chromosome.

64. The method of embodiment 63, wherein the LTVEC is at least 15 kb, at least 20 kb, at least 30 kb, at least 40 kb, at least 50 kb, at least 60 kb, at least 70 kb, at least 80 kb, or at least 90 kb.

65. The method of embodiment 63, wherein the LTVEC is at least 100 kb, at least 150 kb, or at least 200 kb.

66. The method of embodiment 63, wherein the mammalian cell is a non-human mammalian cell.

67. The method of embodiment 63, wherein the mammalian cell is a fibroblast cell.

68. The method of embodiment 63, wherein the mammalian cell is from a rodent.

69. The method of embodiment 68, wherein the rodent is a rat, a mouse, or a hamster.

70. The method of embodiment 63, wherein the mammalian cell is a pluripotent cell.

71. The method of embodiment 70, wherein the pluripotent cell is an induced pluripotent stem (iPS) cell.

72. The method of embodiment 70, wherein the pluripotent cell is a mouse embryonic stem (ES) cell or a rat embryonic stem (ES) cell.

73. The method of embodiment 70, wherein the pluripotent cell is a developmentally restricted human progenitor cell.

74. The method of embodiment 63, wherein the Cas protein is a Cas9 protein.

75. The method of embodiment 74, wherein the gRNA target sequence is immediately flanked by a Protospacer Adjacent Motif (PAM) sequence.

76. The method of embodiment 63, wherein the sum total of 5' and 3' homology arms of the LTVEC is from about 10 kb to about 150 kb.

77. The method of embodiment 76, wherein the sum total of the 5' and the 3' homology arms of the LTVEC is from about 10 kb to about 20 kb, from about 20 kb to about 40 kb, from about 40 kb to about 60 kb, from about 60 kb to about 80 kb, from about 80 kb to about 100 kb, from about 100 kb to about 120 kb, or from about 120 kb to 150 kb.

78. The method of embodiment 63, wherein the targeted genetic modification comprises: (a) a replacement of an endogenous nucleic acid sequence with a homologous or an orthologous nucleic acid sequence; (b) a deletion of an endogenous nucleic acid sequence; (c) a deletion of an endogenous nucleic acid sequence, wherein the deletion ranges from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb; (d) insertion of an exogenous nucleic acid sequence; (e) insertion of an exogenous nucleic acid sequence ranging from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, or from about 350 kb to about 400 kb; (f) insertion of an exogenous nucleic acid sequence comprising a homologous or an orthologous nucleic acid sequence; (g) insertion of a chimeric nucleic acid sequence comprising a human and a non-human nucleic acid sequence; (h) insertion of a conditional allele flanked with site-specific recombinase target sequences; (i) insertion of a selectable marker or a reporter gene operably linked to a third promoter active in the mammalian cell; or (j) a combination thereof.

79. The method of embodiment 63, wherein the target genomic locus comprises (i) a 5' target sequence that is homologous to a 5' homology arm; and (ii) a 3' target sequence that is homologous to a 3' homology arm.

80. The method of embodiment 79, wherein the 5' target sequence and the 3' target sequence is separated by at least 5 kb but less than 3 Mb.

81. The method of embodiment 79, wherein the 5' target sequence and the 3' target sequence is separated by at least 5 kb but less than 10 kb, at least 10 kb but less than 20 kb, at least 20 kb but less than 40 kb, at least 40 kb but less than 60 kb, at least 60 kb but less than 80 kb, at least about 80 kb but less than 100 kb, at least 100 kb but less than 150 kb, or at least 150 kb but less than 200 kb, at least about 200 kb but less than about 300 kb, at least about 300 kb but less than about 400 kb, at least about 400 kb but less than about 500 kb, at least about 500 kb but less than about 1 Mb, at least about 1 Mb but less than about 1.5 Mb, at least about 1.5 Mb but less than about 2 Mb, at least about 2 Mb but less than about 2.5 Mb, or at least about 2.5 Mb but less than about 3 Mb.

82. The method of embodiment 63, wherein the first and the second expression constructs are on a single nucleic acid molecule.

83. The method of embodiment 63, wherein the target genomic locus comprises the Sry locus.

84. A method for targeted genetic modification on the Y chromosome of a non-human animal, comprising: (a) modifying a genomic locus of interest on the Y chromosome of a non-human pluripotent cell according to the method of embodiment 4, thereby producing a genetically modified non-human pluripotent cell comprising a targeted genetic modification on the Y chromosome; (b) introducing the modified non-human pluripotent cell of (a) into a non-human host embryo; and (c) gestating the non-human host embryo comprising the modified pluripotent cell in a surrogate mother, wherein the surrogate mother produces F0 progeny comprising the targeted genetic modification, wherein the targeted genetic modification is capable of being transmitted through the germline.

85. The method of embodiment 84, wherein the genomic locus of interest comprises the Sry locus.

86. A method for modifying a target genomic locus on the Y chromosome in a cell comprising: (a) providing a cell comprising a target genomic locus on the Y chromosome comprising a recognition site for a nuclease agent, (b) introducing into the cell (i) the nuclease agent, wherein the nuclease agent induces a nick or double-strand break at the first recognition site; and, (ii) a first targeting vector comprising a first insert polynucleotide flanked by a first and a second homology arms corresponding to a first and a second target site located in sufficient proximity to the first recognition site, wherein the length of the first homology arm and/or the second homology arm is at least 400 bp but less than 1000 bp; and, (c) identifying at least one cell comprising in its genome the first insert polynucleotide integrated at the target genomic locus.

87. The method of embodiment 86, wherein the length of the first homology arm and/or the second homology arm is from about 700 bp to about 800 bp.

88. The method of embodiment 86, wherein the modification comprises a deletion of an endogenous nucleic acid sequence.

89. The method of embodiment 88, wherein the deletion ranges from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, or from about 150 kb to about 200 kb, from about 200 kb to about 300 kb, from about 300 kb to about 400 kb, from about 400 kb to about 500 kb, from about 500 kb to about 1 Mb, from about 1 Mb to about 1.5 Mb, from about 1.5 Mb to about 2 Mb, from about 2 Mb to about 2.5 Mb, or from about 2.5 Mb to about 3 Mb.

90. The method of embodiment 88, wherein the deletion is at least 500 kb.

The present methods and compositions may be embodied in many different forms and should not be construed as limited to the embodiments set forth herein; rather, these embodiments are provided so that this disclosure will satisfy applicable legal requirements Like numbers refer to like elements throughout.

Many modifications and other embodiments of the methods and compositions set forth herein will come to mind to one skilled in the art to which this methods and compositions pertains having the benefit of the teachings presented in the foregoing descriptions and the associated drawings. Therefore, it is to be understood that the methods and compositions are not to be limited to the specific embodiments disclosed and that modifications and other embodiments are included within the scope of the appended claims. Although specific terms are employed herein, they are used in a generic and descriptive sense only and not for purposes of limitation.

The following examples are offered by way of illustration and not by way of limitation.

EXAMPLES

Example 1. Targeting of the Y Chromosome Gene Sry Assisted by TALENs or CRISPR

A targeted deletion comprising a lacZ replacement allele for Sry was created with a targeting vector comprising, in order, an upstream homology arm of approximately 700 bp, a beta-galactosidase coding sequence (lacZ) followed by a polyadenylation signal, a neomycin resistance cassette flanked by loxP sites comprising a human ubiquitin C promoter, including the first exon, first intron, and part of the second exon, a neomycin phosphotransferase coding sequence, and a polyadenylation signal, and a downstream homology arm of approximately 650 bp. The allele created by correct targeting of the Sry gene with the targeting vector comprises a deletion of the approximately 1 kb Sry open reading frame and replacement with the lacZ-neo cassette such that the beta-galactosidase coding sequence is fused in-frame at the Sry start codon. The targeting vector was used to target the Sry gene in both the VGB6 (a.k.a. B6A6) C57BL/6 and the VGF1 (a.k.a. F1H4) C57BL6/129 F1 hybrid ES cell lines. VGF1 (F1H4) mouse ES cells were derived from hybrid embryos produced by crossing a female C57BL/6NTac mouse to a male 129S6/SvEvTac mouse. Therefore, VGF1 ES cells contain a Y chromosome from 129S6/SvEvTac mouse. The female XY mice produced from the VGF1 cell line contain a Y chromosome derived from 129S6/SvEvTac mouse.

Example 2. TALEN- or CRISPR-Induced Mutations in the Y Chromosome Gene Sry

Deletion mutations, presumably the result of non-homologous end joining (NHEJ) repair of double strand DNA breaks, ranging from 3 bp to 1.2 kb and larger were created in the Sry gene by the action of a TALEN or of CRISPR guide RNAs, in combination with Cas9 DNA endonuclease (see, FIG. 1). ES cells comprising the TALEN- and CRISPR-induced mutations in the Sry gene also carried random transgenic insertions of the NIH KOMP project VG12778 LTVEC (available via internet on the world wide web (www) at the URL "velocigene.com/komp/detail/12778"), which comprises a deletion of the Sry coding sequence and replacement with an insertion cassette comprising lacZ fused in-frame with the Sry start codon and a neomycin resistance gene flanked by homology arms of 38 and 37 kb and based on a BAC from the bMQ library (12957/SvEv Brd-Hprt b-m2). The LTVEC comprises in its homology arms all the known control elements for the expression of Sry. Its lacZ-encoded beta-galactosidase serves as a reporter for the tissue-specific and developmental stage-specific expression of the Sry gene. TALEN- and CRISPR-induced mutations accompanied by LTVEC insertions were created in both the VGB6 (a.k.a. B6A6) and VGF1 (a.k.a. F1H4) ES cell lines.

We obtained a TALEN (TALEN-1) designed to target part of the HMG box DNA binding motif coding sequence (upstream recognition sequence: 5'-TCCCGTGGTGAGAGGCAC-3' (SEQ ID NO: 72); downstream recognition sequence: 5'-TATTTTGCATGCTGGGAT-3' (SEQ ID NO: 73)) in the Sry gene. TALEN-1 was active in creating NHEJ mutations at the Sry locus in multiple experiments.

Both VGB6 and VGF1 mouse ES cells were created with TALEN-induced mutations. Table 1 contains a list of all the clones and the sizes of the deletion mutations they carry. (ND in Table 1 indicates that a mutation was detected by a qPCR assay, but the exact molecular nature of the mutation was not determined.) All clones also carry at least one copy of the NIH KOMP project VG12778 LTVEC.

TABLE 1

TALEN- and CRISPR-induced mutations in the Sry gene

| ES cell | Clone | Mutation inducing agent | Deletion (bp) |
|---|---|---|---|
| VGB6 | DE7 | TALEN-1 | 9 |
|  | DE11 | TALEN-1 | 303* |
|  | DG5 | TALEN-1 | 627 |
|  | DH1 | TALEN-1 | ND |
|  | EA2 | TALEN-1 | ND |
|  | ED4 | TALEN-1 | >1200 |
|  | EF4 | TALEN-1 | 16 |
|  | EG7 | TALEN-1 | >1200 |
| VGB6 | RD3 | TALEN-1 | >1200 |
|  | RE9 | TALEN-1 | ND |
|  | RF3 | TALEN-1 | 9 |
|  | RG7 | TALEN-1 | 15 |
|  | SF7 | TALEN-1 | 3 |
|  | SG11 | TALEN-1 | 6 |
|  | SH2 | TALEN-1 | >200 |
|  | SH11 | TALEN-1 | 2 |

TABLE 1-continued

TALEN- and CRISPR-induced mutations in the Sry gene

| ES cell | Clone | Mutation inducing agent | Deletion (bp) |
|---|---|---|---|
| VGF1 | TB1 | TALEN-1 | 11 |
|  | TC2 | TALEN-1 | 5 |
|  | UA5 | TALEN-1 | 15 |
|  | UB5 | TALEN-1 | 1201 |
|  | UE12 | TALEN-1 | 9 |
|  | WE11 | TALEN-1 | >1200 |
| VGB6 | OG6 | CRISPR-2 | 9 |
|  | QE8 | CRISPR-3 | 5 |
| VGF1 | AU-B6 | CRISPR-4 | 5 |
|  | AU-C12 | CRISPR-4 | 8 |
|  | AW-H5 | CRISPR-5 | 22 |

*Also contained a 50 bp insertion

The results of microinjections of the Sry mutant clones are set forth in Table 2 and the breeding results of sex-reversed females are set forth in Table 3.

TABLE 2

F0 generation VelociMice produced by microinjection of Sry mutant ES cell clones into 8-cell embryos

| ES Cell | Clone | Sry mutation | Female VM | Male VM |
|---|---|---|---|---|
| VGB6 | ED4 | >1 kb deletion | 2 | 0 |
|  | EG7 | >1 kb deletion | 19 | 0 |
|  | GB4 | None | 0 | 3 |
|  | GG1 | None | 0 | 5 |
|  | DE11 | 303 bp deletion; 50 bp insertion | 1 | 0 |
|  | DG5 | 627 bp deletion | 11 | 0 |
| VGF1 | TA3 | None | 0 | 5 |
|  | TA4 | None | 0 | 11 |
|  | TB1 | 11 bp deletion | 2 | 0 |
|  | TC2 | 5 bp deletion | 8 | 0 |
|  | TH4 | None | 2 | 6 |
|  | UB5 | 1,201 bp deletion | 6 | 0 |
|  | WE11 | >1.2 kb deletion | 7 | 0 |
|  | UA5 | 15 bp deletion | 4 | 0 |
|  | UE12 | 9 bp deletion | 8 | 0 |

TABLE 3

Breeding results of XY female VelociMice with mutations in the Sry gene

| ES Cell | Clone | Sry deletion (bp) | XY Female ID # | Litters Produced | Pups born |
|---|---|---|---|---|---|
| VGB6 | EG7 | >1,200 | 1460403 | 0 |  |
|  |  |  | 1460404 | 0 |  |
|  |  |  | 1460405 | 0 |  |
|  |  |  | 1460406 | 1 | 0* |
|  |  |  | 1460408 | 0 |  |
|  |  |  | 1460409 | 0 |  |
|  |  |  | 1460410 | 0 |  |
| VGB6 | DG5 | 627 | 1460428 | 0 |  |
|  |  |  | 1460429 | 0 |  |
|  |  |  | 1460430 | 0 |  |
|  |  |  | 1460431 | 0 |  |
|  |  |  | 1460432 | 0 |  |
|  |  |  | 1460436 | 0 |  |
|  |  |  | 1460437 | 0 |  |
|  |  |  | 1460438 | 0 |  |
|  |  |  | 1460410 | 0 |  |
| VGF1 | UB5 | 1,201 | 1525585 | 5 | 33 |
|  |  |  | 1525586 | 5 | 25 |
|  |  |  | 1525587 | 5 | 32 |
|  |  |  | 1525588 | 3 | 35 |
|  |  |  | 1525589 | 3 | 19 |

TABLE 3-continued

Breeding results of XY female VelociMice with mutations in the Sry gene

| ES Cell | Clone | Sry deletion (bp) | XY Female ID # | Litters Produced | Pups born |
|---|---|---|---|---|---|
| VGF1 | WE11 | >1,200 | 1525573 | 3 | 4 |
|  |  |  | 1525574 | 5 | 21 |
|  |  |  | 1525575 | 4 | 11 |
|  |  |  | 1525576 | 4 | 14 |
|  |  |  | 1525577 | 4 | 16 |
|  |  |  | 1525578 | 2 | 4 |
|  |  |  | 1525579 | 2 | 6 |
| VGF1 | TB1 | 11 | 1525700 | 5 | 30 |
|  |  |  | 1525701 | 4 | 28 |
| VGF1 | TC2 | 5 | 1525706 | 1 | 2 |
|  |  |  | 1525707 | 5 | 10 |
|  |  |  | 1525708 | 1 | 6 |
|  |  |  | 1525709 | 4 | 17 |
|  |  |  | 1525710 | 1 | 3 |
|  |  |  | 1525711 | 3 | 9 |
|  |  |  | 1525712 | 4 | 12 |
|  |  |  | 1525713 | 2 | 7 |
| VGF1 | UA5 | 15 | 1594102 | 2 | 5 |
|  |  |  | 1594103 | 2 | 7 |
|  |  |  | 1594104 | 1 | 3 |
|  |  |  | 1594105 | 2 | 15 |
| VGF1 | UE12 | 9 | 1594117 | 1 | 6 |
|  |  |  | 1594118 | 2 | 12 |
|  |  |  | 1594119 | 1 | 11 |
|  |  |  | 1594120 | 2 | 8 |
|  |  |  | 1594121 | 2 | 21 |
|  |  |  | 1594122 | 2 | 15 |
|  |  |  | 1594123 | 2 | 10 |

*XY Female ID# 1460406 had to be euthanized before birth because she had a near-term crisis and could not deliver. Her dead pups (4 male, 5 females) were recovered by dissection and none carried the Sry mutation.

All of the VelociMice with Sry mutations derived from VGB6 ES cells were female, as expected for inactivation of Sry (Table 2). Those without Sry mutations but carrying at least one copy of the NIH KOMP VG12778 LTVEC produced only male VelociMice (Table 2, clones GB4 and GG1). When 17 Sry mutant female B6 VelociMice were test bred, only one became pregnant after about four months of breeding set-up (Table 3), and that female had to be euthanized before birth because she had a near-term crisis and could not deliver. Her dead pups (4 male, 5 females) recovered by dissection were all WT; none carried the Sry mutation. It was concluded that nearly all Sry mutant mice made from VGB6 ES cells are sterile, which is in agreement with the literature on Sry mutations. However, our data demonstrated very different result with the VGF1 clones.

First, the VGF1 ES cells were maintained, as usual, in our KO-DMEM-like low osmotic strength growth medium that is feminizing: some of the microinjected XY clones grown in this medium will produce fertile XY females, i.e. an XY female phenomenon, even though they do not carry mutations. An example is clone TH4, which has no Sry mutation but carries at least one copy of the NIH KOMP VG12778 LTVEC. This clone produced 2 female and 6 male VelociMice (Table 2). Two other VGF1 clones with no Sry mutations (TA3 and TA4, Table 2) produced only male VelociMice. We wanted to determine if VGF1 XY ES cells with mutations in Sry might also be feminized by the medium. In other words, would they, unlike the VGB6 Sry mutant ES cells, produce some fertile XY Sry mutant females? (Note that VGB6 ES cells cannot be maintained in KO-DMEM-like low osmotic strength media and retain the ability to produce mice.) The answer is yes as shown in Table 3.

Six VGF1 ES cell clones with TALEN-induced small deletions ranging from 5 bp to over 1 kb were microinjected. All produced female VelociMice, 32 of which were bred. Remarkably, all of the Sry mutant XY female VelociMice were fertile; each produced at least one litter (Table 3). Many of the Sry mutant XY females produced multiple litters with normal litter sizes, while some of the XY females produced only one or two small litters. Out of 299 F1 mice from these breedings that have been genotyped, approximately half (146, 49%) are normal XY males or normal XX females. 174 (58%) of the F1 mice were phenotypic females, while 125 (42%) were phenotypic males. 26 of the females (15% of females, 8.7% of the total F1 generation) were XY females that inherited a mutant Sry allele. Because of meiotic non-disjunction events associated with XY oocytes, a number of aberrant genoytpes—XXY, XYY, XO, XXYY—some of which included mutant Sry alleles were observed in the F1 progeny of Sry mutant XY female VelociMice.

A method for the efficient creation of fertile XY female VelociMice from XY ES cells has been discovered. If inactivating mutations in the Sry gene in ES cells are created that have been maintained in the feminizing growth medium, a high proportion of fertile XY female mice are obtained that when bred to males produce mostly male and female mice with normal X and Y chromosomes.

Example 3. Embryo Recovery in KO-DMEM or DMEM after TALEN-Induced Mutations in the Y Chromosome Gene Sry Correct targeting of mouse Sry by LTVEC was confirmed or negated by genotyping of F1 offspring derived from F0 females, which were XY and carried Sry mutation. Co-segregation in F1 mice of the LacZ/Neo cassette with the Sry mutation (as assessed by Sry LOA assays) strongly suggests correct targeting. Failure of LacZ/Neo to co-segregate with the mutation indicates that the original clone contained an Sry deletion mutation (induced by TALEN) coupled with a LacZ/Neo transgenic insertion elsewhere in the genome.

Offspring from XY females with Sry mutations exhibited a variety of abnormal karyotypes at a high frequency (including XXY, XYY, and XO). Sex chromosome count was assessed by using unrelated loss of allele (LOA) assays for genes on X and Y chromosomes. The copy number of Sry was then determined using LOA assays. The presence of mutant Sry allele was inferred in mice in which the Y chromosome copy number exceeded the Sry copy number (for instance, 1 copy of Y and 0 copies of Sry, or 2 copies of Y and 1 copy of Sry). Lastly the presence of LacZ and Neo were determined using TaqMan assays.

In the original set of clones, which were created by Sry LTVEC together with TALEN nuclease and grown in KO-DMEM, it was evident that LacZ/Neo cassette was not co-segregating with the Sry mutation. A sample litter from these clones is shown in Table 4.

TABLE 4

Screening of clones generated by Sry LTVEC together with TALEN nuclease

| Mouse | Sex | X Chr Copy # | Y Chr Copy # | Sry Copy # | LacZ | Neo | Genotype | Comments |
|---|---|---|---|---|---|---|---|---|
| 1656721 | M | 1 | 1 | 1 | 0 | 0 | X+Y+ | |
| 1656722 | M | 1 | 1 | 1 | 1 | 1 | X+Y+ | LacZ/Neo present by Sry mutation absent |
| 1656723 | M | 1 | 1 | 1 | 0 | 0 | X+Y+ | |
| 1656724 | M | 1 | 2 | 1 | 0 | 0 | X+Y+YΔ | Sry mutation present but LacZ/Neo absent |
| 1656725 | F | 2 | 0 | 0 | 1 | 1 | X+X+ | LacZ/Neo present but Sry mutation absent |
| 1656726 | F | 2 | 1 | 0 | 0 | 0 | X+X+YΔ | Sry mutation present but LacZ/Neo absent |
| 1656727 | F | 2 | 1 | 0 | 1 | 1 | X+X+YΔ | |
| 1656728 | F | 1 | 0 | 0 | 1 | 1 | X+ | LacZ/Neo present but Sry mutation absent |
| 1656729 | F | 1 | 0 | 0 | 0 | 0 | X+ | |

In the subsequent set of clones, which were created by Sry LTVEC together with TALEN nuclease and grown in DMEM, the LacZ/Neo cassette was completely co-segregating with the Sry mutation, indicating correct targeting. A typical litter from these clones is shown in Table 5.

TABLE 5

Screening results for clones created by Sry LTVEC together with TALEN nuclease

| Mouse | Sex | X Chr Copy # | Y Chr Copy # | Sry Copy # | LacZ | Neo | Genotype |
|---|---|---|---|---|---|---|---|
| 1848360 | M | 1 | 1 | 1 | 0 | 0 | X+Y+ |
| 1848361 | M | 1 | 1 | 1 | 0 | 0 | X+Y+ |
| 1848362 | M | 1 | 1 | 1 | 0 | 0 | X+Y+ |
| 1848363 | M | 1 | 1 | 1 | 0 | 0 | X+Y+ |
| 1848364 | M | 1 | 2 | 1 | 1 | 1 | X+Y+YΔ |
| 1848365 | F | 2 | 1 | 0 | 1 | 1 | X+X+YΔ |
| 1848366 | F | 1 | 1 | 0 | 1 | 1 | X+YΔ |
| 1848367 | F | 1 | 1 | 0 | 1 | 1 | X+X+YΔ |

Figure 2:
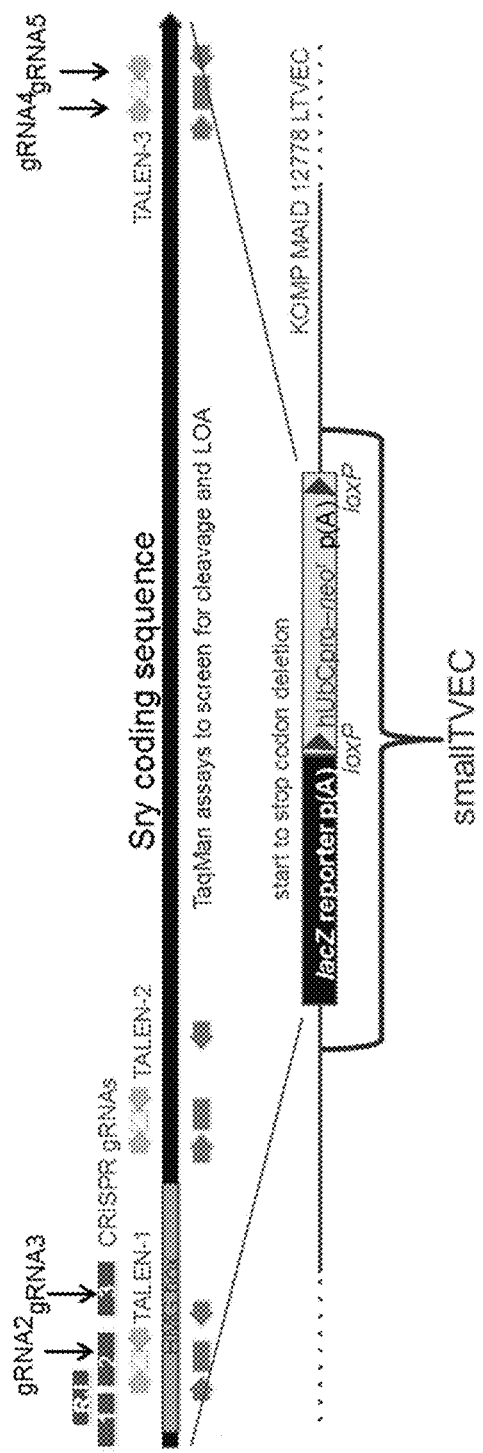
FIG. 2 provides a schematic of targeting the Sry gene with TALEN and CRISPR using a lacZ reporter gene. The Sry gene was targeted with both a LTVEC and a short-armed vector (smallTVEC) having homology arms smaller than a LTVEC in order to avoid challenging loci on the Y chromosome.

Example 4. TALEN and CRISPR-Assisted Targeting of Sry by SmallTVECs or LTVECs As depicted in FIG. 2, a targeted deletion comprising a lacZ replacement allele for Sry was created with either a LTVEC or a small targeting vector (smallTVEC) together with either TALEN nuclease or CRISPR guide RNAs, in combination with Cas9 DNA endonuclease. The smallTVEC comprised, in order, an upstream homology arm of approximately 700-800 bp, a beta-galactosidase coding sequence (lacZ) followed by a polyadenylation signal, a neomycin resistance cassette flanked by loxP sites comprising a human ubiquitin C promoter, including the first exon, first intron, and part of the second exon, a neomycin phosphotransferase coding sequence, and a polyadenylation signal, and a downstream homology arm of approximately 700-800 bp. The allele created by correct targeting of the Sry gene with the targeting vector comprises a deletion of the approximately 1 kb Sry open reading frame and replacement with the lacZ-neo cassette such that the beta-galactosidase coding sequence is fused in-frame at the Sry start codon. The targeting vector was used to target the Sry gene in the VGF1 (a.k.a. F1H4) C57BL6/129 F1 hybrid ES cell line and in the VGB6 ES cell line (a.k.a. B6A6). As illustrated in Table 6, clones produced using four different gRNAs and one TALEN pair were produced and screened for cleavage and loss of allele by TaqMan assays.

TABLE 6

Screening results for cleavage and loss of allele

| Location | gRNA or TALEN | Clones Screened | KO | Small TVEC Targeting Total targ. Eff. (%) |
|---|---|---|---|---|
| HMG box | gRNA 2 | 192 | 4 | 2.1 |
| HMG box | gRNA 3 | 192 | 5 | 2.6 |
| 3' end | gRNA 4 | 192 | 3 | 1.6 |
| 3' end | gRNA 5 | 192 | 5 | 2.6 |
| HMG box | TALEN pair 1 | 384 | 1 | 0.3 |
| n.a. | none | 384 | 1 | 0.3 |

Figure 3:
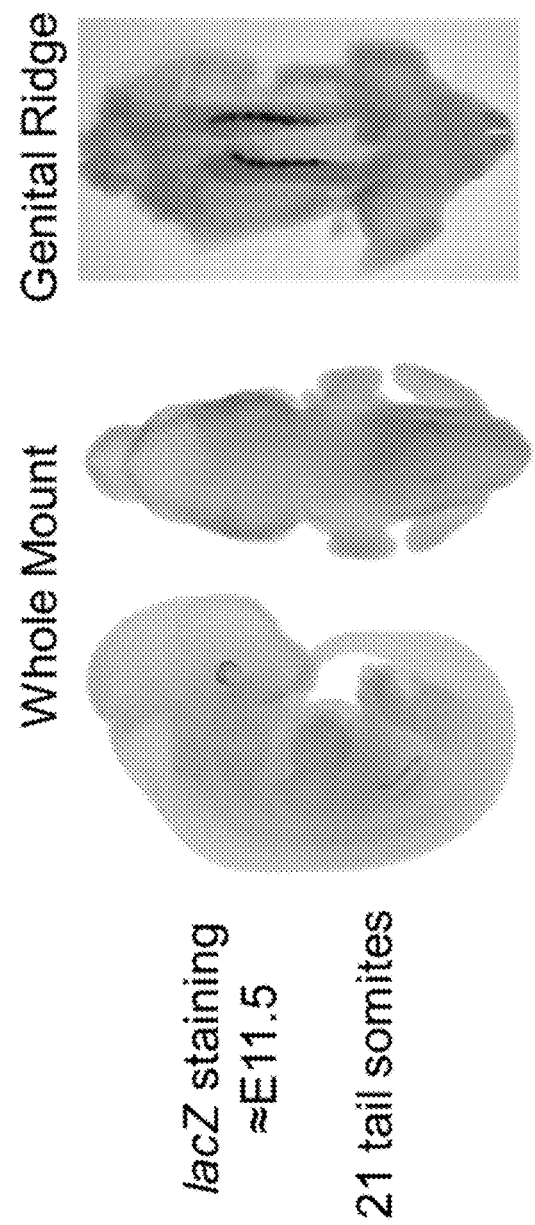
FIG. 3 illustrates LacZ expression in embryos.

The LTVEC transgenic clones produced embryos with the same lacZ pattern. FIG. 3 illustrates LacZ expression in the embryos.

Table 7 reports the fertility results of XY Females derived from ES cells grown in conventional DMEM-based medium that had TALEN-assisted LTVEC targeted deletion-replacement mutations of Sry. Unexpectedly compared with the results for a similar experiment with ES cells grown in KO-DEMEM-based medium (Table 3), LTVEC targeting in DMEM-based medium produced clones with correctly targeted Sry deletions and lacZ-neo insertions. Forty out of 41 XY$^{Sry(lacZ)}$ females derived from four targeted clones produced live born pups upon mating—a 98% fertility rate. Thus, we have devised two new ways to produce highly fertile XY females from mutant ES cells: (1) TALEN-induced inactivating mutations in Sry in ES cells grown in a KO-DMEM-based medium; and (2) TALEN-assisted LTVEC targeted precise deletion-replacement mutations in ES cells grown in DMEM-based medium.

TABLE 7

Production of Sry TALEN Mutant XY Females

| Clone | ES cell line | Allele description | XY female VelocMice | XY females bred | Fertile XY females | Fertility rates (%) |
|---|---|---|---|---|---|---|
| DMEM X-C4 | VGF1 | lacZ-neo targeted | 5 | 2 | 2 | 100 |
| X-E10 | VGF1 | lacZ-neo targeted | 1 | 1 | 1 | 100 |
| X0F3 | VGF1 | lacZ-neo targeted | 5 | 3 | 3 | 100 |
| X-G3 | VGF1 | lacZ-neo targeted | 9 | 3 | 2 | 67 |
| VGF1 Total | | | 53 | 41 | 40 | 98 |

Example 5. Large Deletion on the Y Chromosome Mediated by ZFNs

Figure 4:
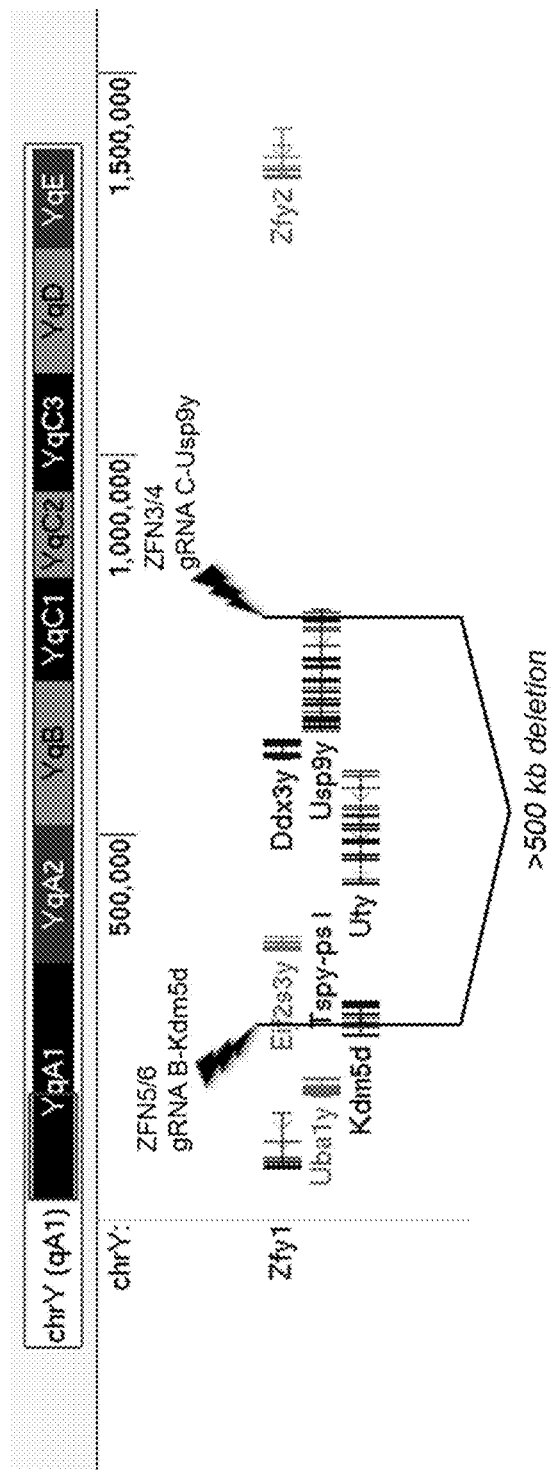
FIG. 4 provides a schematic of a large deletion of greater than 500 kb on the Y chromosome mediated by ZFNs or by CRISPR guide RNAs in combination with Cas9 DNA endonuclease.

As illustrated in FIG. 4, large deletions, 500 kb or greater, were made on the Y chromosome using ZFNs targeting the Kdm5d and the Usp9y genes. Table 8 provides examples of zinc finger sequences on the Y chromosome.

TABLE 8

Zinc Finger Sequence on the Y Chromosome

| Target Name | Y CHR Plate | Zinc Finger Sequence | ZFN# | SEQ ID NO: |
|---|---|---|---|---|
| KDM5D | NM011419-r43102a1 | ttAGGTAGGTAGACAGGGATgttttctg | ZFN1 | 42 |
| | NM011419-43108a1 | atCCAGTCtCTGAAGGAAGCTctgacta | ZFN2 | 43 |
| | NM011419-r19880a1 | caAAAGCTTCAGGGGGActcttacactc | ZFN3 | 44 |
| | NM011419-19887a1 | ttTGAGCAgGCTACACAGGAGtatactt | ZFN4 | 45 |
| | NM011419-r17347a1 | aaGCGGTGgCAATAGGCAaaagatgtgg | ZFN5 | 46 |
| | NM011419-17353a1 | ctGAAGTCCCCAAGGGAGTAtggagatg | ZFN6 | 47 |
| | NM011419-r17350a1 | agAAAGCGGTGGCAaTAGGCAaaagatg | ZFN7 | 48 |
| | NM011419-17356a1 | aaGTCCCCAAGGGAGTAtggagatgccc | ZFN8 | 49 |
| DDX3Y | NM012008-r8130a1 | acTCCAACGACTATGACcactccgttca | ZFN1 | 50 |
| | NM012008-8136a1 | acAGATCAGATGAAGATgactggtcaaa | ZFN2 | 51 |
| | NM012008-r7172a1 | ctTTCAAGGAAAAAAAGaacaaaaccca | ZFN3 | 52 |
| | NM012008-7178a1 | ggTCTGTGATAAGGACAGTTcaggatgg | ZFN4 | 53 |
| | NM012008-r20472a1 | taAATCTGACTGAGAATGGGtagtagaa | ZFN5 | 54 |
| | NM012008-20479a1 | caGATGGTCCAGGAGAGGCTttgaaggc | ZFN6 | 55 |
| | NM012008-r7267a1 | atTGGGCTTCCcTCTGGAatcacgagat | ZFN7 | 56 |
| | NM012008-7274a1 | ttTCAGTGATCGTGGAAGTGgatccagg | ZFN8 | 57 |
| USP9Y | NM148943-r92561a1 | ctGGTTTGGAAATCGTActgtaaaagac | ZFN1 | 58 |
| | NM148943-92567a1 | gcAAAGAGGTTGAGGATttggacatatt | ZFN2 | 59 |
| | NM148943-r11830a1 | gaGGAGTTGTTGGAGAAGTCtcattgga | ZFN3 | 60 |
| | NM148943-11836a1 | atATGAACAAGGCCAAGgtgatgctcca | ZFN4 | 61 |
| | NM148943-r108581a1 | acTCAGAAGAAGGATTAGGAatgctttg | ZFN5 | 62 |
| | NM148943-108588a1 | atGCTTAGaAATGTATCAGTTcatcttg | ZFN6 | 63 |
| | NM148943-r16244a1 | tcCATAAGGATTTTGGAaaaagacacag | ZFN7 | 64 |
| | NM148943-16251a1 | agGCTGTGAGTGGATGGAAGtttgaaat | ZFN8 | 65 |

In one experiment, 3.3 million ES cells from VGB6 clones D-G5 and E-G7 (Table 3) were electroporated with the ZFN mRNA pairs Kdm5d-ZFN5(NM011419-r17347a1)/ZFN6(NM011419-17353a1) and Usp9y-ZFN3(NM148943-r11830a1)/ZFN4(NM148943-11836a1) (10 ug each) and with an LTVEC targeting the Ch25h gene (0.67 ug), to provide selection for puromycin resistance. Puromycin resistant colonies were picked and screened for the deletion. The results are shown in Table 9.

TABLE 9

Screening Results for large Y chromosome deletion in 12778D-G5 and 12778E-G7

| Parental Clone | # of Puromycin-resistant Colonies | # of Colonies Screened | # Confirmed Deleted Clones |
|---|---|---|---|
| 12778D-G5 | 244 | 192 | 4 |
| 12778E-G7 | 638 | 384 | 8 |

Table 10 shows the exact sizes of the greater than 500 kb deletions that were precisely determined for one deletion clone (4306A-D5) derived from the E-G7 parental clone (Table 3) and two deletion clones (4306E-C4 and 4306F-A12) derived from the D-G5 parental clone (Table 3).

TABLE 10

ZFN-mediated deletions of Kdm5d and Usp9y

| Clone | Deletion Coordinates on Y Chromosome | Size (bp) |
|---|---|---|
| 4306A-D5 | 250569-785404 | 534835 |
| 4306E-C4 | 520363-785402 | 535039 |
| 4306F-A12 | 250373-785404 | 535031 |

Deletion of the Kdm5d, Eif2s3y, Uty, Ddx3y, and Usp9y genes (FIG. 4) was confirmed in the deletion loss-of-allele assays and DNA sequencing as shown in FIG. 5. Clone 4306A-D5 produced nine XY female fully ES cell-derived VelociMice upon microinjection into 8-cell stage embryos and transfer to surrogate mothers. None of the XY females from clone 4306A-D5 were fertile.

Example 6. Large Deletion on the Y Chromosome Mediated by CRISPR/Cas

A large deletion of the on the Y chromosome targeting the region between the Kdm5d and the Usp9y genes was made utilizing CRISPR guide RNAs in combination with Cas9 DNA endonuclease. gRNAs were designed to target the Kdm5d gene and the Usp9y gene. The following gRNAs were designed to target Kdm5d: Kdm5dgA (Guide #1) UUUGCCGAAUAUGCUCUCGU (SEQ ID NO:66); Kdm5dgB (Guide #2) UUGCCGAAUAUGCUCUCGUG (SEQ ID NO:67); and Kdm5dgC (Guide #5) CGGGCAU-CUCCAUACUCCCU (SEQ ID NO:68). The following gRNAs were designed to target Usp9y: Usp9ygA (Guide #1) UAGCUCGUUGUGUAGCACCU (SEQ ID NO:69); Usp9ygB (Guide #1) UAUAGUUUCUUCGGGGUAAC (SEQ ID NO:70); and Usp9ygC (Guide #2) GGAUAC-CCUUCUAUAGGCCC (SEQ ID NO:71).

VGF1 mouse ES cells were electroporated with 5 µg of a plasmid that expressed Cas9 and 10 µg each of plasmids that expressed the Kdm5d gRNA B and Usp9y gRNA C and with an LTVEC targeting the Ch25h gene (0.67 ug), to provide selection for puromycin resistance.

As illustrated in FIG. 4, Kdm5dgB (gRNA B) and Usp9ygC (gRNA C) were used to target the deletion of the Kdm5d and Usp9y genes. The resulting clones were screened for deletion by loss-of-allele assays for sequences at the Kdm5d and Usp9y genes and the genes in between (Eif2s3y, Uty, and Ddx3y) and for genes outside the targeted deletion (Zfy2 and Sry). As shown in Table 11, four clones comprising the large deletion were obtained. Clone R-A8 produced seven XY male and 3 XY female fully ES cell-derived VelociMice upon microinjection into 8-cell stage embryos and transfer to surrogate mothers.

TABLE 11

TaqMan assay confirming large deletion mediated by CRISPR guide RNAs and Cas9

| Clone | Loss-of-allele Copy Number Determination | | | | | Note |
|---|---|---|---|---|---|---|
| | 19178TD (Eif2s3y) | 16697TD (Uty) | Ddx3yZF12 (Ddx3y) | Zfy2 | Sry | |
| Q-F1 | 0 | 0 | 0 | 1 | 1 | Large deletion |
| R-A8 | 0 | 0 | 0 | 1 | 1 | Large deletion |
| R-C20 | 0 | 0 | 0 | ~0.5 | 1 | Large deletion, partial loss Y |
| R-E11 | 1 | 1 | 1 | 1 | 1 | clone add as WT control |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. If the information associated with a citation, such as a deposit number changes with time, the version of the information in effect at the effective filing date of the application is intended, the effective filing date meaning the actual filing date or date of a priority application first providing the citation. Unless otherwise apparent from the context of any embodiment, aspect, step or feature of the invention can be used in combination with any other. Reference to a range includes any integers within the range, any subrange within the range. Reference to multiple ranges includes composites of such ranges.

That which is claimed:

1. A method for making a mouse XY embryonic stem (ES) cell line capable of producing a fertile XY female mouse in an F0 generation, comprising:
   (a) modifying a mouse XY embryonic stem (ES) cell to comprise a genetic modification comprising a deletion that inactivates the endogenous mouse Sry gene, wherein the mouse XY ES cell comprises a Y chromosome from a 129S6 strain; and
   (b) culturing the modified mouse XY ES cell under conditions to produce a mouse XY ES cell line capable of producing a fertile XY female mouse in an F0 generation, wherein upon introduction of the modified mouse XY ES cell into a host embryo and following gestation of the host embryo to produce F0 mice, at least 60% of the F0 mice are XY females which upon attaining sexual maturity are fertile.

2. A method for making a fertile XY female mouse in an F0 generation, comprising:
   (a) introducing a mouse XY embryonic stem (ES) cell into a host embryo, wherein the XY ES cell comprises a Y chromosome from a 129S6 strain and a genetic modification comprising a deletion that inactivates the endogenous mouse Sry gene;
   (b) gestating the host embryo; and
   (c) obtaining F0 mice following gestation of the host embryo, wherein at least 60% of the F0 mice are XY females which upon attaining sexual maturity are fertile.

3. The method of claim 1, wherein the mouse XY ES cell is isolated from a mouse that is a cross between a 129S6 strain and a C57BL/6 strain.

4. The method of claim 3, wherein the mouse XY ES cell is isolated from a hybrid embryo produced by crossing a female C57BL/6NTac mouse to a male 129S6/SvEvTac mouse.

5. The method of claim 4, wherein the mouse XY ES cell is a VGF1 mouse ES cell.

6. The method of claim 1, wherein the mouse XY ES cell is not cultured in a feminizing medium.

7. The method of claim 1, wherein the culturing step comprises culturing the modified mouse XY ES cell in a medium comprising: (1) a base medium comprising about 3 mg/mL sodium chloride and about 2.2 mg/mL sodium bicarbonate and having an osmolality of about 218 mOsm/kg; and (2) supplements that maintain the modified mouse ES cell in culture.

8. The method of claim 1, wherein the genetic modification further comprises an insertion of one or more nucleotides, a substitution of one or more nucleotides, or a combination thereof.

9. The method of claim 8, wherein the genetic modification further comprises a knockout; a knockin; a replacement of an endogenous nucleic acid sequence with a homologous, orthologous, or heterologous sequence; or a combination thereof.

10. The method of claim 8, wherein the genetic modification further comprises an insertion of a nucleic acid encoding a selectable marker and/or a nucleic acid encoding a reporter gene operably linked to a promoter active in the mouse XY ES cell.

11. The method of claim 8, wherein the genetic modification further comprises an insertion of a nucleic acid encoding a reporter gene operably linked to the endogenous Sry promoter.

12. The method of claim 1, further comprising modifying the XY ES cell to comprise at least one additional targeted genetic modification of a polynucleotide of interest.

13. The method of claim 1, wherein the genetic modification is generated by introducing into the mouse XY ES cell a nuclease agent that induces a nick or a double-strand break at a recognition site on the Y chromosome.

14. The method of claim 1, wherein the genetic modification is generated by introducing into the XY ES cell a targeting vector comprising an insert polynucleotide flanked by first and second homology arms corresponding to first and second target sites at a target genomic locus on the Y chromosome, wherein the mouse XY ES cell is modified to comprise the insert polynucleotide at the target genomic locus.

15. The method of claim 1, wherein the genetic modification is generated by introducing into the XY ES cell:
   (i) a nuclease agent that induces a nick or a double-strand break at a recognition site on the Y chromosome; and
   (ii) a targeting vector comprising an insert polynucleotide flanked by first and second homology arms corresponding to first and second target sites at a target genomic locus on the Y chromosome,
   wherein the mouse XY ES cell is modified to comprise the insert polynucleotide at the target genomic locus.

16. The method of claim 13, wherein the nuclease agent is a zinc finger nuclease (ZFN), a Transcription Activator-Like Effector Nuclease (TALEN), a meganuclease, or a Clustered Regularly Interspaced Short Palindromic Repeats (CRISPR)-associated (Cas) protein and a guide RNA (gRNA).

17. The method of claim 16, wherein the nuclease agent is the Cas protein and the gRNA, wherein the Cas protein is a Cas9 protein, and wherein the gRNA comprises:
   (a) a CRISPR RNA (crRNA) that targets the recognition site, wherein the recognition site is immediately flanked by a Protospacer Adjacent Motif (PAM) sequence; and
   (b) a trans-activating CRISPR RNA (tracrRNA).

18. The method of claim 17, wherein the gRNA targets a sequence comprising SEQ ID NO: 10, SEQ ID NO: 11, or SEQ ID NO: 12.

19. The method of claim 16, wherein the nuclease agent is the TALEN.

20. The method of claim 19, wherein the TALEN targets a sequence comprising SEQ ID NO: 72 and a sequence comprising SEQ ID NO: 73.

21. The method of claim 2, wherein the F0 XY female mouse is fertile when crossed to a wild-type mouse.

22. The method of claim 21, wherein the wild-type mouse is a C57BL/6 mouse.

23. The method of claim 2, wherein upon introduction of the modified mouse XY ES cell into the host embryo and following gestation of the host embryo, at least 80% of the F0 mice are XY females which upon attaining sexual maturity are fertile.

24. The method of claim 2, wherein upon introduction of the modified mouse XY ES cell into the host embryo and following gestation of the host embryo, at least 90% of the F0 mice are XY females which upon attaining sexual maturity are fertile.

25. The method of claim 2, wherein upon introduction of the modified mouse XY ES cell into the host embryo and following gestation of the host embryo, at least 95% of the F0 mice are XY females which upon attaining sexual maturity are fertile.

26. The method of claim 2, wherein the mouse XY ES cell is isolated from a mouse that is a cross between a 129S6 strain and a C57BL/6 strain.

27. The method of claim 26, wherein the mouse XY ES cell is isolated from a hybrid embryo produced by crossing a female C57BL/6NTac mouse to a male 129S6/SvEvTac mouse.

28. The method of claim 27, wherein the mouse XY ES cell is a VGF1 mouse ES cell.

29. The method of claim 2, wherein the genetic modification further comprises an insertion of one or more nucleotides, a substitution of one or more nucleotides, or a combination thereof.

30. The method of claim 2, wherein the XY ES cell is isolated from a hybrid embryo produced by crossing a female C57BL/6NTac mouse to a male 129S6/SvEvTac mouse, and upon introduction of the modified mouse XY ES cell into the host embryo and following gestation of the host embryo, at least 80% of the F0 mice are XY females which upon attaining sexual maturity are fertile.

31. The method of claim 30, wherein the XY ES cell is a VGF1 ES cell.

32. The method of claim 2, wherein the host embryo is a pre-morula stage embryo.

33. The method of claim 1, wherein upon introduction of the modified mouse XY ES cell into the host embryo and following gestation of the host embryo, at least 80% of the F0 mice are XY females which upon attaining sexual maturity are fertile.

34. The method of claim 1, wherein upon introduction of the modified mouse XY ES cell into the host embryo and following gestation of the host embryo, at least 90% of the F0 mice are XY females which upon attaining sexual maturity are fertile.

35. The method of claim 1, wherein upon introduction of the modified mouse XY ES cell into the host embryo and following gestation of the host embryo, at least 95% of the F0 mice are XY females which upon attaining sexual maturity are fertile.

36. The method of claim 29, wherein the genetic modification further comprises a knockout; a knockin; a replacement of an endogenous nucleic acid sequence with a homologous, orthologous, or heterologous sequence; or a combination thereof.

37. The method of claim 29, wherein the genetic modification further comprises an insertion of a nucleic acid encoding a selectable marker and/or a nucleic acid encoding a reporter gene operably linked to a promoter active in the mouse XY ES cell.

38. The method of claim 29, wherein the genetic modification further comprises an insertion of a nucleic acid encoding a reporter gene operably linked to the endogenous Sry promoter.

39. The method of claim 2, wherein the XY ES cell further comprises at least one additional targeted genetic modification of a polynucleotide of interest.

40. The method of claim 15, wherein the first homology arm is from about 400-1000 base pairs, and the second homology arm is from about 400-1000 base pairs.

41. The method of claim 15, wherein the sum total of the first homology arm and the second homology arm is at least 10 kb.

* * * * *